US011542256B2

(12) United States Patent
Li et al.

(10) Patent No.: US 11,542,256 B2
(45) Date of Patent: Jan. 3, 2023

(54) VINYLHETEROCYCLES AS RHO-ASSOCIATED COILED-COIL KINASE (ROCK) INHIBITORS

(71) Applicant: ANGION BIOMEDICA CORP., Uniondale, NY (US)

(72) Inventors: An-Hu Li, Commack, NY (US); Dibyendu Dana, Elmont, NY (US); Dong Sung Lim, Fair Lawn, NJ (US); Satishkumar Gadhiya, Jamaica, NY (US); Dawoon Jung, Tenafly, NJ (US); Prakash Narayan, East Northport, NY (US); Quaisar Ali, Franklin Square, NY (US); Swarnalatha Paka, Elmont, NY (US); Itzhak D. Goldberg, Englewood, NJ (US)

(73) Assignee: Angion Biomedica Corp., Uniondale, NY (US)

( * ) Notice: Subject to any disclaimer, the term of this patent is extended or adjusted under 35 U.S.C. 154(b) by 21 days.

(21) Appl. No.: 16/643,805

(22) PCT Filed: Aug. 31, 2018

(86) PCT No.: PCT/US2018/049225
§ 371 (c)(1),
(2) Date: Mar. 2, 2020

(87) PCT Pub. No.: WO2019/046795
PCT Pub. Date: Mar. 7, 2019

(65) Prior Publication Data
US 2020/0231576 A1    Jul. 23, 2020

Related U.S. Application Data

(60) Provisional application No. 62/553,885, filed on Sep. 3, 2017.

(51) Int. Cl.
*C07D 401/14*    (2006.01)
*C07D 403/14*    (2006.01)

(52) U.S. Cl.
CPC ......... *C07D 403/14* (2013.01); *C07D 401/14* (2013.01)

(58) Field of Classification Search
CPC ............................ C07D 401/14; C07D 403/14
See application file for complete search history.

(56) References Cited

U.S. PATENT DOCUMENTS

| | | |
|---|---|---|
| 5,322,756 A | 6/1994 | Ziolo |
| 7,758,972 B2 | 7/2010 | Egawa et al. |
| 7,951,433 B2 | 5/2011 | Tanaka |
| 8,357,693 B2 | 1/2013 | Bartolozzi et al. |
| 8,916,576 B2 | 12/2014 | Bartolozzi et al. |
| 9,440,961 B2 | 9/2016 | Bartolozzi et al. |
| 9,682,963 B2 | 6/2017 | Boland et al. |
| 9,815,820 B2 | 11/2017 | Poyurovsky et al. |
| 9,850,234 B2 | 12/2017 | Boland et al. |
| 10,183,931 B2 | 1/2019 | Poyurovsky et al. |
| 10,570,123 B2 | 2/2020 | Bartolozzi et al. |
| 2008/0085904 A1 | 4/2008 | Eggenweiler et al. |
| 2010/0101643 A1 | 4/2010 | Takahashi et al. |
| 2015/0297679 A1 | 10/2015 | Hafezi-Moghadam |
| 2016/0213664 A1 | 7/2016 | McKerracher et al. |
| 2016/0346224 A1 | 12/2016 | Macdonald |
| 2017/0092435 A1 | 3/2017 | Tsuna et al. |
| 2017/0246181 A1 | 8/2017 | Rosen et al. |
| 2017/0283446 A1 | 10/2017 | Fan et al. |
| 2017/0313680 A1 | 11/2017 | Rosen et al. |
| 2019/0048317 A1 | 2/2019 | Eto et al. |
| 2019/0177311 A1 | 6/2019 | Bartolozzi et al. |
| 2019/0300526 A1 | 10/2019 | Fan et al. |
| 2019/0308953 A1 | 10/2019 | Poyurovsky et al. |
| 2019/0328721 A1 | 10/2019 | Nam et al. |

FOREIGN PATENT DOCUMENTS

| | | |
|---|---|---|
| CN | 106916145 A | 7/2017 |
| CN | 107019698 A | 8/2017 |
| CN | 110200972 A | 9/2019 |
| JP | 2003-531112 A | 10/2003 |
| JP | 2008-509175 A | 3/2008 |
| JP | 2010-501003 A | 1/2010 |
| JP | 2010-504295 A | 2/2010 |
| JP | 2019/112307 A | 7/2019 |
| KR | 101892154 B1 | 8/2018 |
| WO | WO-01/46151 A1 | 6/2001 |
| WO | WO-2002/072578 A2 | 9/2002 |

(Continued)

OTHER PUBLICATIONS

Almirante, N. et al., A general, [1+4] approach to the synthesis of 3(5)-substituted pyrazoles from aldehydes, Tetrahedron Lett., 39(20):3287-3290 (1998).
Baba, I. et al., Inhibitory effects of fasudil on renal interstitial fibrosis induced by unilateral ureteral obstruction, Mol. Med. Rep., 12(6):8010-20 (2015).
Baba, I. et al., Partial deletion of the ROCK2 protein fails to reduce renal fibrosis in a unilateral ureteral obstruction model in mice, Mol. Med. Rep., 13(1):231-6 (2016).
Bellassoued, M. and Majidi, A., A simple and highly stereoselective route to E-.alpha.,.beta.-unsaturated aldehydes, J. Org. Chem., 58(9):2517-2522 (1993).
Boerma, M. et al., Comparative gene expression profiling in three primary human cell lines after treatment with a novel inhibitor of Rho kinase or atorvastatin, Blood Coagulation & Fibrinolysis, 19(7):709-718 (2008).

(Continued)

*Primary Examiner* — Brian E McDowell
(74) *Attorney, Agent, or Firm* — Choate, Hall & Stewart LLP

(57) ABSTRACT

The present invention provides compounds having formula (I): and pharmaceutically acceptable salts thereof, wherein Cy1, Cy2, Cy3, R, $R^1$, $R^2$, $R^3$, $A^1$ and $A^2$ are as described generally and in classes and subclasses herein, and additionally provides pharmaceutical compositions thereof, and methods for the use thereof for the treatment of any of a number of conditions or diseases in which inhibiting ROCK1, ROCK2, or ROCK1/2 has a therapeutically useful role.

22 Claims, 3 Drawing Sheets

(56) References Cited

FOREIGN PATENT DOCUMENTS

| | | |
|---|---|---|
| WO | WO-2006/105081 A2 | 10/2006 |
| WO | WO-2008/022164 A2 | 2/2008 |
| WO | WO-2008/034600 A1 | 3/2008 |
| WO | WO-2008/054599 A2 | 5/2008 |
| WO | WO-2008/120810 A1 | 10/2008 |
| WO | WO-2010/104851 A1 | 9/2010 |
| WO | WO-2011/011312 A1 | 1/2011 |
| WO | WO-2011/107608 A1 | 9/2011 |
| WO | WO-2012/040499 A2 | 3/2012 |
| WO | WO-2013/089087 A1 | 6/2013 |
| WO | WO-2014/055996 A2 | 4/2014 |
| WO | WO-2014/093773 A1 | 6/2014 |
| WO | WO-2014/118133 A1 | 8/2014 |
| WO | WO-2015/157556 A1 | 10/2015 |
| WO | WO-2015/190467 A1 | 12/2015 |
| WO | WO-2016/010950 A1 | 1/2016 |
| WO | WO-2016/049568 A1 | 3/2016 |
| WO | WO-2016/081554 A1 | 5/2016 |
| WO | WO-2016/112305 A1 | 7/2016 |
| WO | WO-2016/144936 A1 | 9/2016 |
| WO | WO-2016/204256 A1 | 12/2016 |
| WO | WO-2017/188357 A1 | 11/2017 |
| WO | WO-2017/210526 A1 | 12/2017 |
| WO | WO-2018/052953 A1 | 3/2018 |
| WO | WO-2018/167103 A1 | 9/2018 |
| WO | WO-2018/167142 A1 | 9/2018 |
| WO | WO-2018/193006 A1 | 10/2018 |
| WO | WO-2019/006324 A1 | 1/2019 |
| WO | WO-2019/046795 A1 | 3/2019 |
| WO | WO-2019/066662 A1 | 4/2019 |
| WO | WO-2019/066664 A1 | 4/2019 |
| WO | WO-2019/089468 A1 | 5/2019 |
| WO | WO-2019/099457 A1 | 5/2019 |
| WO | WO-2019/111048 A1 | 6/2019 |
| WO | WO-2019/126424 A1 | 6/2019 |
| WO | WO-2019/126431 A1 | 6/2019 |
| WO | WO-2021/016256 A2 | 1/2021 |
| WO | WO-2022/020381 A1 | 1/2022 |

OTHER PUBLICATIONS

Clinical Trials, 11 pages (2020), <https://clinicaltrials.gov/ct2/results/download_fields?down_count=10000&down_flds=all&down_fmt=pdf&term=KD025&flds=a&flds=b&flds=y>. Retrieved on Jun. 9, 2020.

Flynn, R. et al., Targeted Rho-associated kinase 2 inhibition suppresses murine and human chronic GVHD through a Stat3-dependent mechanism, Blood, 127(17):2144-2154 (2016).

Fu, P. et al., Signaling mechanism of renal fibrosis in unilateral ureteral obstructive kidney disease in ROCK1 knockout mice, J. Am. Soc. Nephrol. 17(11):3105-14 (2006).

Hu, Y. B., et al., Roles of Rho/Rock signaling pathway in silica induced epithelial-mesenchymal transition in human bronchial epithelial cells, Biomed. Environ. Sci., 26(7):571-6 (2013).

International Search Report for PCT/EP2014/051546, 2 pages, (dated Jan. 4, 2014).

International Search Report for PCT/US2018/049225, 4 pages (dated Dec. 18, 2018).

Kinoshita, M. et al., An Enantiospecific Synthesis of the C-21-C-37 Segment of the Aglycon of Amphotericin B, Bull. Chem. Soc. Jpn., 60:2151-2162 (1987).

Kolavennu, V., Zeng, L., Peng, H., Wang, Y., Danesh, F. R. Targeting of RhoA/ROCK signaling ameliorates progression of diabetic nephropathy independent of glucose control, Diabetes, 57(3):714-23 (2008).

Komers, R. et al., Rho kinase inhibition protects kidneys from diabetic nephropathy without reducing blood pressure, Kidney Int., 79(4):432-42 (2011).

Lee, J. H. et al., Selective ROCK2 inhibition in focal cerebral ischemia, Annals of Clinical and Translational Neurology, 1(1):2-14 (2014).

Loirand, G., Rho Kinases in Health and Disease: From Basic Science to Translational Research. Pharmacol. Rev., 67(4), 1074-95. (2015).

Luo, W. et al., Spironolactone lowers portal hypertension by inhibiting liver fibrosis, ROCK-2 activity and activating NO/PKG pathway in the bile-duct-ligated rat, PLoS One, 7(3):e34230 (2012).

Mardilovich, K. et al., Targeting Rho GTPase signaling for cancer therapy, Future Oncology, 8(2):165-177 (2012).

Nagatoya, K. et al., Y-27632 prevents tubulointerstitial fibrosis in mouse kidneys with unilateral ureteral obstruction. Kidney Int., 61(5):1684-95 (2002).

Natchev, I. A., Total synthesis, enzyme-substrate interactions and herbicidal activity of plumbemicin A and B (N-1409), Tetrahedron, 44(5):1511-1522 (1988).

Niego, B. et al., Selective inhibition of brain endothelial Rhokinase-2 provides optimal protection of an in vitro blood-brain barrier from tissue-type plasminogen activator and plasmin, PLoS One, 12(5):e0177332 (2017).

NIHR HSRIC, Netarsudil for open-angle glaucoma or ocular hypertension, Birmingham: NIHR Horizon Scanning Research & Intelligence Centre, Horizon Scanning Review (2016).

Shi, J. et al., Distinct roles for ROCK1 and ROCK2 in the regulation of cell detachment, Cell Death Dis., 4(2):e483 (2013).

Tang, F. C. et al., Simvastatin attenuated rat thoracic aorta remodeling by decreasing ROCK2-mediated CyPA secretion and CD147-ERK1/2-cyclin pathway, Molecular Medicine Reports, 16(6):8123-8129 (2017).

Tengesdal, I. W. et al., The selective ROCK2 inhibitor KD025 reduces IL-17 secretion in human peripheral blood mononuclear cells independent of IL-1 and IL-6, European Journal of Immunology, 48(10):1679-1686 (2018).

Written Opinion for PCT/US2018/049225, 5 pages (dated Dec. 18, 2018).

Zanin-Zhorov, A. et al., Cutting Edge: Selective Oral ROCK2 Inhibitor Reduces Clinical Scores in Patients with Psoriasis Vulgaris and Normalizes Skin Pathology via Concurrent Regulation of IL-17 and IL-10, Journal of Immunology, 198(10):3809-3814 (2017).

Zanin-Zhorov, A. et al., Selective oral ROCK2 inhibitor downregulates IL-21 and IL-17 secretion in human T cells via STAT3-dependent mechanism, Proceedings of the National Academy of Sciences of the United States of America, 111(47):16814-16819 (2014).

Zhu, L. et al., The selectivity and promiscuity of brain-neuroregenerative inhibitors between ROCK1 and ROCK2 isoforms: An integration of SB-QSSR modelling, QM/MM analysis and in vitro kinase assay, SAR and QSAR in Environmental Research, 27(1):47-65 (2016).

Qian, K. et al., Hit to Lead Account of Discovery of a New Class of Inhibitors of Pim Kinases and Crystallographic Studies Revealing and Unusual Kinase Binding Mode, J. Med. Chem., 52:1814-1827 (2009).

Santos, J. et al., Exploring the coordination chemistry of isomerizable terpyridine derivatives for successful analyses of cis and trans isomers by travelling wave ion mobiliity mass spectrometry, Analyst, 137:4045-4051 (2012).

Zhang, Y. et al., Switchable sensitizers stepwise lighting up lanthanide emissions, Scientific Reports, 5(9335):1-5 (2015).

VINYLHETEROCYCLES AS RHO-ASSOCIATED COILED-COIL KINASE (ROCK) INHIBITORS

CROSS-REFERENCE TO RELATED APPLICATIONS

This application claims benefit of U.S. Provisional Patent Application Ser. No. 62/553,885, filed Sep. 3, 2017, the priority date of which is hereby claimed.

BACKGROUND OF THE INVENTION

The Rho-associated coiled-coil kinase family members, consisting of Rho-associated kinase 1 (ROCK1) and Rho-associated kinase 2 (ROCK2), are serine-threonine kinases that are activated by Rho GTPases. Both ROCK1 and ROCK2 are involved in a wide range of cellular processes including actin cytoskeleton organization, smooth muscle cell contraction, adhesion, migration, proliferation, apoptosis and fibrosis (Loirand, G. Rho Kinases in Health and Disease: From Basic Science to Translational Research. *Pharmacol. Rev.* 2015, 67(4), 1074-95). The ROCK signaling cascade, modulated by fibrogenic growth factors including TGFβ1, angiotensin I, PDGF and endothelin-I, participates in epithelial to mesenchymal transition (Hu, Y. B., Li, X., Liang, G. N., Deng, Z. H., Jiang, H. Y., Zhou, J. H. Roles of Rho/Rock signaling pathway in silica-induced epithelial-mesenchymal transition in human bronchial epithelial cells. *Biomed. Environ. Sci.* 2013, 26(7), 571-6). Evidence for the potential role of this pathway in renal fibrosis comes from early studies that used pharmacologic inhibition of ROCK with Y-27632 or fasudil, which are selective but ROCK1/2 dual inhibitors, i.e., they inhibit both ROCK 1 and ROCK2 but not other kinases. Use of ROCK1/2 dual inhibitors prevented tubulointerstitial fibrosis in obstructive renal disease, mitigated nephropathy in subtotally nephrectomized, spontaneously hypertensive rats and attenuated glomerulosclerosis in Dahl salt-sensitive rats (Komers, R., Oyama, T. T., Beard, D. R., Tikellis, C., Xu, B., Lotspeich, D. F., Anderson, S. Rho kinase inhibition protects kidneys from diabetic nephropathy without reducing blood pressure. *Kidney Int.* 2011, 79(4), 432-42. Nagatoya, K., Moriyama, T., Kawada, N., Takeji, M., Oseto, S., Murozono, T., Ando, A., Imai, E., Hori, M. Y-27632 prevents tubulointerstitial fibrosis in mouse kidneys with unilateral ureteral obstruction. *Kidney Int* 2002, 61(5), 1684-95. Baba, I., Egi, Y., Utsumi, H., Kakimoto, T., Suzuki, K. Inhibitory effects of fasudil on renal interstitial fibrosis induced by unilateral ureteral obstruction. *Mol. Med. Rep.* 2015, 12(6), 8010-20. Kolavennu, V., Zeng, L., Peng, H., Wang, Y., Danesh, F. R. Targeting of RhoA/ROCK signaling ameliorates progression of diabetic nephropathy independent of glucose control. *Diabetes* 2008, 57(3), 714-23).

Regardless of the fact that the two ROCK isoforms are similar, a growing body of evidence from more recent studies with ROCK isoform transgenic animals and ROCK isoform-selective pharmacological inhibitors support the notion that ROCK1 and ROCK2 each have unique functions. Shi et al. (Shi, J., Wu, X., Surma, M., Vemula, S., Zhang, L., Yang, Y., Kapur, R., Wei, L. Distinct roles for ROCK1 and ROCK2 in the regulation of cell detachment. *Cell Death Dis.* 2013, 4(2), e483. doi: 10.1038/cddis.2013.10), using both genetic and pharmacological approaches, demonstrated that ROCK1, via regulation of MLC2 phosphorylation, is involved in destabilizing the actin cytoskeleton in fibroblasts (i.e. ROCK1 signaling is antifibrotic), whereas ROCK2, via regulation of cofilin phosphorylation, is required for stabilizing fibroblast actin cytoskeleton (i.e. ROCK2 signaling is profibrotic). Consistent with this finding, genome-wide expression profiling of fibroblasts treated with the ROCK2 selective inhibitor, KD025 (SLx-2119), revealed decreased expression of several profibrotic mRNA including that of CTGF (Boerma, M., Fu, Q., Wang, J., Loose, D. S., Bartolozzi, A., Ellis, J. L., McGonigle, S., Paradise, E., Sweetnam, P., Fink, L. M., Vozenin-Brotons, M. C., Hauer-Jensen, M. Comparative gene expression profiling in three primary human cell lines after treatment with a novel inhibitor of Rho kinase or atorvastatin. *Blood Coagul. Fibrinolysis* 2008, 19(7), 709-718). In a separate study (Zanin-Zhorov, A., Weiss, J. M., Nyuydzefe, M. S., Chen, W., Scher, J. U., Mo, R., Depoil, D., Rao, N., Liu, B., Wei, J., Lucas, S., Koslow, M., Roche, M., Schueller, O., Weiss, S., Poyurovsky, M. V., Tonra, J., Hippen, K. L., Dustin, M. L., Blazar, B. R., Liu, C. J., Waksal, S. D. Selective oral ROCK2 inhibitor down-regulates IL-21 and IL-17 secretion in human T cells via STATS-dependent mechanism. *Proc. Natl. Acad. Sci. USA.* 2014, 111(47), 16814-9), KD025 administration decreased expression of pro-inflammatory, fibrosis-linked cytokines and mitigated murine autoimmune disease. Further evidence appearing to support a driving role for ROCK2 in fibrosis, and pertinent to renal disease, is the finding that ROCK1 knockout mice were not protected against ureteral obstruction-related renal fibrosis at either the early (day 5) or late (day 10) disease stage as determined by histology and expression of both mRNA and protein levels of αSMA, collagen types I and III and fibronectin (Fu, P., Liu, F., Su, S., Wang, W., Huang, X. R., Entman, M. L., Schwartz, R. J., Wei, L., Lan, H. Y. Signaling mechanism of renal fibrosis in unilateral ureteral obstructive kidney disease in ROCK1 knockout mice. *J. Am. Soc. Nephrol.* 2006, 17(11), 3105-14). Although Baba et al. (Baba, I., Egi, Y., Suzuki, K. Partial deletion of the ROCK2 protein fails to reduce renal fibrosis in a unilateral ureteral obstruction model in mice. *Mol. Med. Rep.* 2016, 13(1), 231-6), demonstrated that half-deletion of ROCK2 also did not prevent UUO-induced renal fibrosis, the discrepancy regarding these data and the one published by Shi et al. (Shi, J., Wu, X., Surma, M., Vemula, S., Zhang, L., Yang, Y., Kapur, R., Wei, L. Distinct roles for ROCK1 and ROCK2 in the regulation of cell detachment. *Cell Death Dis.* 2013, 4(2), e483. doi: 10.1038/cddis.2013.10), could be attributed to different strain and incomplete genetic ablation (homozygous vs heterozygous) of the ROCK2 isozyme.

Efficacy aside, need for use of an isoform-selective approach derives from the perspective of drug safety. Since ROCK plays a central role in the organization of the actin cytoskeleton, it might be anticipated that (unnecessary) inhibition of both its isoforms in a chronic setting such as chronic kidney disease (CKD) could cause severe adverse events. Indeed, systemic inhibition of ROCK does bear the risk of significant hypotension and such a strategy needs to be evaluated in terms of risk to benefit ratio (www.hsric.nihr.ac.uk/topics/netarsudil-for-open-angle-glaucoma-or-ocular-hypertension/; //en.wikipedia.org/wiki/Fasudil). For diseases such as glaucoma, which is amenable to local treatment, ROCK isoform selectivity is not mandated and ROCK1/2 dual inhibitors such as netarsudil are dosed into the eye via the intravitreous or intracameral routes (www.hsric.nihr.ac.uk/topics/netarsudil-for-open-angle-glaucoma-or-ocular-hypertension/) Furthermore, drug load in glaucoma is small. With hyperacute indications such as cerebral vasospasm, dosing with fasudil (en.wikipedia.org/wiki/Fasudil) might not pose a significant risk, albeit its use remains to be approved in the United States. Finally, in contrast to use of ROCK1/2 dual inhibitors, the ROCK2-selective inhibitor KD025 has been found to have no hemodynamic or other side effects over 12-16 weeks of dosing in healthy volunteers and patients (clinicaltrials.gov/ct2/results?term=KD025&Search=Search).

In certain embodiments, the present invention is directed toward the identification of small organic molecules that exhibit ROCK1, ROCK2, or ROCK1/2 inhibitory activities and are thus useful in the treatment or prevention of conditions or diseases in which inhibition of ROCK1, ROCK2, or ROCK1/2 is desirable.

All citations in the present application are incorporated herein by reference in their entireties. The citation of any reference herein should not be construed as an admission that such reference is available as "Prior Art" to the instant application.

SUMMARY OF THE INVENTION

As discussed above, there remains a need for the development of novel therapeutics that are capable of inhibiting ROCK1, ROCK2, or ROCK1/2 activities.

In general, inventive compounds have the structure:

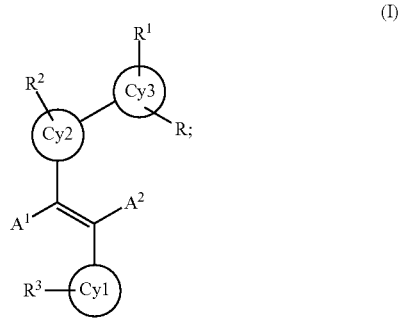

or a pharmaceutically acceptable salt thereof, wherein,

Cy1, Cy2, and Cy3 each independently represents an aryl or heteroaryl, which is optionally fused with a 3-8 membered cycloalkyl, 3-8 membered heterocycloalkyl, 6-membered aryl, or 5-6 membered heteroaryl;

$R^1$, $R^2$, and $R^3$ each independently represent one, two, three, or four same or different substituents selected from hydrogen, deuterium, halo, —CN, —$NO_2$, or an optionally substituted aliphatic, alicyclic, heteroaliphatic, heterocyclic, aromatic, heteroaromatic, —$OR^a$, —$NR^bR^c$, —$S(=O)_wR^d$, —O—$S(=O)_wR^d$, —$S(=O)_wNR^eR^f$, —$C(=O)R^g$, —$CO_2R^h$, —$CONR^iR^j$, —$NR^kCONR^lR^m$, —$OCONR^nR^o$, or —$NR^pCO_2R^q$;

R is an optionally substituted heterocyclic, aromatic, or heteroaromatic; wherein, the optional substituents are selected from hydrogen, deuterium, halo, —CN, —$NO_2$, aliphatic, alicyclic, heteroaliphatic, heterocyclic, aromatic, heteroaromatic, —$OR^a$, —$NR^bR^c$, —$S(=O)_wR^d$, —O—S$(=O)_wR^d$, —$S(=O)_wNR^eR^f$, —$C(=O)R^g$, —$CO_2R^h$, —$CONR^iR^j$, —$NR^kCONR^lR^m$, —$OCONR^nR^o$, or —$NR^kCO_2R^p$;

$R^a$, $R^b$, $R^c$, $R^d$, $R^e$, $R^f$, $R^g$, $R^h$, $R^i$, $R^{=j}i$, $R^k$, $R^l$, $R^m$, $R^n$, $R^o$, $R^p$ and $R^q$, for each occurrence, is independently selected from hydrogen, deuterium, halo, —CN, —$NO_2$, an optionally substituted aliphatic, alicyclic, heteroaliphatic, heterocyclic, aromatic, or heteroaromatic; wherein, the optional substituents are selected from hydrogen, deuterium, halo, —CN, —$NO_2$, aliphatic, alicyclic, heteroaliphatic, heterocyclic, aromatic, heteroaromatic, —$OR^{aa}$, —$NR^{bb}R^{cc}$, —$S(=O)_wR^{dd}$, —$S(=O)_wNR^{ee}R^{ff}$, —$C(=O)R^{gg}$, —$CO_2R^{hh}$, —$CONR^{ii}R^{jj}$, —$NR^{kk}CONR^{ll}R^{mm}$, —$OCONR^{nn}R^{oo}$, or —$NR^{kk}CO_2R^{pp}$; or $R^b$ and $R^c$, $R^e$ and $R^f$, $R^i$ and $R^j$, $R^l$ and $R^m$, or $R^n$ and $R^o$, when attached to the same nitrogen, may optionally form a heterocyclic ring, optionally containing 1-5 additional heteroatoms selected from O, $S(O)_w$, or N as the ring atoms, and may be optionally substituted with one or more hydrogen, deuterium, halo, —CN, —$NO_2$, aliphatic, alicyclic, heteroaliphatic, heterocyclic, aromatic, or heteroaromatic;

$R^{aa}$, $R^{bb}$, $R^{cc}$, $R^{dd}$, $R^{ee}$, $R^{ff}$, $R^{gg}$, $R^{hh}$, $R^{ii}$, $R^{jj}$, $R^{kk}$, $R^{ll}$, $R^{mm}$, $R^{nn}$, $R^{oo}$, and $R^{pp}$, for each occurrence, is independently selected from hydrogen, deuterium, halo, —CN, —$NO_2$, —OH, —$CH_2F$, —$CHF_2$, —$CF_3$, —$OCH_3$, —$OCH_2F$, —$OCHF_2$, —$OCF_3$, —$NH_2$, —$NHCH_3$, —$N(CH_3)_2$, —$CO_2H$, —SH, —$S(O)_wCH_3$, or an aliphatic, alicyclic, heteroaliphatic, heterocyclic, aromatic, or heteroaromatic;

w is 0, 1, or 2; and $A^1$ and $A^2$ are each independently selected from hydrogen, deuterium, halo, —CN, —$NO_2$, or an optionally substituted aliphatic, alicyclic, heteroaliphatic, heterocyclic, aromatic, or heteroaromatic; wherein, the optional substituents are selected from hydrogen, deuterium, halo, —CN, —$NO_2$, —$CH_2F$, —$CHF_2$, —$CF_3$, —$OCH_2F$, —$OCHF_2$, —$OCF_3$, aliphatic, alicyclic, heteroaliphatic, heterocyclic, aromatic, or heteroaromatic.

In one embodiment, the structure of the compound is formula Ia:

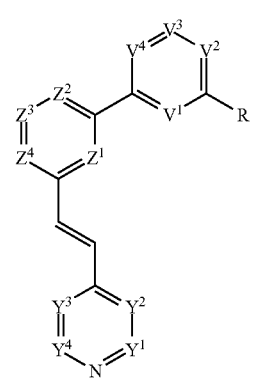

wherein V1, $V^2$, $V^3$ and $V^4$ are each independently N or C—$R^1$, wherein two $R^1$ groups on adjacent carbon atoms together with the carbons they are attached to may optionally form a 3-7 membered aromatic, heteroaromatic, or heterocyclic ring, optionally containing 1-5 additional heteroatoms selected from O, $S(O)_w$, or N as the ring atoms, and may be optionally substituted with one or more hydrogen, deuterium, halo, —CN, —NO$_2$, —OH, —CH$_2$F, —CHF$_2$, —CF$_3$, —OCH$_3$, —OCH$_2$F, —OCHF$_2$, —OCF$_3$, —NH$_2$, —NHCH$_3$, —N(CH$_3$)$_2$, —CO$_2$H, —SH, —S(O)$_w$CH$_3$, or an aliphatic, alicyclic, heteroaliphatic, heterocyclic, aromatic, or heteroaromatic;

Z$^1$, Z$^2$, Z$^3$ and Z$^4$ are each independently N or C—R$^2$, wherein two R$^2$ groups on adjacent carbon atoms together with the carbons they are attached to may optionally form a 3-7 membered aromatic, heteroaromatic, or heterocyclic ring, optionally containing 1-5 additional heteroatoms selected from O, S(O)$_w$, or N as the ring atoms, and may be optionally substituted with one or more hydrogen, deuterium, halo, —CN, —NO$_2$, —OH, —CH$_2$F, —CHF$_2$, —CF$_3$, —OCH$_3$, —OCH$_2$F, —OCHF$_2$, —OCF$_3$, —NH$_2$, —NHCH$_3$, —N(CH$_3$)$_2$, —CO$_2$H, —SH, —S(O)$_w$CH$_3$, or an aliphatic, alicyclic, heteroaliphatic, heterocyclic, aromatic, or heteroaromatic; and Y$^1$, Y$^2$, Y$^3$ and Y$^4$ are each independently N or C—R$^3$, wherein two R$^3$ groups on adjacent carbon atoms together with the carbons they are attached to may optionally form a 3-7 membered aromatic, heteroaromatic, or heterocyclic ring. The said ring may optionally contain 1-5 additional heteroatoms selected from O, S(O)$_w$, or N as the ring atoms, and may be optionally substituted; wherein, the optional substituents are selected from hydrogen, deuterium, halo, —CN, —NO$_2$, —OH, —CH$_2$F, —CHF$_2$, —CF$_3$, —OCH$_3$, —OCH$_2$F, —OCHF$_2$, —OCF$_3$, —NH$_2$, —NHCH$_3$, —N(CH$_3$)$_2$, —CO$_2$H, —SH, —S(O)$_w$CH$_3$, or an aliphatic, alicyclic, heteroaliphatic, heterocyclic, aromatic, or heteroaromatic; and wherein all other substituents are as defined in formula I.

In one embodiment, the structure of the compound is formula Ib:

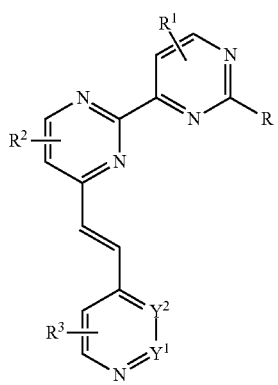

Ib wherein Y$^1$ and Y$^2$ are each independently N or C—R$^3$, wherein two R$^3$ groups together with the carbons they are attached to may optionally form a 3-7 membered aromatic, heteroaromatic, or heterocyclic ring, optionally contain 1-5 additional heteroatoms selected from O, S(O)$_w$, or N as the ring atoms, and may be optionally substituted with one or more hydrogen, deuterium, halo, —CN, —NO$_2$, —OH, —CH$_2$F, —CHF$_2$, —CF$_3$, —OCH$_3$, —OCH$_2$F, —OCHF$_2$, —OCF$_3$, —NH$_2$, —NHCH$_3$, —N(CH$_3$)$_2$, —CO$_2$H, —SH, —S(O)$_w$CH$_3$, or an aliphatic, alicyclic, heteroaliphatic, heterocyclic, aromatic, or heteroaromatic; and wherein all other substituents are as defined in formula I.

In one embodiment, the structure of the compound is formula Ic:

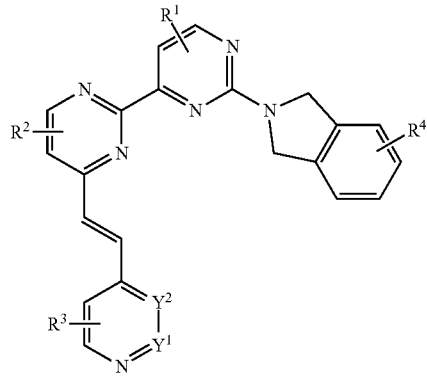

Ic wherein R$^4$ represents one, two, three, or four substituents independently selected from hydrogen, deuterium, halo, —CN, —NO$_2$, aliphatic, alicyclic, heteroaliphatic, heterocyclic, aromatic, heteroaromatic, —OR$^a$, —NR$^b$R$^c$, —S(=O)$_w$R$^d$, —O—S(=O)$_w$R$^d$, —S(=O)$_w$NR$^e$R$^f$, —C(=O)R$^g$, —CO$_2$R$^h$, —CONR$^i$R$^j$, —NR$^k$CONR$^l$R$^m$, —OCONR$^n$R$^o$, or —NR$^k$CO$_2$R$^p$; and and wherein all other substituents are as defined in formula I.

In another aspect, the invention provides compositions including pharmaceutical compositions of any of the compounds disclosed herein. Pharmaceutical compositions in one embodiment may comprise one or more compounds of the invention, and a carrier, diluent or excipient.

In another aspect, the invention provides methods for the use of any of the compounds disclosed herein for inhibiting ROCK1, ROCK2, or ROCK1/2 activities in a patient or in a biological sample. In one embodiment the compounds of the invention have antifibrotic activities. The compounds and pharmaceutical compositions of the invention have properties of inhibiting ROCK1, ROCK2, or ROCK1/2 activities and are useful in the treatment of any disease, disorder or condition in which prophylactic or therapeutic administration of ROCK1, ROCK2, or ROCK1/2 inhibitors would be useful.

In another aspect, the invention provides methods for the use of any of the compounds disclosed herein for treating or lessening the severity of a disease or condition associated with ROCK1, ROCK2, or ROCK1/2 activity. In certain embodiments, the method is for treating or lessening the severity of a disease or condition selected from fibrotic liver disease, hepatic ischemia-reperfusion injury, cerebral infarction, ischemic heart disease, renal disease or lung (pulmonary) fibrosis. In certain embodiments, the method is for treating or lessening the severity of a disease or condition selected from liver fibrosis associated with hepatitis C, hepatitis B, delta hepatitis, chronic alcoholism, non-alcoholic steatohepatitis, extrahepatic obstructions (stones in the bile duct), cholangiopathies (primary biliary cirrhosis and sclerosing cholangitis), autoimmune liver disease, and inherited metabolic disorders (Wilson's disease, hemochromatosis, and alpha-1 antitrypsin deficiency); damaged and/or ischemic organs, transplants or grafts; ischemia/reperfusion injury; stroke; cerebrovascular disease; myocardial ischemia; atherosclerosis; renal failure; renal fibrosis or idiopathic pulmonary fibrosis. In certain exemplary embodiments, the method is for the treatment of wounds for acceleration of healing; vascularization of a damaged and/or ischemic organ, transplant or graft; amelioration of ischemia/reperfusion injury in the brain, heart, liver, kidney, and other tissues and organs; normalization of myocardial perfusion as a consequence of chronic cardiac ischemia or myocardial infarction; development or augmentation of collateral vessel development after vascular occlusion or to ischemic tissues or organs; fibrotic diseases; hepatic disease including fibrosis and cirrhosis; lung fibrosis; radiocontrast nephropathy; fibrosis secondary to renal obstruction; renal trauma and transplantation; renal failure secondary to chronic diabetes and/or hypertension; and/or diabetes mellitus.

These and other aspects of the invention will be apparent from the brief description of the drawing and detailed description of the invention, below.

BRIEF DESCRIPTIONS OF THE DRAWINGS

Figure 4:
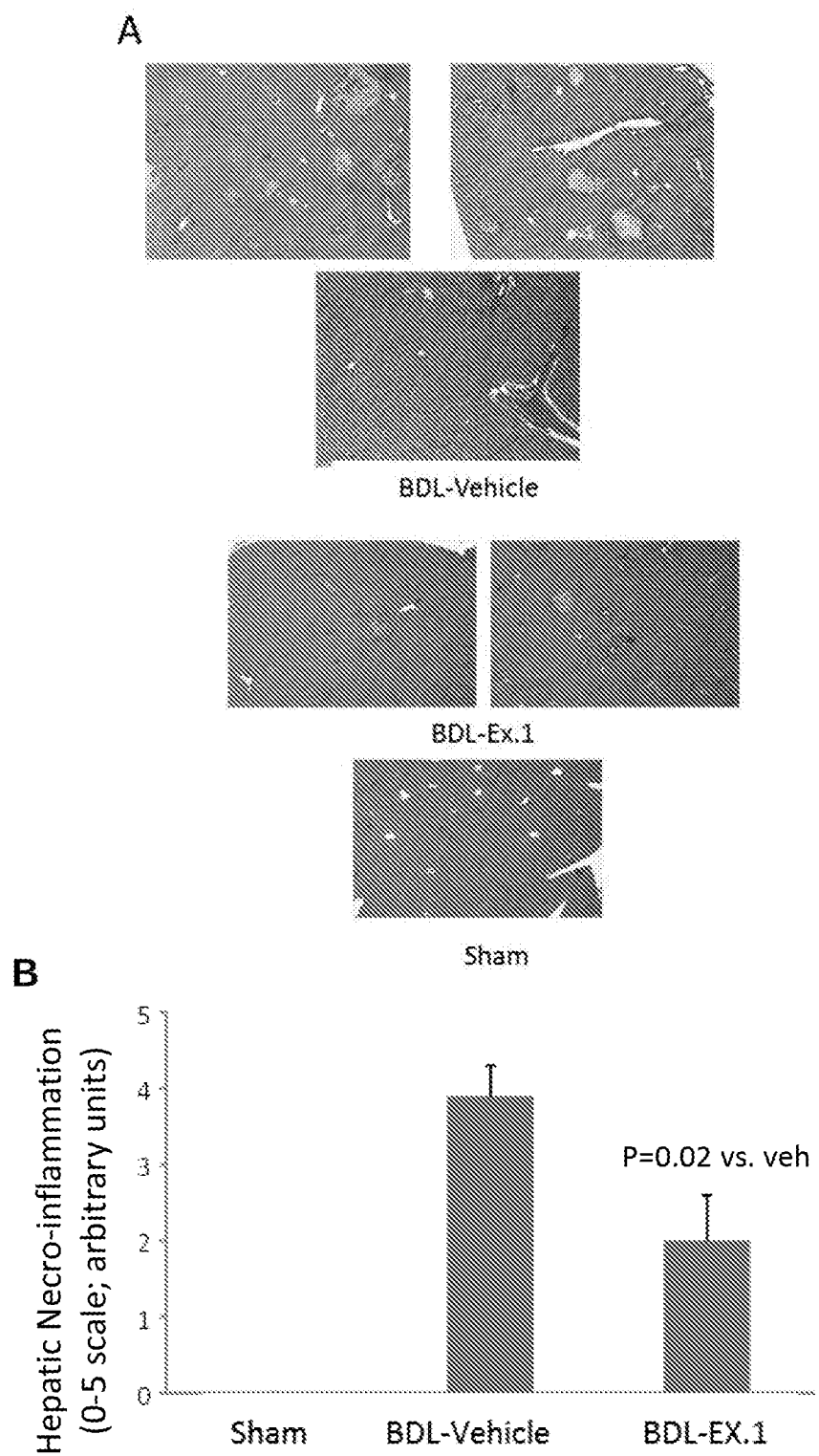

FIG. 4 A-B shows the effect of a compound of the invention on hepatic necro-inflammation, in histologic sections (A) and by scoring (B).

DEFINITIONS

The term "aliphatic", as used herein, includes both saturated and unsaturated, straight chain (i.e., unbranched) or branched aliphatic hydrocarbons, which are optionally substituted with one or more functional groups. As will be appreciated by one of ordinary skill in the art, "aliphatic" is intended herein to include, but is not limited to, alkyl, alkenyl, or alkynyl moieties. Thus, as used herein, the term "alkyl" includes straight and branched alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (substituted, unsubstituted, branched or unbranched) having 1-6 carbon atoms. "Lower alkenyl" and "lower alkynyl" respectively include corresponding 1-6 carbon moieties.

In certain embodiments, the alkyl, alkenyl and alkynyl groups employed in the invention contain 1-20; 2-20; 3-20; 4-20; 5-20; 6-20; 7-20 or 8-20 aliphatic carbon atoms. In certain other embodiments, the alkyl, alkenyl, and alkynyl groups employed in the invention contain 1-10; 2-10; 3-10; 4-10; 5-10; 6-10; 7-10 or 8-10 aliphatic carbon atoms. In yet other embodiments, the alkyl, alkenyl, and alkynyl groups employed in the invention contain 1-8; 2-8; 3-8; 4-8; 5-8; 6-20 or 7-8 aliphatic carbon atoms. In still other embodiments, the alkyl, alkenyl, and alkynyl groups employed in the invention contain 1-6; 2-6; 3-6; 4-6 or 5-6 aliphatic carbon atoms. In yet other embodiments, the alkyl, alkenyl, and alkynyl groups employed in the invention contain 1-4; 2-4 or 3-4 carbon atoms. Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "alicyclic", as used herein, refers to compounds which combine the properties of aliphatic and cyclic compounds and include but are not limited to monocyclic, or polycyclic aliphatic hydrocarbons and bridged cycloalkyl compounds, which are optionally substituted with one or more functional groups. As will be appreciated by one of ordinary skill in the art, "alicyclic" is intended herein to include, but is not limited to, cycloalkyl, cycloalkenyl, and cycloalkynyl moieties, which are optionally substituted with one or more functional groups. Illustrative alicyclic groups thus include, but are not limited to, for example, cyclopropyl, —CH$_2$-cyclopropyl, cyclobutyl, —CH$_2$-cyclobutyl, cyclopentyl, —CH$_2$-cyclopentyl, cyclohexyl, —CH$_2$-cyclohexyl, cyclohexenylethyl, cyclohexanylethyl, norbornyl moieties and the like, which again, may bear one or more substituents.

The term "alkoxy", "alkoxyl", "alkyloxy", or "alkyloxyl", as used herein refers to a saturated (i.e., O-alkyl) or unsaturated (i.e., O-alkenyl and O-alkynyl) group attached to the parent molecular moiety through an oxygen atom. In certain embodiments, the alkyl group contains 1-20; 2-20; 3-20; 4-20; 5-20; 6-20; 7-20 or 8-20 aliphatic carbon atoms. In certain other embodiments, the alkyl group contains 1-10; 2-10; 3-10; 4-10; 5-10; 6-10; 7-10 or 8-10 aliphatic carbon atoms. In yet other embodiments, the alkyl, alkenyl, and alkynyl groups employed in the invention contain 1-8; 2-8; 3-8; 4-8; 5-8; 6-20 or 7-8 aliphatic carbon atoms. In still other embodiments, the alkyl group contains 1-6; 2-6; 3-6; 4-6 or 5-6 aliphatic carbon atoms. In yet other embodiments, the alkyl group contains 1-4; 2-4 or 3-4 aliphatic carbon atoms. Examples of alkoxy, include but are not limited to, methoxy, ethoxy, propoxy, isopropoxy, n-butoxy, i-butoxy, sec-butoxy, tert-butoxy, neopentoxy, n-hexoxy and the like.

The term "thioalkyl" as used herein refers to a saturated (i.e., S-alkyl) or unsaturated (i.e., S-alkenyl and S-alkynyl) group attached to the parent molecular moiety through a sulfur atom. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of thioalkyl include, but are not limited to, methylthio, ethylthio, propylthio, isopropylthio, n-butylthio, and the like.

The term "alkylamino" refers to a group having the structure —NHR' wherein R' is aliphatic or alicyclic, as defined herein. The term "aminoalkyl" refers to a group having the structure H$_2$NR'—, wherein R' is aliphatic or alicyclic, as defined herein. In certain embodiments, the aliphatic or alicyclic group contains 1-20 aliphatic carbon atoms. In certain other embodiments, the aliphatic or alicyclic group contains 1-10 aliphatic carbon atoms. In still other embodiments, the aliphatic or alicyclic group contains 1-6 aliphatic carbon atoms. In yet other embodiments, the aliphatic or alicyclic group contains 1-4 aliphatic carbon atoms. In yet other embodiments, R' is an alkyl, alkenyl, or alkynyl group containing 1-8 aliphatic carbon atoms.

Examples of alkylamino include, but are not limited to, methylamino, ethylamino, iso-propylamino and the like.

Some examples of substituents of the above-described aliphatic (and other) moieties of compounds of the invention include, but are not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(=O)R$_x$; —CO$_2$(R$_x$); —C(=O)N(R$_x$)$_2$; —OC(=O)R$_x$; —OCO$_2$R$_x$; —OC(=O)N(R$_x$)$_2$; —N(R$_x$)$_2$; —OR$_x$; —SR$_x$; —S(O)R$_x$; —S(O)$_2$R$_x$; —NR$_x$(CO)R$_x$; —N(R$_x$)CO$_2$R$_x$; —N(R$_x$)S(O)$_2$R$_x$; —N(R$_x$)C(=O)N(R$_x$)$_2$; —S(O)$_2$N(R$_x$)$_2$; wherein each occurrence of R$_x$ independently includes, but is not limited to, aliphatic, alicyclic, heteroaliphatic, heterocyclic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aryl or heteroaryl substituents described above and herein may be substituted or unsubstituted. Additional examples of generally applicable substituents are illustrated by the specific embodiments shown in the Examples that are described herein.

In general, the term "aromatic" or "aromatic moiety", as used herein, refers to a stable mono- or polycyclic, unsaturated moiety having preferably 3-14 carbon atoms, each of which may be substituted or unsubstituted. In certain embodiments, the term "aromatic moiety" refers to a planar ring having p-orbitals perpendicular to the plane of the ring at each ring atom and satisfying the Huckel rule where the number of pi electrons in the ring is (4n+2) wherein n is an integer. A mono- or polycyclic, unsaturated moiety that does not satisfy one or all of these criteria for aromaticity is defined herein as "non-aromatic", and is encompassed by the term "alicyclic".

In general, the term "heteroaromatic" or "heteroaromatic moiety", as used herein, refers to a stable mono- or polycyclic, unsaturated moiety having preferably 3-14 carbon atoms, each of which may be substituted or unsubstituted; and comprising at least one heteroatom selected from O, S and N within the ring (i.e., in place of a ring carbon atom). In certain embodiments, the term "heteroaromatic moiety" refers to a planar ring comprising at least one heteroatom, having p-orbitals perpendicular to the plane of the ring at each ring atom, and satisfying the Hückel's rule where the number of pi electrons in the ring is (4n+2) wherein n is an integer.

It will also be appreciated that aromatic and heteroaromatic moieties, as defined herein may be attached via an alkyl or heteroalkyl moiety and thus also include-(alkyl)aromatic, -(heteroalkyl)aromatic, -(heteroalkyl)heteroaromatic, and-(heteroalkyl)heteroaromatic moieties. Thus, as used herein, the phrases "aromatic or heteroaromatic moieties" and "aromatic, heteroaromatic, -(alkyl)aromatic, -(heteroalkyl)aromatic, -(heteroalkyl)heteroaromatic, and-(heteroalkyl)heteroaromatic" are interchangeable. Substituents include, but are not limited to, any of the previously mentioned substituents, i.e., the substituents recited for aliphatic moieties, or for other moieties as disclosed herein, resulting in the formation of a stable compound.

The term "aryl", as used herein, does not differ significantly from the common meaning of the term in the art, and refers to an unsaturated cyclic moiety comprising at least one aromatic ring. In certain embodiments, "aryl" refers to a mono- or bicyclic carbocyclic ring system having one or two aromatic rings including, but not limited to phenyl, naphthyl, tetrahydronaphthyl, indanyl, indenyl and the like.

The term "heteroaryl", as used herein, does not differ significantly from the common meaning of the term in the art, and refers to a cyclic aromatic radical having from five to twelve ring atoms of which one ring atom is selected from S, O and N; zero, one, two, three, four, or five ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, quinolinyl, isoquinolinyl, and the like.

It will be appreciated that aryl and heteroaryl groups (including bicyclic aryl groups) can be unsubstituted or substituted, wherein substitution includes replacement of one or more of the hydrogen atoms thereon independently with any one or more of the following moieties including, but not limited to: aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(=O)R$_x$; —CO$_2$(R$_x$); —C(=O)N(R$_x$)$_2$; —OC(=O)R$_x$; —OCO$_2$R$_x$; —OC(=O)N(R$_x$)$_2$; —N(R$_x$)$_2$; —OR$_x$; —SR$_x$; —S(O)R$_x$; —S(O)$_2$R$_x$; —NR$_x$(CO)R$_x$; —N(R$_x$)CO$_2$R$_x$; —N(R$_x$)S(O)$_2$R$_x$; —N(R$_x$)C(=O)N(R$_x$)$_2$; —S(O)$_2$N(R$_x$)$_2$; wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl, heteroaryl, -(alkyl)aryl or -(alkyl)heteroaryl substituents described above and herein may be substituted or unsubstituted. Additionally, it will be appreciated, that any two adjacent groups taken together may represent a 4, 5, 6, or 7-membered substituted or unsubstituted alicyclic or heterocyclic moiety. Additional examples of generally applicable substituents are illustrated by the specific embodiments shown in the Examples that are described herein.

The term "cycloalkyl", as used herein, refers specifically to groups having three to twelve, preferably three to ten carbon atoms. Suitable cycloalkyls include, but are not limited to cyclopropyl, cyclobutyl, cyclopentyl, cyclohexyl, cycloheptyl and the like, which, as in the case of aliphatic, alicyclic, heteroaliphatic or heterocyclic moieties, may optionally be substituted with substituents including, but not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(=O)R$_x$; —CO$_2$(R$_x$); —C(=O)N(R$_x$)$_2$; —OC(=O)R$_x$; —OCO$_2$R$_x$; —OC(=O)N(R$_x$)$_2$; —N(R$_x$)$_2$; —OR$_x$; —SR$_x$; —S(O)R$_x$; —S(O)$_2$R$_x$; —NR$_x$(CO)R$_x$; —N(R$_x$)CO$_2$R$_x$; —N(R$_x$)S(O)$_2$R$_x$; —N(R$_x$)C(=O)N(R$_x$)$_2$; —S(O)$_2$N(R$_x$)$_2$; wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described above and herein may be substituted or unsubstituted. Additional examples of generally applicable substituents are illustrated by the specific embodiments shown in the Examples that are described herein.

The term "heteroaliphatic", as used herein, refers to aliphatic moieties in which one or more carbon atoms in the main chain have been substituted with a heteroatom. Thus, a heteroaliphatic group refers to an aliphatic chain which contains one or more oxygen, sulfur, nitrogen, phosphorus or silicon atoms, e.g., in place of carbon atoms. Heteroaliphatic moieties may be linear or branched, and saturated or unsaturated. In certain embodiments, heteroaliphatic moieties are substituted by independent replacement of one or more of the hydrogen atoms thereon with one or more moieties including, but not limited to aliphatic; alicyclic; heteroaliphatic; heterocyclic; aromatic; heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(=O)R$_x$; —CO$_2$(R$_x$); —C(=O)N(R$_x$)$_2$; —OC(=O)R$_x$; —OCO$_2$R$_x$; —OC(=O)N(R$_x$)$_2$; —N(R$_x$)$_2$; —OR$_x$; —SR$_x$; —S(O)R$_x$; —S(O)$_2$R$_x$; —NR$_x$(CO)R$_x$; —N(R$_x$)CO$_2$R$_x$; —N(R$_x$)S(O)$_2$R$_x$; —N(R$_x$)C(=O)N(R$_x$)$_2$; —S(O)$_2$N(R$_x$)$_2$; wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described above and herein may be substituted or unsubstituted. Additional examples of generally applicable substituents are illustrated by the specific embodiments shown in the Examples that are described herein.

The term "heterocycloalkyl", "heterocycle" or "heterocyclic", as used herein, refers to compounds which combine the properties of heteroaliphatic and cyclic compounds and include, but are not limited to, saturated, unsaturated and partially saturated mono- or polycyclic cyclic ring systems having 5-16 atoms wherein at least one ring atom is a heteroatom selected from O, S and N (wherein the nitrogen and sulfur heteroatoms may be optionally oxidized), wherein the ring systems are optionally substituted with one or more functional groups, as defined herein. In certain embodiments, the term "heterocycloalkyl", "heterocycle" or "heterocyclic" refers to a non-aromatic or partially aromatic 5-12 membered ring or a polycyclic group wherein at least one ring atom is a heteroatom selected from O, S and N (wherein the nitrogen and sulfur heteroatoms may be optionally oxidized), including, but not limited to a bi- or tri-cyclic group, comprising fused rings having between one and four heteroatoms independently selected from O, S and N, wherein (i) each 5-membered ring has 0 to 2 double bonds, each 6-membered ring has 0 to 3 double bonds and each 7-membered ring has 0 to 3 double bonds, (ii) the nitrogen and sulfur heteroatoms may be optionally be oxidized, (iii) the nitrogen heteroatom may optionally be quaternized, and (iv) any of the above heterocyclic rings may be fused to an aryl or heteroaryl ring. Representative heterocycles include, but are not limited to, heterocycles such as furanyl, thiofuranyl, pyranyl, pyrrolyl, pyrazolyl, imidazolyl, thienyl, pyrrolidinyl, pyrazolinyl, pyrazolidinyl, imidazolinyl, imidazolidinyl, piperidinyl, piperazinyl, oxazolyl, oxazolidinyl, isooxazolyl, isoxazolidinyl, dioxazolyl, thiadiazolyl, oxadiazolyl, tetrazolyl, triazolyl, thiatriazolyl, oxatriazolyl, thiadiazolyl, oxadiazolyl, morpholinyl, thiazolyl, thiazolidinyl, isothiazolyl, isothiazolidinyl, dithiazolyl, dithiazolidinyl, tetrahydrofuryl, and benzofused derivatives thereof. In certain embodiments, a "substituted heterocycle, or heterocycloalkyl or heterocyclic" group is utilized and as used herein, refers to a heterocycle, or heterocycloalkyl or heterocyclic group, as defined above, substituted by the independent replacement of one, two or three of the hydrogen atoms thereon with but are not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(=O)R$_x$; —CO$_2$(R$_x$); —C(=O)N(R$_x$)$_2$; —OC(=O)R$_x$; —OCO$_2$R$_x$; —OC(=O)N(R$_x$)$_2$; —N(R$_x$)$_2$; —OR$_x$; —SR$_x$; —S(O)R$_x$; —S(O)$_2$R$_x$; —NR$_x$(CO)R$_x$; —N(R$_x$)CO$_2$R$_x$; —N(R$_x$)S(O)$_2$R$_x$; —N(R$_x$)C(=O)N(R$_x$)$_2$; —S(O)$_2$N(R$_x$)$_2$; wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described above and herein may be substituted or unsubstituted. Additional examples or generally applicable substituents are illustrated by the specific embodiments shown in the Examples, which are described herein.

Additionally, it will be appreciated that any of the alicyclic or heterocyclic moieties described above and herein may comprise an aryl or heteroaryl moiety fused thereto. Additional examples of generally applicable substituents are illustrated by the specific embodiments shown in the Examples that are described herein.

The terms "halo" and "halogen" as used herein refer to an atom selected from fluorine, chlorine, bromine and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "amino", as used herein, refers to a primary (—NH$_2$), secondary (—NHR$_x$), tertiary (—NR$_x$R$_y$) or quaternary (—N$^+$R$_x$R$_y$R$_z$) amine, where R$_x$, R$_y$ and R$_z$ are independently an aliphatic, alicyclic, heteroaliphatic, heterocyclic, aromatic or heteroaromatic moiety, as defined herein. Examples of amino groups include, but are not limited to, methylamino, dimethylamino, ethylamino, diethylamino, diethylaminocarbonyl, methylethylamino, iso-propylamino, piperidino, trimethylamino, and propylamino.

The term "acyl", as used herein, refers to a group having the general formula —C(=O)R, where R is an aliphatic, alicyclic, heteroaliphatic, heterocyclic, aromatic or heteroaromatic moiety, as defined herein.

The term "$C_{2-6}$alkenylidene", as used herein, refers to a substituted or unsubstituted, linear or branched unsaturated divalent radical consisting solely of carbon and hydrogen atoms, having from two to six carbon atoms, having a free valence "-" at both ends of the radical, and wherein the unsaturation is present only as double bonds and wherein a double bond can exist between the first carbon of the chain and the rest of the molecule.

As used herein, the terms "aliphatic", "heteroaliphatic", "alkyl", "alkenyl", "alkynyl", "heteroalkyl", "heteroalkenyl", "heteroalkynyl", and the like encompass substituted and unsubstituted, saturated and unsaturated, and linear and branched groups. Similarly, the terms "alicyclic", "heterocyclic", "heterocycloalkyl", "heterocycle" and the like encompass substituted and unsubstituted, and saturated and unsaturated groups. Additionally, the terms "cycloalkyl", "cycloalkenyl", "cycloalkynyl", "heterocycloalkyl", "heterocycloalkenyl", "heterocycloalkynyl", "aromatic", "heteroaromatic", "aryl", "heteroaryl" and the like encompass both substituted and unsubstituted groups.

The phrase, "pharmaceutically acceptable derivative(s)", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others pro-drugs. A pro-drug is a derivative of a compound, usually with significantly reduced pharmacological activity, which contains an additional moiety, which is susceptible to removal in vivo yielding the parent molecule as the pharmacologically active species. An example of a pro-drug is an ester, which is cleaved in vivo to yield a compound of interest. Another example is an N-methyl derivative of a compound, which is susceptible to oxidative metabolism resulting in N-demethylation, particularly on the 1 position of the 3(5)-monosubstituted pyrazole derivatives of the invention. Pro-drugs of a variety of compounds, and materials and methods for derivatizing the parent compounds to create the pro-drugs, are known and may be adapted to the present invention. Certain exemplary pharmaceutical compositions and pharmaceutically acceptable derivatives will be discussed in more detail herein below.

The term "tautomerization" refers to the phenomenon wherein a proton of one atom of a molecule shifts to another atom. See, Jerry March, Advanced Organic Chemistry: Reactions, Mechanisms and Structures, Fourth Edition, John Wiley & Sons, pages 69-74 (1992). The term "tautomer" as used herein, refers to the compounds produced by the proton shift. For example, compounds of formula A and B can exist as a tautomer as shown below:

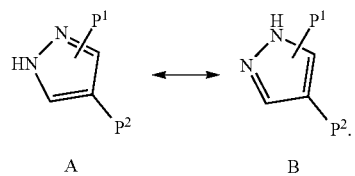

A        B

Thus, the present invention encompasses the 3-substituted pyrazole compounds described herein as well as their tautomeric 5-substituted pyrazole counterparts. Likewise, any compound shown as 5-substituted pyrazole embraces its corresponding 3-substituted tautomer. The present invention encompasses 4-substituted pyrazole compounds, in which the proton on the nitrogen can be attached to either of the two nitrogen atoms.

By the term "protecting group", as used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably nontoxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen and carbon protecting groups may be utilized. For example, in certain embodiments, as detailed herein, certain exemplary oxygen protecting groups are utilized. These oxygen protecting groups include, but are not limited to methyl ethers, substituted methyl ethers (e.g., MOM (methoxymethyl ether), MTM (methylthiomethyl ether), BOM (benzyloxymethyl ether), PMBM or MPM (p-methoxybenzyloxymethyl ether), to name a few), substituted ethyl ethers, substituted benzyl ethers, silyl ethers (e.g., TMS (trimethylsilyl ether), TES (triethylsilyl ether), TIPS (triisopropylsilyl ether), TBDMS (t-butyldimethylsilyl ether), tribenzyl silyl ether, TBDPS (t-butyldiphenyl silyl ether), to name a few), esters (e.g., formate, acetate, benzoate (Bz), trifluoroacetate, dichloroacetate, to name a few), carbonates, cyclic acetals and ketals. In certain other exemplary embodiments, nitrogen protecting groups are utilized. These nitrogen protecting groups include, but are not limited to, carbamates (including methyl, ethyl and substituted ethyl carbamates (e.g., Troc), to name a few) amides, cyclic imide derivatives, N-Alkyl and N-Aryl amines, imine derivatives, and enamine derivatives, to name a few. Certain other exemplary protecting groups are detailed herein, however, it will be appreciated that the present invention is not intended to be limited to these protecting groups; rather, a variety of additional equivalent protecting groups can be readily identified using the above criteria and utilized in the present invention. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference.

As used herein, the term "isolated" when applied to the compounds of the present invention, refers to such compounds that are (i) separated from at least some components with which they are associated in nature or when they are made and/or (ii) produced, prepared or manufactured by the hand of man.

As used herein the term "biological sample" includes, without limitation, cell cultures or extracts thereof; biopsied material obtained from an animal (e.g., mammal) or extracts thereof; and blood, saliva, urine, feces, semen, tears, or other body fluids or extracts thereof; or purified versions thereof. For example, the term "biological sample" refers to any solid or fluid sample obtained from, excreted by or secreted by any living organism, including single-celled micro-organisms (such as bacteria and yeasts) and multicellular organisms (such as plants and animals, for instance a vertebrate or a mammal, and in particular a healthy or apparently healthy human subject or a human patient affected by a condition or disease to be diagnosed or investigated). The biological sample can be in any form, including a solid material such as a tissue, cells, a cell pellet, a cell extract, cell homogenates, or cell fractions; or a biopsy, or a biological fluid. The biological fluid may be obtained from any site (e.g. blood, saliva (or a mouth wash containing buccal cells), tears, plasma, serum, urine, bile, seminal fluid, cerebrospinal fluid, amniotic fluid, peritoneal fluid, and pleural fluid, or cells therefrom, aqueous or vitreous humor, or any bodily secretion), a transudate, an exudate (e.g. fluid obtained from an abscess or any other site of infection or inflammation), or fluid obtained from a joint (e.g. a normal joint or a joint affected by disease such as rheumatoid arthritis, osteoarthritis, gout or septic arthritis). The biological sample can be obtained from any organ or tissue (including a biopsy or autopsy specimen) or may comprise cells (whether primary cells or cultured cells) or medium conditioned by any cell, tissue or organ. Biological samples may also include sections of tissues such as frozen sections taken for histological purposes. Biological samples also include mixtures of biological molecules including proteins, lipids, carbohydrates and nucleic acids generated by partial or complete fractionation of cell or tissue homogenates. Although the sample is preferably taken from a human subject, biological samples may be from any animal, plant, bacteria, virus, yeast, etc. The term animal, as used herein, refers to humans as well as non-human animals, at any stage of development, including, for example, mammals, birds, reptiles, amphibians, fish, worms and single cells. Cell cultures and live tissue samples are considered to be pluralities of animals. In certain exemplary embodiments, the non-human animal is a mammal (e.g., a rodent, a mouse, a rat, a rabbit, a monkey, a dog, a cat, a sheep, cattle, a primate, or a pig). An animal may be a transgenic animal or a human clone. If desired, the biological sample may be subjected to preliminary processing, including preliminary separation techniques.

DETAILED DESCRIPTION OF CERTAIN PREFERRED EMBODIMENTS OF THE INVENTION

The present invention provides compounds that inhibit ROCK1, ROCK2, or ROCK1/2 activities.

Compounds of this invention include those generally set forth above and described specifically herein, and are illustrated in part by the various classes, subgenera and species disclosed herein.

Additionally, the present invention provides pharmaceutically acceptable derivatives of the inventive compounds, and methods of treating a subject using these compounds, pharmaceutical compositions thereof, or either of these in combination with one or more additional therapeutic agents.

1) General Description of Compounds of the Invention

In certain embodiments, compounds of the invention include compounds of the general formula (I) as further defined below:

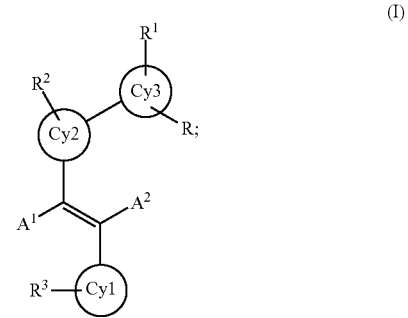

(I)

or a pharmaceutically acceptable salt thereof, wherein,

Cy1, Cy2, and Cy3 each independently represents an aryl or heteroaryl, which is optionally fused with a 3-8 membered cycloalkyl, 3-8 membered heterocycloalkyl, 6-membered aryl, or 5-6 membered heteroaryl;

$R^1$, $R^2$ and $R^3$ each independently represent one, two, three, or four same or different substituents selected from hydrogen, deuterium, halo, —CN, —NO$_2$, or an optionally substituted aliphatic, alicyclic, heteroaliphatic, heterocyclic, aromatic, heteroaromatic, —OR$^a$, —NR$^b$R$^c$, —S(=O)$_w$R$^d$, —O—S(=O)$_w$R$^d$, —S(=O)$_w$NR$^e$R$^f$, —C(=O)R$^g$, —CO$_2$R$^h$, —CONR$^i$R$^j$, —NR$^k$CONR$^l$R$^m$, —OCONR$^n$R$^o$, or —NR$^p$CO$_2$R$^q$;

R is an optionally substituted heterocyclic, aromatic, or heteroaromatic; wherein, the optional substituents are selected from hydrogen, deuterium, halo, —CN, —NO$_2$, aliphatic, alicyclic, heteroaliphatic, heterocyclic, aromatic, heteroaromatic, —OR$^a$, —NR$^b$R$^c$, —S(=O)$_w$R$^d$, —O—S(=O)$_w$R$^d$, —S(=O)$_w$NR$^e$R$^f$, —C(=O)R$^g$, —CO$_2$R$^h$, —CONR$^i$R$^j$, —NR$^k$CONR$^l$R$^m$, —OCONR$^n$R$^o$, or —NR$^k$CO$_2$R$^p$;

$R^a$, $R^b$, $R^c$, $R^d$, $R^e$, $R^f$, $R^g$, $R^h$, $R^i$, $R^j$, $R^k$, $R^l$, $R^m$, $R^n$, $R^o$, $R^p$ and $R^q$, for each occurrence, is independently selected from hydrogen, deuterium, halo, —CN, —NO$_2$, an optionally substituted aliphatic, alicyclic, heteroaliphatic, heterocyclic, aromatic, or heteroaromatic; wherein, the optional substituents are selected from hydrogen, deuterium, halo, —CN, —NO$_2$, aliphatic, alicyclic, heteroaliphatic, heterocyclic, aromatic, heteroaromatic, —OR$^{aa}$, —NR$^{bb}$R$^{cc}$, —S(=O)$_w$R$^{dd}$, —S(=O)$_w$NR$^{ee}$R$^{ff}$, —C(=O)R$^{gg}$, —CO$_2$R$^{hh}$, —CONR$^{ii}$R$^{jj}$, —NR$^{kk}$CONR$^{ll}$R$^{mm}$, —OCONR$^{nn}$R$^{oo}$, or —NR$^{kk}$CO$_2$R$^{pp}$; or $R^b$ and $R^c$, $R^e$ and $R^f$, $R^i$ and $R^j$, $R^l$ and $R^m$, or $R^n$ and $R^o$, when attached to the same nitrogen, may optionally form a heterocyclic ring, optionally containing 1-5 additional heteroatoms selected from O, S(O)$_w$, or N as the ring atoms, and may be optionally substituted with one or more hydrogen, deuterium, halo, —CN, —NO$_2$, aliphatic, alicyclic, heteroaliphatic, heterocyclic, aromatic, or heteroaromatic;

$R^{aa}$, $R^{bb}$, $R^{cc}$, $R^{dd}$, $R^{ee}$, $R^{ff}$, $R^{gg}$, $R^{hh}$, $R^{ii}$, $R^{jj}$, $R^{kk}$, $R^{ll}$, $R^{mm}$, $R^{nn}$, $R^{oo}$, and $R^{pp}$, for each occurrence, is independently selected from hydrogen, deuterium, halo, —CN, —NO$_2$, —OH, —CH$_2$F, —CHF$_2$, —CF$_3$, —OCH$_3$, —OCH$_2$F, —OCHF$_2$, —OCF$_3$, —NH$_2$, —NHCH$_3$, —N(CH$_3$)$_2$, —CO$_2$H, —SH, —S(O)$_w$CH$_3$, or an aliphatic, alicyclic, heteroaliphatic, heterocyclic, aromatic, or heteroaromatic;

w is 0, 1, or 2; and $A^1$ and $A^2$ are each independently selected from hydrogen, deuterium, halo, —CN, —NO$_2$, or an optionally substituted aliphatic, alicyclic, heteroaliphatic, heterocyclic, aromatic, or heteroaromatic; wherein, the optional substituents are selected from hydrogen, deuterium, halo, —CN, —NO$_2$, —CH$_2$F, —CHF$_2$, —CF$_3$, —OCH$_2$F, —OCHF$_2$, —OCF$_3$, aliphatic, alicyclic, heteroaliphatic, heterocyclic, aromatic, or heteroaromatic.

In one embodiment, Cy1 is a monocyclic or bicyclic or tricyclic heteroaryl. In one embodiment, Cy1 is selected from pyridinyl, pyridonyl, pyrimidinyl, pyrazinyl, pyridazinyl, triazinyl, tetrazinyl, quinolinyl, quinazolinyl, quinoxalinyl, cinnolinyl, isoquinolinyl, indolyl, aza-indolyl, pyrazolyl, imidazolyl, triazolyl, tetrazolyl, oxazolyl, thiazolyl, benzimidazolyl, indazolyl, benzoxazolyl, and benzothiazolyl. In one embodiment, Cy2 and Cy3 each independently represent a monocyclic or bicyclic aromatic or a monocyclic or bicyclic heteroaromatic. In one embodiment, Cy2 and Cy3 are independently selected from phenyl, naphthyl, pyridinyl, pyridonyl, pyrimidinyl, pyrazinyl, pyridazinyl, triazinyl, tetrazinyl, quinolinyl, quinazolinyl, quinoxalinyl, cinnolinyl, indolyl, aza-indolyl, pyrazolyl, imidazolyl, triazolyl, tetrazolyl, oxazolyl, thiazolyl, benzimidazolyl, indazolyl, benzoxazolyl, and benzothiazolyl.

In one embodiment, R is a heterocyclic group. In one embodiment, R is selected from pyrrolidinyl, indolinyl, isoindolinyl, aza-indolinyl, aza-isoindolinyl, dihydroindazolyl, tetrahydroquinolinyl, tetrahydroisoquinolinyl, aza-tetrahydroquinolinyl, and aza-tetrahydroisoquinolinyl.

In one embodiment, the structure of the compound is formula Ia:

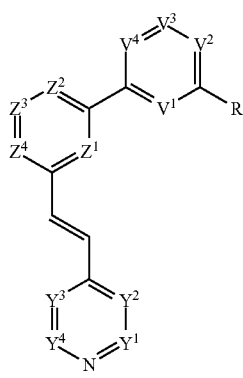

Ia wherein V$^1$, V$^2$, V$^3$ and V$^4$ are each independently N or C—R$^1$, wherein two R$^1$ groups on adjacent carbon atoms together with the carbons they are attached to may optionally form a 3-7 membered aromatic, heteroaromatic, or heterocyclic ring, optionally containing 1-5 additional heteroatoms selected from O, S(O)$_w$, or N as the ring atoms, and may be optionally substituted with one or more hydrogen, deuterium, halo, —CN, —NO$_2$, —OH, —CH$_2$F, —CHF$_2$, —CF$_3$, —OCH$_3$, —OCH$_2$F, —OCHF$_2$, —OCF$_3$, —NH$_2$, —NHCH$_3$, —N(CH$_3$)$_2$, —CO$_2$H, —SH, —S(O)$_w$CH$_3$, or an aliphatic, alicyclic, heteroaliphatic, heterocyclic, aromatic, or heteroaromatic;

Z$^1$, Z$^2$, Z$^3$ and Z$^4$ is each independently N or C—R$^2$, wherein two R$^2$ groups on adjacent carbon atoms together with the carbons they are attached to may optionally form a 3-7 membered aromatic, heteroaromatic, or heterocyclic ring, optionally containing 1-5 additional heteroatoms selected from O, S(O)$_w$, or N as the ring atoms, and may be optionally substituted with one or more hydrogen, deuterium, halo, —CN, —NO$_2$, —OH, —CH$_2$F, —CHF$_2$, —CF$_3$, —OCH$_3$, —OCH$_2$F, —OCHF$_2$, —OCF$_3$, —NH$_2$, —NHCH$_3$, —N(CH$_3$)$_2$, —CO$_2$H, —SH, —S(O),CH$_3$, or an aliphatic, alicyclic, heteroaliphatic, heterocyclic, aromatic, or heteroaromatic;

Y$^1$, Y$^2$, Y$^3$ and Y$^4$ is each independently N or C—R$^3$, wherein two R$^3$ groups on adjacent carbon atoms together with the carbons they are attached to may optionally form a 3-7 membered aromatic, heteroaromatic, or heterocyclic ring. The said ring may optionally contain 1-5 additional heteroatoms selected from O, S(O)$_w$, or N as the ring atoms, and may be optionally substituted; wherein, the optional substituents are selected from hydrogen, deuterium, halo, —CN, —NO$_2$, —OH, —CH$_2$F, —CHF$_2$, —CF$_3$, —OCH$_3$, —OCH$_2$F, —OCHF$_2$, —OCF$_3$, —NH$_2$, —NHCH$_3$, —N(CH$_3$)$_2$, —CO$_2$H, —SH, —S(O)$_w$CH$_3$, or an aliphatic, alicyclic, heteroaliphatic, heterocyclic, aromatic, or heteroaromatic; and wherein all other substituents are as defined in formula I.

In one embodiment, the structure of the compound is formula Ib:

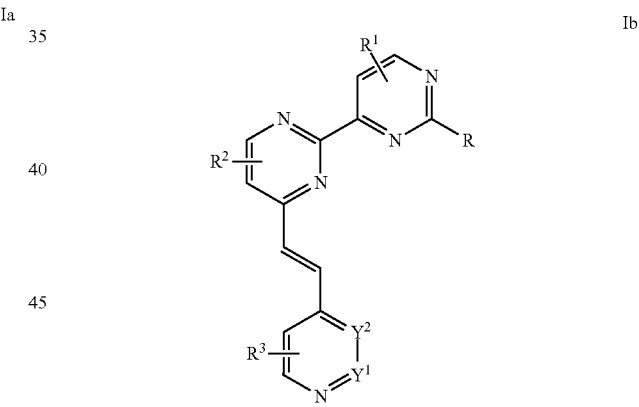

Ib wherein Y$^1$ and Y$^2$ are each independently N or C—R$^3$, wherein two R$^3$ groups together with the carbons they are attached to may optionally form a 3-7 membered aromatic, heteroaromatic, or heterocyclic ring, optionally contain 1-5 additional heteroatoms selected from O, S(O)$_w$, or N as the ring atoms, and may be optionally substituted with one or more hydrogen, deuterium, halo, —CN, —NO$_2$, —OH, —CH$_2$F, —CHF$_2$, —CF$_3$, —OCH$_3$, —OCH$_2$F, —OCHF$_2$, —OCF$_3$, —NH$_2$, —NHCH$_3$, —N(CH$_3$)$_2$, —CO$_2$H, —SH, —S(O)$_w$CH$_3$, or an aliphatic, alicyclic, heteroaliphatic, heterocyclic, aromatic, or heteroaromatic; and wherein all other substituents are as defined in formula I.

In one embodiment, the structure of the compound is formula Ic:

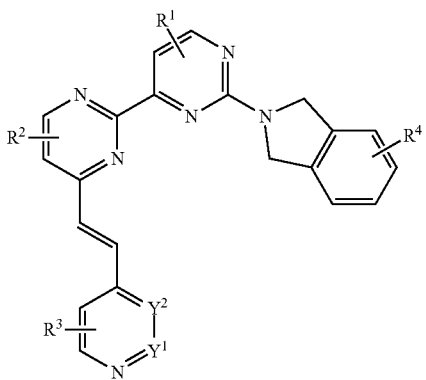

wherein R⁴ represents one, two, three, or four substituents independently selected from hydrogen, deuterium, halo, —CN, —NO₂, aliphatic, alicyclic, heteroaliphatic, heterocyclic, aromatic, heteroaromatic, —ORᵃ, —NᵇRᶜ, —S(=O)_wRᵈ, —O—S(=O)_wRᵈ, —S(=O)_wNRᵉRᶠ, —C(=O)Rᵍ, —CO₂Rʰ, —CONR'Rʲ, —NRᵏCONR'Rᵐ, —OCONR"Rᵒ, or —NRᵏCO₂Rᵖ; and wherein all other substituents are as defined in formula I.

In one embodiment, the compound is selected from the following:

(E)-5-Methoxy-2-(4-(2-(pyridine-4-yl)vinyl)-[2,4'-bipyrimidin]-2'-yl)isoindoline;
(E)-2-(4-(2-(1H-Pyrazol-3-yl)vinyl)-[2,4'-bipyrimidin]-2'-yl)-5-methoxyisoindoline;
(E)-4-(2-(2'-(5-Methoxyisoindolin-2-yl)-[2,4'-bipyrimidin]-4-yl)vinyl)quinolone;
(E)-4-(2-(2'-(5-Methoxyisoindolin-2-yl)-[2,4'-bipyrimidin]-4-yl)vinyl)-1H-pyrrolo[2,3-b]pyridine;
(E)-4-(2-(2'-(5-Methoxyisoindolin-2-yl)-[2,4'-bipyrimidin]-4-yl)vinyl)pyrimidin-2-amine;
(E)-2-(4-(2-(Pyridin-4-yl)vinyl)-[2,4'-bipyrimidin]-2'-yl)isoindolin-5-ol;
(E)-2-(4-(2-(Pyridin-4-yl)vinyl)-[2,4'-bipyrimidin]-2'-yl)isoindolin-5-yl trifluoromethanesulfonate;
(E)-2-(4-(2-(Pyridin-4-yl)vinyl)-[2,4'-bipyrimidin]-2'-yl)isoindoline-5-carbonitrile;
(E)-N,N-Dimethyl-2-((2-(4-(2-(pyridin-4-yl)vinyl)-[2,4'-bipyrimidin]-2'-yl)isoindolin-5-yl)oxy)ethanamine;
(E)-Methyl 2-((2-(4-(2-(pyridin-4-yl)vinyl)-[2,4'-bipyrimidin]-2'-yl)isoindolin-5-yl)oxy)acetate;
(E)-N-Methyl-2-((2-(4-(2-(pyridin-4-yl)vinyl)-[2,4'-bipyrimidin]-2'-yl)isoindolin-5-yl)oxy)acetamide;
(E)-N-Ethyl-2-((2-(4-(2-(pyridin-4-yl)vinyl)-[2,4'-bipyrimidin]-2'-yl)isoindolin-5-yl)oxy)acetamide;
(E)-N-Isopropyl-2-((2-(4-(2-(pyridin-4-yl)vinyl)-[2,4'-bipyrimidin]-2'-yl)isoindolin-5-yl)oxy)acetamide;
(E)-5-Fluoro-2-(4-(2-(pyridine-4-yl)vinyl)-[2,4'-bipyrimidin]-2'-yl)isoindoline;
(E)-5-Chloro-2-(4-(2-(pyridine-4-yl)vinyl)-[2,4'-bipyrimidin]-2'-yl)isoindoline;
(E)-5-Bromo-2-(4-(2-(pyridine-4-yl)vinyl)-[2,4'-bipyrimidin]-2'-yl)isoindoline;
(E)-5-Iodo-2-(4-(2-(pyridine-4-yl)vinyl)-[2,4'-bipyrimidin]-2'-yl)isoindoline;
(E)-5-Ethoxy-2-(4-(2-(pyridine-4-yl)vinyl)-[2,4'-bipyrimidin]-2'-yl)isoindoline;
(E)-5-Isopropoxy-2-(4-(2-(pyridine-4-yl)vinyl)-[2,4'-bipyrimidin]-2'-yl)isoindoline;
(E)-5-Cyclopropoxy-2-(4-(2-(pyridine-4-yl)vinyl)-[2,4'-bipyrimidin]-2'-yl)isoindoline;
(E)-5-Methyl-2-(4-(2-(pyridine-4-yl)vinyl)-[2,4'-bipyrimidin]-2'-yl)isoindoline;
(E)-5-Ethyl-2-(4-(2-(pyridine-4-yl)vinyl)-[2,4'-bipyrimidin]-2'-yl)isoindoline;
(E)-5-Cyclopropyl-2-(4-(2-(pyridine-4-yl)vinyl)-[2,4'-bipyrimidin]-2'-yl)isoindoline;
(E)-5-Amino-2-(4-(2-(pyridine-4-yl)vinyl)-[2,4'-bipyrimidin]-2'-yl)isoindoline;
(E)-5-Methylamino-2-(4-(2-(pyridine-4-yl)vinyl)-[2,4'-bipyrimidin]-2'-yl)isoindoline;
(E)-5-Dimethylamino-2-(4-(2-(pyridine-4-yl)vinyl)-[2,4'-bipyrimidin]-2'-yl)isoindoline;
(E)-5-Vinyl-2-(4-(2-(pyridine-4-yl)vinyl)-[2,4'-bipyrimidin]-2'-yl)isoindoline;
(E)-5-Propargyl-2-(4-(2-(pyridine-4-yl)vinyl)-[2,4'-bipyrimidin]-2'-yl)isoindoline;
N-Methyl-2-[4-[4-[(E)-2-(4-pyridyl)vinyl]pyrimidin-2-yl]pyrimidin-2-yl]isoindoline-5-carboxamide;
N-Ethyl-2-[4-[4-[(E)-2-(4-pyridyl)vinyl]pyrimidin-2-yl]pyrimidin-2-yl]isoindoline-5-carboxamide;
N-Isopropyl-2-[4-[4-[(E)-2-(4-pyridyl)vinyl]pyrimidin-2-yl]pyrimidin-2-yl]isoindoline-5-carboxamide;
N-Cyclopropyl-2-[4-[4-[(E)-2-(4-pyridyl)vinyl]pyrimidin-2-yl]pyrimidin-2-yl]isoindoline-5-carboxamide;
N-(tert-Butyl)-2-[4-[4-[(E)-2-(4-pyridyl)vinyl]pyrimidin-2-yl]pyrimidin-2-yl]isoindoline-5-carboxamide;
N',N'-Dimethyl-N-[2-[4-[4-[(E)-2-(4-pyridyl)vinyl]pyrimidin-2-yl]pyrimidin-2-yl]isoindolin-5-yl]ethane-1,2-diamine;
N',N'-Dimethyl-N-[2-[4-[4-[(E)-2-(4-pyridyl)vinyl]pyrimidin-2-yl]pyrimidin-2-yl]isoindolin-5-yl]ethane-1,2-diamine;
N,N,N'-Trimethyl-N-[2-[4-[4-[(E)-2-(4-pyridyl)vinyl]pyrimidin-2-yl]pyrimidin-2-yl]isoindolin-5-yl]ethane-1,2-diamine;
4-[2-[2-[4-[4-[(E)-2-(4-Pyridyl)vinyl]pyrimidin-2-yl]pyrimidin-2-yl]isoindolin-5-yl]oxyethyl]morpholine;
5-[2-(4-Methylpiperazin-1-yl)ethoxy]-2-[4-[4-[(E)-2-(4-pyridyl)vinyl]pyrimidin-2-yl]pyrimidin-2-yl]isoindoline;
4-[2-[4-[4-[(E)-2-(4-Pyridyl)vinyl]pyrimidin-2-yl]pyrimidin-2-yl]isoindolin-5-yl]morpholine;
5-(4-Methylpiperazin-1-yl)-2-[4-[4-[(E)-2-(4-pyridyl)vinyl]pyrimidin-2-yl]pyrimidin-2-yl]isoindoline;
5-(1-Methylpyrazol-4-yl)-2-[4-[4-[(E)-2-(4-pyridyl)vinyl]pyrimidin-2-yl]pyrimidin-2-yl]isoindoline;
5-Phenyl-2-[4-[4-[(E)-2-(4-pyridyl)vinyl]pyrimidin-2-yl]pyrimidin-2-yl]isoindoline;
4-[(E)-2-[2-[2-(5-Methoxyisoindolin-2-yl)pyrimidin-4-yl]pyrimidin-4-yl]vinyl]pyridin-2-amine;
4-[(E)-2-[2-[2-(5-Fluoroisoindolin-2-yl)pyrimidin-4-yl]pyrimidin-4-yl]vinyl]pyridin-2-amine;
4-[(E)-2-[2-[2-(5-Chloroisoindolin-2-yl)pyrimidin-4-yl]pyrimidin-4-yl]vinyl]pyridin-2-amine;
4-[(E)-2-[2-[2-(5-Bromoisoindolin-2-yl)pyrimidin-4-yl]pyrimidin-4-yl]vinyl]pyridin-2-amine;
2-[4-[4-[(E)-2-(2-Amino-4-pyridyl)vinyl]pyrimidin-2-yl]pyrimidin-2-yl]isoindoline-5-carbonitrile;
4-[(E)-2-[2-[2-[5-(4-Methylpiperazin-1-yl)isoindolin-2-yl]pyrimidin-4-yl]pyrimidin-4-yl]vinyl]pyridin-2-amine;
4-[(E)-2-[2-[2-(5-Morpholinoisoindolin-2-yl)pyrimidin-4-yl]pyrimidin-4-yl]vinyl]pyridin-2-amine;
2-[4-[4-[(E)-2-(2-Amino-4-pyridyl)vinyl]pyrimidin-2-yl]pyrimidin-2-yl]-N-methyl-isoindoline-5-carboxamide;
2-[4-[4-[(E)-2-(2-Amino-4-pyridyl)vinyl]pyrimidin-2-yl]pyrimidin-2-yl]-N-ethyl-isoindoline-5-carboxamide;

2-[4-[4-[(E)-2-(2-Amino-4-pyridyl)vinyl]pyrimidin-2-yl]pyrimidin-2-yl]-N-isopropyl-isoindoline-5-carboxamide;

2-[4-[4-[(E)-2-(2-Amino-4-pyridyl)vinyl]pyrimidin-2-yl]pyrimidin-2-yl]-N-methyl-isoindoline-5-carboxamide;

4-[(E)-2-[2-[2-[5-[2-(Dimethylamino)ethoxy]isoindolin-2-yl]pyrimidin-4-yl]pyrimidin-4-yl]vinyl]pyridin-2-amine; and 4-[(E)-2-[2-[2-[5-(1-Methylpyrazol-4-yl)isoindolin-2-yl]pyrimidin-4-yl]pyrimidin-4-yl]vinyl]pyridin-2-amine.

In one embodiment, a compound of formula Ic is selected from among:

(E)-5-Methoxy-2-(4-(2-(pyridine-4-yl)vinyl)-[2,4'-bipyrimidin]-2'-yl)isoindoline;

(E)-2-(4-(2-(1H-Pyrazol-3-yl)vinyl)-[2,4'-bipyrimidin]-2'-yl)-5-methoxyisoindoline;

(E)-4-(2-(2'-(5-Methoxyisoindolin-2-yl)-[2,4'-bipyrimidin]-4-yl)vinyl)quinolone;

(E)-4-(2-(2'-(5-Methoxyisoindolin-2-yl)-[2,4'-bipyrimidin]-4-yl)vinyl)-1H-pyrrolo[2,3-b]pyridine;

(E)-4-(2-(2'-(5-Methoxyisoindolin-2-yl)-[2,4'-bipyrimidin]-4-yl)vinyl)pyrimidin-2-amine;

(E)-2-(4-(2-(Pyridin-4-yl)vinyl)-[2,4'-bipyrimidin]-2'-yl)isoindolin-5-ol;

(E)-2-(4-(2-(Pyridin-4-yl)vinyl)-[2,4'-bipyrimidin]-2'-yl)isoindolin-5-yl trifluoromethanesulfonate;

(E)-2-(4-(2-(Pyridin-4-yl)vinyl)-[2,4'-bipyrimidin]-2'-yl)isoindoline-5-carbonitrile;

(E)-N,N-Dimethyl-2-((2-(4-(2-(pyridin-4-yl)vinyl)-[2,4'-bipyrimidin]-2'-yl)isoindolin-5-yl)oxy)ethanamine;

(E)-Methyl 2-((2-(4-(2-(pyridin-4-yl)vinyl)-[2,4'-bipyrimidin]-2'-yl)isoindolin-5-yl)oxy)acetate;

(E)-N-Methyl-2-((2-(4-(2-(pyridin-4-yl)vinyl)-[2,4'-bipyrimidin]-2'-yl)isoindolin-5-yl)oxy)acetamide;

(E)-N-Ethyl-2-((2-(4-(2-(pyridin-4-yl)vinyl)-[2,4'-bipyrimidin]-2'-yl)isoindolin-5-yl)oxy)acetamide;

(E)-N-Isopropyl-2-((2-(4-(2-(pyridin-4-yl)vinyl)-[2,4'-bipyrimidin]-2'-yl)isoindolin-5-yl)oxy)acetamide; and (E)-5-Fluoro-2-(4-(2-(pyridine-4-yl)vinyl)-[2,4'-bipyrimidin]-2'-yl)isoindoline.

In one embodiment, a pharmaceutical composition comprising one or more compound of any one of the foregoing formulas, and a pharmaceutically acceptable carrier, excipient or diluent.

In one embodiment, the compound of the invention has ROCK1, ROCK2, or ROCK1/2 inhibitory activities. In one embodiment, the compound has antifibrotic activity.

In one embodiment, a method of modulating ROCK1, ROCK2, or ROCK1/2 activities in a patient or in a biological sample is provided, which method comprises administering to said patient, or contacting said biological sample with a composition as described above or any compounds as described herein.

In one embodiment, a method is provided for treating a condition, disease or disorder in which ROCK1, ROCK2, or ROCK1/2 plays a role. In one embodiment, the method is for treating or lessening the severity of a disease or condition selected from renal fibrosis, fibrotic liver disease, hepatic ischemia-reperfusion injury, cerebral infarction, ischemic heart disease, renal disease or lung (pulmonary) fibrosis. In one embodiment, the method is for treating or lessening the severity of a disease or condition selected from liver fibrosis associated with hepatitis C, hepatitis B, delta hepatitis, chronic alcoholism, non-alcoholic steatohepatitis, extrahepatic obstructions (stones in the bile duct), cholangiopathies (primary biliary cirrhosis and sclerosing cholangitis), autoimmune liver disease, and inherited metabolic disorders (Wilson's disease, hemochromatosis, and alpha-1 antitrypsin deficiency); damaged and/or ischemic organs, transplants or grafts; ischemia/reperfusion injury; stroke; cerebrovascular disease; myocardial ischemia; atherosclerosis; renal failure; renal fibrosis and idiopathic pulmonary fibrosis. In one embodiment, the method is for the treatment of wounds for acceleration of healing; vascularization of a damaged and/or ischemic organ, transplant or graft; amelioration of ischemia/reperfusion injury in the brain, heart, liver, kidney, and other tissues and organs; normalization of myocardial perfusion as a consequence of chronic cardiac ischemia or myocardial infarction; development or augmentation of collateral vessel development after vascular occlusion or to ischemic tissues or organs; fibrotic diseases; hepatic disease including fibrosis and cirrhosis; lung fibrosis; radiocontrast nephropathy; fibrosis secondary to renal obstruction; renal trauma and transplantation; renal failure secondary to chronic diabetes and/or hypertension; and/or diabetes mellitus.

With regard to the foregoing compounds of the invention, a number of important subclasses of each of the foregoing formulas deserve separate mention; these subclasses include subclasses of the foregoing classes in which:

i) Cy1 is a monocyclic or bicyclic or tricyclic heteroaryl;

ii) Cy1 is pyridinyl, pyridonyl, pyrimidinyl, pyrazinyl, pyridazinyl, triazinyl, tetrazinyl, quinolinyl, quinazolinyl, quinoxalinyl, cinnolinyl, isoquinolinyl, indolyl, aza-indolyl, pyrazolyl, imidazolyl, triazolyl, tetrazolyl, oxazolyl, thiazolyl, benzimidazolyl, indazolyl, benzoxazolyl, or benzothiazolyl;

iii) Cy2 and Cy3 independently represent a monocyclic or bicyclic aromatic or a monocyclic or bicyclic heteroaromatic;

iv) Cy2 and Cy3 are independently selected from phenyl, naphthyl, pyridinyl, pyridonyl, pyrimidinyl, pyrazinyl, pyridazinyl, triazinyl, tetrazinyl, quinolinyl, quinazolinyl, quinoxalinyl, cinnolinyl, indolyl, aza-indolyl, pyrazolyl, imidazolyl, triazolyl, tetrazolyl, oxazolyl, thiazolyl, benzimidazolyl, indazolyl, benzoxazolyl, or benzothiazolyl;

v) R is a heterocyclic group;

vi) R is pyrrolidinyl, indolinyl, isoindolinyl, aza-indolinyl, aza-isoindolinyl, dihydroindazolyl, tetrahydroquinolinyl, tetrahydroisoquinolinyl, aza-tetrahydroquinolinyl, or aza-tetrahydroisoquinolinyl;

vii) Cy1 is a monocyclic or bicyclic or tricyclic heteroaryl; Cy2 and Cy3 independently represent a monocyclic or bicyclic aromatic or heteroaromatic; $R^1$ is a heteroaromatic group, which is optionally substituted by hydrogen, deuterium, halo, —CN, —NO$_2$, or an optionally substituted aliphatic, alicyclic, heteroaliphatic, heterocyclic, aromatic, and heteroaromatic, or —OR$^a$, —NR$^b$R$^c$, —S(=O)$_w$R$^d$, —O—S(=O)$_w$R$^d$, —S(=O)$_w$NR$^e$R$^f$, —C(=O)R$^g$, —CO$_2$R$^h$, —CONR$^i$R$^j$, —NR$^k$CONR$^l$R$^m$, —OCONR$^n$R$^o$, or —NR$^p$CO$_2$R$^q$; wherein, the optional substituents are selected from hydrogen, deuterium, halo, —CN, —NO$_2$, aliphatic, alicyclic, heteroaliphatic, heterocyclic, aromatic, heteroaromatic, —OR$^a$, —NR$^b$R$^c$, —S(=O)$_w$R$^d$, —O—S(=O)$_w$R$^d$, —S(=O)$_w$NR$^e$R$^f$, —C(=O)R$^g$, —CO$_2$R$^h$, —CONR$^i$R$^j$, —NR$^k$CONR$^l$R$^m$, —OCONR$^n$R$^o$, or —NR$^k$CO$_2$R$^p$; and $A^1$ and $A^2$ is each independently selected from hydrogen, deuterium, halo, —CN, or an optionally substituted aliphatic, alicyclic, heteroaliphatic, heterocyclic, aromatic, and heteroaromatic; wherein, the optional substituents are selected from hydrogen, deuterium, halo, —CN, —NO$_2$, —CH$_2$F, —CHF$_2$, —CF$_3$, —OCH$_2$F, —OCHF$_2$, or —OCF$_3$.

It will be appreciated that for each of the classes and subclasses described above and herein, any one or more occurrences of aliphatic and/or heteroaliphatic may independently be substituted or unsubstituted, linear or branched, saturated or unsaturated; any one or more occurrences of alicyclic and/or heteroalicyclic may independently be substituted or unsubstituted, saturated or unsaturated; and any one or more occurrences of aryl and/or heteroaryl may independently be substituted or unsubstituted.

The reader will also appreciate that all possible combinations of the variables described in i)- through vii) above (e.g., R, $R^1$, $R^2$, $R^3$, Cy1, Cy2, Cy3, $A^1$, and $A^2$, among others) are considered part of the invention. Thus, the invention encompasses any and all compounds of formula I generated by taking any possible permutation of variables R, $R^1$, $R^2$, $R^3$, Cy1, Cy2, Cy3, $A^1$, and $A^2$, and other variables/substituents as further defined for R, $R^1$, $R^2$, $R^3$, Cy1, Cy2, Cy3, $A^1$, and $A^2$, described in i) through vii) above.

For example, an exemplary combination of variables described in i)- through vii) above includes those compounds of Formula I wherein:

Cy1 is a monocyclic or bicyclic or tricyclic heteroaryl;

Cy2 and Cy3 are independently selected from phenyl, naphthyl, pyridinyl, pyridonyl, pyrimidinyl, pyrazinyl, pyridazinyl, triazinyl, tetrazinyl, quinolinyl, quinazolinyl, quinoxalinyl, cinnolinyl, indolyl, aza-indolyl, pyrazolyl, imidazolyl, triazolyl, tetrazolyl, oxazolyl, thiazolyl, benzimidazolyl, indazolyl, benzoxazolyl, or benzothiazolyl;

$R^1$, $R^2$, and $R^3$ each independently represents one, two, three, or four same or different substituents selected from hydrogen, deuterium, halo, —CN, —$NO_2$, or an optionally substituted aliphatic, alicyclic, heteroaliphatic, heterocyclic, aromatic, and heteroaromatic, or —$OR^a$, —$NR^bR^c$, —$S(=O)_wR^d$, —O—$S(=O)_wR^d$, —$S(=O)_wNR^eR^f$, —$C(=O)R^g$, —$CO_2R^h$, —$CONR^iR^j$, —$NR^kCONR^iR^m$, —$OCONR^nR^o$, or —$NR^pCO_2R^q$; wherein, the optional substituents are selected from hydrogen, deuterium, halo, —CN, —$NO_2$, aliphatic, alicyclic, heteroaliphatic, heterocyclic, aromatic, heteroaromatic, —OR, —$NR^bR^c$, —$S(=O)_wR^d$, —O—$S(=O)_wR^d$, —$S(=O)_wNR^eR^f$, —$C(=O)R^g$, —$CO_2R^h$, —$CONR^iR^j$, —$NR^kCONR^iR^m$, —$OCONR^nR^o$, or —$NR^kCO_2R^p$;

R is an optionally substituted heterocyclic, aromatic, or heteroaromatic; wherein, the optional substituents are selected from hydrogen, deuterium, halo, —CN, —$NO_2$, aliphatic, alicyclic, heteroaliphatic, heterocyclic, aromatic, heteroaromatic, —$OR^a$, —$NR^bR^c$, —$S(=O)_wR^d$, —O—S$(=O)_wR^d$, —$S(=O)_wNR^eR^f$, —$C(=O)R^g$, —$CO_2R^h$, —$CONR^iR^j$, —$NR^kCONR^iR^m$, —$OCONR^nR^o$, or —$NR^kCO_2R^p$;

$R^a$, $R^b$, $R^c$, $R^d$, $R^e$, $R^f$, $R^g$, $R^h$, $R^i$, $R^j$, $R^k$, $R^l$, $R^m$, $R^n$, $R^o$, $R^p$ and $R^q$, for each occurrence, is independently selected from hydrogen, deuterium, halo, —CN, —$NO_2$, an optionally substituted aliphatic, alicyclic, heteroaliphatic, heterocyclic, aromatic, or heteroaromatic; wherein, the optional substituents are selected from hydrogen, deuterium, halo, —CN, —$NO_2$, aliphatic, alicyclic, heteroaliphatic, heterocyclic, aromatic, heteroaromatic, —$OR^{aa}$, —$NR^{bb}R^{cc}$, —$S(=O)_wR^{dd}$, —$S(=O)_wNR^{ee}R^{ff}$, —$C(=O)R^{gg}$, —$CO_2R^{hh}$, —$CONR^{ii}R^{jj}$, —$NR^{kk}CONR^{ll}R^{mm}$, —$OCONR^{nn}R^{oo}$, or —$NR^{kk}CO_2R^{pp}$; or $R^b$ and $R^c$, $R^e$ and $R^f$, $R^i$ and $R^j$, $R^l$ and $R^m$, or $R^n$ and $R^o$, when attached to the same nitrogen, may optionally form a heterocyclic ring, optionally containing 1-5 additional heteroatoms selected from O, $S(O)_w$, or N as the ring atoms, and may be optionally substituted with one or more hydrogen, deuterium, halo, —CN, —$NO_2$, aliphatic, alicyclic, heteroaliphatic, heterocyclic, aromatic, or heteroaromatic;

$R^{aa}$, $R^{bb}$, $R^{cc}$, $R^{dd}$, $R^{ee}$, $R^{ff}$, $R^{gg}$, $R^{hh}$, $R^{ii}$, $R^{jj}$, $R^{kk}$, $R^{ll}$, $R^{mm}$, $R^{nn}$, $R^{oo}$, and $R^{pp}$, for each occurrence, is independently selected from hydrogen, deuterium, halo, —CN, —$NO_2$, —OH, —$CH_2F$, —$CHF_2$, —$CF_3$, —$OCH_3$, —$OCH_2F$, —$OCHF_2$, —$OCF_3$, —$NH_2$, —$NHCH_3$, —$N(CH_3)_2$, —$CO_2H$, —SH, —$S(O)_wCH_3$, or an aliphatic, alicyclic, heteroaliphatic, heterocyclic, aromatic, or heteroaromatic;

w is 0, 1, or 2;

$A^1$ and $A^2$ are each independently selected from hydrogen, deuterium, halo, —CN, —$NO_2$, or an optionally substituted aliphatic, alicyclic, heteroaliphatic, heterocyclic, aromatic, or heteroaromatic; wherein, the optional substituents are selected from hydrogen, deuterium, halo, —CN, —$NO_2$, —$CH_2F$, —$CHF_2$, —$CF_3$, —$OCH_2F$, —$OCHF_2$, —$OCF_3$, aliphatic, alicyclic, heteroaliphatic, heterocyclic, aromatic, or heteroaromatic.

It will be appreciated that each of the compounds described herein and each of the subclasses of compounds described above may be substituted as described generally herein, or may be substituted according to any one or more of the subclasses described above and herein [e.g., i)-vii)].

Some of the foregoing compounds can comprise one or more asymmetric centers, and thus can exist in various isomeric forms, e.g., stereoisomers and/or diastereomers. Thus, inventive compounds and pharmaceutical compositions thereof may be in the form of an individual enantiomer, diastereomer or geometric isomer, or may be in the form of a mixture of stereoisomers. In certain embodiments, the compounds of the invention are enantiopure compounds. In certain other embodiments, mixtures of stereoisomers or diastereomers are provided.

Furthermore, certain compounds, as described herein may have one or more double bonds that can exist as either the Z or E isomer, unless otherwise indicated. The invention additionally encompasses the compounds as individual isomers substantially free of other isomers and alternatively, as mixtures of various isomers, e.g., racemic mixtures of stereoisomers. In addition to the above-mentioned compounds per se, this invention also encompasses pharmaceutically acceptable derivatives of these compounds and compositions comprising one or more compounds of the invention and one or more pharmaceutically acceptable excipients or additives.

Compounds of the invention may be prepared by crystallization of compound of formula (I) under different conditions and may exist as one or a combination of polymorphs of compound of general formula (I) forming part of this invention. For example, different polymorphs may be identified and/or prepared using different solvents, or different mixtures of solvents for recrystallization; by performing crystallizations at different temperatures; or by using various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray difractogram and/or other techniques. Thus, the present invention encompasses inventive compounds, their derivatives, their tautomeric forms, their stereoisomers, their polymorphs, their pharmaceutically acceptable salts their pharmaceutically acceptable solvates and pharmaceutically acceptable compositions containing them. Tautomeric forms of compounds of the present invention include, for example the 3- and 5-substituted pyrazole tautomers and the 4-substituted pyrazole tautomers of any of the aforementioned disubstituted compounds of general Formula I and related formulas.

Pharmaceutical Compositions

As discussed above this invention provides novel compounds that have biological properties useful for the treatment of any of a number of conditions or diseases in which inhibiting ROCK1, ROCK2, and ROCK1/2 activities thereof have a therapeutically useful role.

Accordingly, in another aspect of the present invention, pharmaceutical compositions are provided, which comprise any one or more of the compounds described herein (or a prodrug, pharmaceutically acceptable salt or other pharmaceutically acceptable derivative thereof), and optionally comprise a pharmaceutically acceptable carrier. In certain embodiments, these compositions optionally further comprise one or more additional therapeutic agents. Alternatively, a compound of this invention may be administered to a patient in need thereof in combination with the administration of one or more other therapeutic agents. For example, additional therapeutic agents for conjoint administration or inclusion in a pharmaceutical composition with a compound of this invention may be an approved agent to treat the same or related indication, or it may be any one of a number of agents undergoing approval in the Food and Drug Administration that ultimately obtain approval for the treatment of any disorder described herein. It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or a pro-drug or other adduct or derivative of a compound of this invention which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in *J. Pharmaceutical Sciences*, 66: 1-19 (1977), incorporated herein by reference. The salts can be prepared in situ during the final isolation and purification of the compounds of the invention, or separately by reacting a free base or free acid function with a suitable reagent, as described generally below. For example, a free base function can be reacted with a suitable acid. Furthermore, where the compounds of the invention carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Additionally, as used herein, the term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

Furthermore, the term "pharmaceutically acceptable prodrugs" as used herein refers to those prodrugs of the compounds of the present invention which are, within the scope of sound medical judgment, suitable for use in contact with the issues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood, or N-demethylation of a compound of the invention where $R^1$ is methyl. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference. By way of example, N-methylated pro-drugs of the 3(5)-monosubstituted pyrazoles of the invention are embraced herein.

As described above, the pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other nontoxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut (peanut), corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension or crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include (poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose and starch. Such dosage forms may also comprise, as in normal practice, additional substances other than inert diluents, e.g., tableting lubricants and other tableting aids such as magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The present invention encompasses pharmaceutically acceptable topical formulations of inventive compounds. The term "pharmaceutically acceptable topical formulation", as used herein, means any formulation which is pharmaceutically acceptable for intradermal administration of a compound of the invention by application of the formulation to the epidermis. In certain embodiments of the invention, the topical formulation comprises a carrier system. Pharmaceutically effective carriers include, but are not limited to, solvents (e.g., alcohols, poly alcohols, water), creams, lotions, ointments, oils, plasters, liposomes, powders, emulsions, microemulsions, and buffered solutions (e.g., hypotonic or buffered saline) or any other carrier known in the art for topically administering pharmaceuticals. A more complete listing of art-known carriers is provided by reference texts that are standard in the art, for example, Remington's Pharmaceutical Sciences, 16th Edition, 1980 and 17th Edition, 1985, both published by Mack Publishing Company, Easton, Pa., the disclosures of which are incorporated herein by reference in their entireties. In certain other embodiments, the topical formulations of the invention may comprise excipients. Any pharmaceutically acceptable excipient known in the art may be used to prepare the inventive pharmaceutically acceptable topical formulations. Examples of excipients that can be included in the topical formulations of the invention include, but are not limited to, preservatives, antioxidants, moisturizers, emollients, buffering agents, solubilizing agents, other penetration agents, skin protectants, surfactants, and propellants, and/or additional therapeutic agents used in combination to the inventive compound. Suitable preservatives include, but are not limited to, alcohols, quaternary amines, organic acids, parabens, and phenols. Suitable antioxidants include, but are not limited to, ascorbic acid and its esters, sodium bisulfite, butylated hydroxytoluene, butylated hydroxyanisole, tocopherols, and chelating agents like EDTA and citric acid. Suitable moisturizers include, but are not limited to, glycerin, sorbitol, polyethylene glycols, urea, and propylene glycol. Suitable buffering agents for use with the invention include, but are not limited to, citric, hydrochloric, and lactic acid buffers. Suitable solubilizing agents include, but are not limited to, quaternary ammonium chlorides, cyclodextrins, benzyl benzoate, lecithin, and polysorbates. Suitable skin protectants that can be used in the topical formulations of the invention include, but are not limited to, vitamin E oil, allatoin, dimethicone, glycerin, petrolatum, and zinc oxide.

In certain embodiments, the pharmaceutically acceptable topical formulations of the invention comprise at least a compound of the invention and a penetration enhancing agent. The choice of topical formulation will depend or several factors, including the condition to be treated, the physicochemical characteristics of the inventive compound and other excipients present, their stability in the formulation, available manufacturing equipment, and costs constraints. As used herein the term "penetration enhancing agent" means an agent capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, Percutaneous Penetration Enhancers, Maibach H. I. and Smith H. E. (eds.), CRC Press, Inc., Boca Raton, Fla. (1995), which surveys the use and testing of various skin penetration enhancers, and Buyuktimkin et al., Chemical Means of Transdermal Drug Permeation Enhancement in Transdermal and Topical Drug Delivery Systems, Gosh T. K., Pfister W. R., Yum S. I. (Eds.), Interpharm Press Inc., Buffalo Grove, Ill. (1997). In certain exemplary embodiments, penetration agents for use with the invention include, but are not limited to, triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate) and N-methyl pyrrolidone.

In certain embodiments, the compositions may be in the form of ointments, pastes, creams, lotions, gels, powders, solutions, sprays, inhalants or patches. In certain exemplary embodiments, formulations of the compositions according to the invention are creams, which may further contain saturated or unsaturated fatty acids such as stearic acid, palmitic acid, oleic acid, palmito-oleic acid, cetyl or oleyl alcohols, stearic acid being particularly preferred. Creams of the invention may also contain a non-ionic surfactant, for example, polyoxy-40-stearate. In certain embodiments, the active component is admixed under sterile conditions with a pharmaceutically acceptable carrier and any needed preservatives or buffers as may be required. Ophthalmic formulation, eardrops, and eye drops are also contemplated as being within the scope of this invention. Formulations for intraocular administration are also included. Additionally, the present invention contemplates the use of transdermal patches, which have the added advantage of providing controlled delivery of a compound to the body. Such dosage forms are made by dissolving or dispensing the compound in the proper medium. As discussed above, penetration enhancing agents can also be used to increase the flux of the compound across the skin. The rate can be controlled by either providing a rate controlling membrane or by dispersing the compound in a polymer matrix or gel.

It will also be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another antiinflammatory agent), or they may achieve different effects (e.g., control of any adverse effects). In non-limiting examples, one or more compounds of the invention may be formulated with at least one cytokine, growth factor or other biological, such as an interferon, e.g., alpha interferon, or with at least another small molecule compound. Non-limiting examples of pharmaceutical agents that may be combined therapeutically with compounds of the invention include: antivirals and antifibrotics such as interferon alpha, combination of interferon alpha and ribavirin, Lamivudine, Adefovir dipivoxil and interferon gamma; anticoagulants such as heparin and warfarin; antiplatelets e.g., aspirin, ticlopidine and clopidogrel; other growth factors involved in regeneration, e.g., VEGF and FGF and mimetics of these growth factors; antiapoptotic agents; and motility and morphogenic agents.

In certain embodiments, the pharmaceutical compositions of the present invention further comprise one or more additional therapeutically active ingredients (e.g., antiinflammatory and/or palliative). For purposes of the invention, the term "Palliative" refers to treatment that is focused on the relief of symptoms of a disease and/or side effects of a therapeutic regimen, but is not curative. For example, palliative treatment encompasses painkillers, antinausea medications and anti-sickness drugs.

Research Uses, Clinical Uses, Pharmaceutical Uses and Methods of Treatment

Research Uses

According to the present invention, the inventive compounds may be assayed in any of the available assays known in the art for identifying compounds having the ability to modulate ROCK1, ROCK2, or ROCK1/2 activities and in particular to antagonize the activities of ROCK1, ROCK2, or ROCK1/2. For example, the assay may be cellular or non-cellular, in vivo or in vitro, high- or low-throughput format, etc.

Thus, in one aspect, compounds of this invention which are of particular interest include those inhibiting ROCK1, ROCK2, or ROCK1/2 activities.

Clinical uses of compounds with ROCK1, ROCK2, or ROCK1/2 inhibitory activities.

1. Fibrotic Liver Disease: Liver fibrosis is the scarring response of the liver to chronic liver injury; when fibrosis progresses to cirrhosis, morbid complications can develop. In fact, end-stage liver fibrosis or cirrhosis is the seventh leading cause of death in the United States, and afflicts hundreds of millions of people worldwide; deaths from end-stage liver disease in the United States are expected to triple over the next 10-15 years, mainly due to the hepatitis C epidemic 1. In addition to the hepatitis C virus, many other forms of chronic liver injury also lead to end-stage liver disease and cirrhosis, including other viruses such as hepatitis B and delta hepatitis, chronic alcoholism, non-alcoholic steatohepatitis, extrahepatic obstructions (stones in the bile duct), cholangiopathies (primary biliary cirrhosis and sclerosing cholangitis), autoimmune liver disease, and inherited metabolic disorders (Wilson's disease, hemochromatosis, and alpha-1 antitrypsin deficiency).

Treatment of liver fibrosis has focused to date on eliminating the primary injury. For extrahepatic obstructions, biliary decompression is the recommended mode of treatment whereas patients with Wilson's disease are treated with zinc acetate. In chronic hepatitis C infection, interferon has been used as antiviral therapies with limited response: ~20% when used alone or ~50% response when used in combination with ribavirin. In addition to the low-level of response, treatment with interferon with or without ribavirin is associated with numerous severe side effects including neutropenia, thrombocytopenia, anemia, depression, generalized fatigue and flu-like symptoms, which are sufficiently significant to necessitate cessation of therapy. Treatments for other chronic liver diseases such as hepatitis B, autoimmune hepatitis and Wilson's disease are also associated with many side effects, while primary biliary cirrhosis, primary sclerosing cholangitis and non-alcoholic fatty liver disease have no effective treatment other than liver transplantation.

The advantage of treating fibrosis rather than only the underlying etiology, is that antifibrotic therapies should be broadly applicable across the full spectrum of chronic liver diseases. While transplantation is currently the most effective cure for liver fibrosis, mounting evidence indicates that not only fibrosis, but even cirrhosis is reversible. Unfortunately, patients often present with advanced stages of fibrosis and cirrhosis, when many therapies such as antivirals can no longer be safely used due to their side effect profile. Such patients would benefit enormously from effective antifibrotic therapy, because attenuating or reversing fibrosis may prevent many late stage complications such as infection, asciites, and loss of liver function and preclude the need for liver transplantation. The compounds of the invention are beneficial for the treatment of the foregoing conditions, and generally are antifibrotic and/or antiapoptotic agents for this and other organ or tissues.

2. Hepatic Ischemia-Reperfusion Injury: Currently, transplantation is the most effective therapeutic strategy for liver fibrosis. However, in spite of the significant improvement in clinical outcome during the last decade, liver dysfunction or failure is still a significant clinical problem after transplantation surgery. Ischemia-reperfusion (IR) injury to the liver is a major alloantigen-independent component affecting transplantation outcome, causing up to 10% of early organ failure, and leading to the higher incidence of both acute and chronic rejection. Furthermore, given the dramatic organ shortage for transplantation, surgeons are forced to consider cadaveric or steatotic grafts or other marginal livers, which have a higher susceptibility to reperfusion injury. In addition to transplantation surgery, liver IR injury is manifested in clinical situations such as tissue resections (Pringle maneuver), and hemorrhagic shock.

The damage to the postischemic liver represents a continuum of processes that culminate in hepatocellular injury. Ischemia activates Kupffer cells, which are the main sources of vascular reactive oxygen species (ROS) formation during the initial reperfusion period. In addition to Kupffer cell-induced oxidant stress, with increasing length of the ischemic episode, intracellular generation of ROS by xanthine oxidase and in particular mitochondria may also contribute to liver dysfunction and cell injury during reperfusion. Endogenous antioxidant compounds, such as superoxide dismutase, catalase, glutathione, alphatocopherol, and beta-carotene, may all limit the effects of oxidant injury but these systems can quickly become overwhelmed by large quantities of ROS. Work by Lemasters and colleagues, has indicated that in addition to formation of ROS, intracellular calcium dyshomeostasis is a key contributor to liver IR injury. Cell death of hepatocytes and endothelial cells in this setting is characterized by swelling of cells and their organelles, release of cell contents, eosinophilia, karyolysis, and induction of inflammation, characteristic of oncotic necrosis. More recent reports indicate that liver cells also die by apoptosis, which is morphologically characterized by cell shrinkage, formation of apoptotic bodies with intact cell organelles and absence of an inflammatory response.

Indeed, minimizing the adverse effects of IR injury could significantly increase the number of patients that may successfully undergo liver transplantation. Pharmacologic interventions that reduce cell death and/or enhance organ regeneration represent a therapeutic approach to improve clinical outcome in liver transplantation, liver surgery with vascular exclusion and trauma and can therefore reduce recipient/patient morbidity and mortality. The compounds of the invention are beneficial for the treatment of the foregoing conditions.

3. Cerebral Infarction. Stroke and cerebrovascular disease are a leading cause of morbidity and mortality in the US: at least 600,000 Americans develop strokes each year, and about 160,000 of these are fatal. Research on the pathophysiological basis of stroke has produced new paradigms for prevention and treatment, but translation of these approaches into improved clinical outcomes has proved to be painfully slow. Preventive strategies focus primarily on reducing or controlling risk factors such as diabetes, hypertension, cardiovascular disease, and lifestyle; in patients with severe stenosis, carotid endarterectomy may be indicated. Cerebral angioplasty is used investigationally, but the high restenosis rates observed following coronary angioplasty suggest this approach may pose unacceptable risk for many patients. Therapeutic strategies focus primarily on acute treatment to reduce injury in the ischemic penumbra, the region of reversibly damaged tissue surrounding an infarct. Thrombolytic therapy has been shown to improve perfusion to the ischemic penumbra, but it must be administered within three hours of the onset of infarction. Several neuroprotective agents that block specific tissue responses to ischemia are promising, but none have yet been approved for clinical use. While these therapeutic approaches limit damage in the ischemic penumbra, they do not address the underlying problem of inadequate blood supply due to occluded arteries. An alternative strategy is to induce formation of collateral blood vessels in the ischemic region; this occurs naturally in chronic ischemic conditions, but stimulation of vascularization via therapeutic angiogenesis has potential therapeutic benefit.

Recent advances in imaging have confirmed the pathophysiological basis of the clinical observations of evolving stroke. Analysis of impaired cerebral blood flow (CBF) in the region of an arterial occlusion supports the hypothesis that a central region of very low CBF, the ischemic core, is irreversibly damaged, but damage in surrounding or intermixed zones where CBF is of less severely reduced, the ischemic penumbra, can be limited by timely reperfusion. Plate recently reviewed the evidence suggesting that therapeutic angiogenesis may be useful for treatment or prevention of stroke. Analysis of cerebral vasculature in stroke patients showed a strong correlation between blood vessel density and survival and a higher density of microvessels in the ischemic hemisphere compared to the contralateral region. The compounds of the invention are beneficial for the treatment of the foregoing conditions.

4. Ischemic heart disease is a leading cause of morbidity and mortality in the US, afflicting millions of Americans each year at a cost expected to exceed $300 billion/year. Numerous pharmacological and interventional approaches are being developed to improve treatment of ischemic heart disease including reduction of modifiable risk factors, improved revascularization procedures, and therapies to halt progression and/or induce regression of atherosclerosis. One of the most exciting areas of research for the treatment of myocardial ischemia is therapeutic angiogenesis. Recent studies support the concept that administration of angiogenic growth factors, either by gene transfer or as a recombinant protein, augments nutrient perfusion through neovascularization. The newly developed, supplemental collateral blood vessels constitute endogenous bypass conduits around occluded native arteries, improving perfusion to ischemic tissue. The compounds of the invention are beneficial for the treatment of the foregoing conditions.

5. Renal Disease. Chronic renal dysfunction is a progressive, degenerative disorder that ultimately results in acute renal failure and requires dialysis as an intervention, and renal transplantation as the only potential cure. Initiating conditions of renal dysfunction include ischemia, diabetes, underlying cardiovascular disease, or renal toxicity associated with certain chemotherapeutics, antibiotics, and radiocontrast agents. Most end-stage pathological changes include extensive fibrinogenesis, epithelial atrophy, and inflammatory cell infiltration into the kidneys.

Acute renal failure is often a complication of diseases including diabetes or renal ischemia, procedures such as heminephrectomy, or as a side effect of therapeutics administered to treat disease. The widely prescribed anti-tumor drug cis-diamminedichloroplatinum (cisplatin), for example, has side effects that include a high incidence of nephrotoxicity and renal dysfunction, mainly in the form of renal tubular damage that leads to impaired glomerular filtration. Administration of gentamicin, an aminoglycoside antibiotic, or cyclosporin A, a potent immunosuppressive compound, causes similar nephrotoxicity. The serious side effects of these effective drugs restrict their use. The development of agents that protect renal function and enhance renal regeneration after administration of nephrotoxic drugs will be of substantial benefit to numerous patients, especially those with malignant tumors, and may allow the maximal therapeutic potentials of these drugs to be realized. The compounds of the invention are beneficial for the treatment of the renal diseases mentioned above.

6. Lung (Pulmonary) Fibrosis. Idiopathic pulmonary fibrosis (IPF) accounts for a majority of chronic interstitial lung diseases, and has an estimated incidence rate of 10.7 cases for 100,000 per year, with an estimated mortality of 50-70%. IPF is characterized by an abnormal deposition of collagen in the lung with an unknown etiology. Although the precise sequence of the pathogenic sequelae is unknown, disease progression involves epithelial injury and activation, formation of distinctive subepithelial fibroblast/myofibroblast foci, and excessive extracellular matrix accumulation. The development of this pathological process is preceded by an inflammatory response, often dominated by macrophages and lymphocytes, which is mediated by the local release of chemoattractant factors and upregulation of cell-surface adhesion molecules. Lung injury leads to vasodilatation and leakage of plasma proteins into interstitial and alveolar spaces, as well as activation of the coagulation cascade and deposition of fibrin. Fibroblasts migrate into this provisional fibrin matrix where they synthesize extracellular matrix molecules. In non-pathogenic conditions, excess fibrin is usually degraded by plasmin, a proteinase that also has a role in the activation of matrix metalloproteinases (MMPs). Activated MMPs degrade extracellular matrix and participate in fibrin removal, resulting in the clearance of the alveolar spaces and the ultimate restoration of injured tissues. In pathological conditions, however, these processes can lead to progressive and irreversible changes in lung architecture, resulting in progressive respiratory insufficiency and an almost universally terminal outcome in a relatively short period of time. Fibrosis is the final common pathway of a variety of lung disorders, and in this context, the diagnosis of pulmonary fibrosis implies the recognition of an advanced stage in the evolution of a complex process of abnormal repair. While many studies have focused on inflammatory mechanisms for initiating the fibrotic response, the synthesis and degradation the extracellular matrix represent the central event of the disease. It is this process that presents a very attractive site of therapeutic intervention.

The course of IPF is characterized by progressive respiratory insufficiency, leading to death within 3 to 8 years from the onset of symptoms. Management of interstitial lung disease in general, and in particular idiopathic pulmonary fibrosis, is difficult, unpredictable and unsatisfactory. Attempts have been made to use antiinflammatory therapy to reverse inflammation, relief, stop disease progression and prolong survival. Corticosteroids are the most frequently used antiinflammatory agents and have been the mainstay of therapy for IPF for more than four decades, but the efficacy of this approach is unproven, and toxicities are substantial. No studies have compared differing dosages or duration of corticosteroid treatment in matched patients. Interpretation of therapy efficacy is obscured by several factors including heterogeneous patient populations, inclusion of patients with histologic entities other than usual interstitial pneumonia, lack of objective, validated endpoints, and different criteria for "response." Cytotoxic drugs such as Azathioprine and cyclophosohamide have also being used in combination with low dose oral corticosteroids. The results of such treatments vary from no improvement to significant prolongation of survival. Overall, currently available treatments for lung fibrosis are sub-optimal. Potential new therapies have emerged from the use of animal models of pulmonary fibrosis and recent advances in the cellular and molecular biology of inflammatory reactions. Such therapies involve the use of cytokines, oxidants and growth factors that are elaborated during the fibrotic reaction. Despite the use of newer strategies for treatment, the overall prognosis for patients with interstitial lung disease has had little quantifiable change, and the population survival remains unchanged for the last 30 years. Interferon gamma (IFN) may be effective in the treatment of IPF in some patients but its role is controversial. Literature indicated that IFN-gamma may be involved in small airway disease in silicotic lung. Others showed that IFN gamma mediates, bleomycin-induced pulmonary inflammation and fibrosis. The compounds of the invention are beneficial for the treatment of the foregoing condition, among other fibrotic diseases.

Exemplary Assays

Efficacy of the compounds of the invention on the aforementioned disorders and diseases or the potential to be of benefit for the prophylaxis or treatment thereof may be demonstrated in various studies, ranging from biochemical effects evaluated in vitro and effects on cells in culture, to in-vivo models of disease, wherein direct clinical manifestations of the disease can be observed and measured, or wherein early structural and/or functional events occur that are established to be involved in the initiation or progression of the disease. The positive effects of the compounds of the invention have been demonstrated in a variety of such assays and models, for a number of diseases and disorders. One skilled in the art can readily determine following the guidance described herein whether a compound of the invention useful for the purposed herein described.

As detailed in the exemplification herein, in assays to determine the ability of compounds to inhibit the activities of ROCK1, ROCK2, or ROCK1/2 measured in vitro, certain inventive compounds exhibited $IC_{50}$ values $\leq 50$ µM. In certain other embodiments, inventive compounds exhibit $IC_{50}$ values $\leq 40$ µM. In certain other embodiments, inventive compounds exhibit $IC_{50}$ values $\leq 30$ µM. In certain other embodiments, inventive compounds exhibit $IC_{50}$ values $\leq 20$ µM. In certain other embodiments, inventive compounds exhibit $IC_{50}$ values $\leq 10$ µM. In certain other embodiments, inventive compounds exhibit $IC_{50}$ values $\leq 7.5$ µM. In certain embodiments, inventive compounds exhibit $IC_{50}$ values $\leq 5$ µM. In certain other embodiments, inventive compounds exhibit $IC_{50}$ values $\leq 2.5$ µM. In certain embodiments, inventive compounds exhibit $IC_{50}$ values $\leq 1$ µM. In certain other embodiments, inventive compounds exhibit $IC_{50}$ values $\leq 750$ nM. In certain other embodiments, inventive compounds exhibit $IC_{50}$ values $\leq 500$ nM. In certain other embodiments, inventive compounds exhibit $IC_{50}$ values $\leq 250$ nM. In certain other embodiments, inventive compounds exhibit $IC_{50}$ values $\leq 100$ nM. In other embodiments, exemplary compounds exhibited $IC_{50}$ values $\leq 75$ nM. In other embodiments, exemplary compounds exhibited $IC_{50}$ values $\leq 50$ nM. In other embodiments, exemplary compounds exhibited $IC_{50}$ values $\leq 40$ nM. In other embodiments, exemplary compounds exhibited $IC_{50}$ values $\leq 30$ nM. In other embodiments, exemplary compounds exhibited $IC_{50}$ values $\leq 20$ nM. In other embodiments, exemplary compounds exhibited $IC_{50}$ values $\leq 10$ nM. In other embodiments, exemplary compounds exhibited $IC_{50}$ values $\leq 5$ nM.

As detailed in the exemplification herein, in assays to determine the affinity of compounds in binding to ROCK1, ROCK2, or ROCK1/2 measured in vitro, certain inventive compounds exhibited equilibrium dissociation constant Kd values $\leq 50$ µM. In certain other embodiments, inventive compounds exhibit Kd values $\leq 40$ µM. In certain other embodiments, inventive compounds exhibit Kd values $\leq 30$ µM. In certain other embodiments, inventive compounds exhibit Kd values $\leq 20$ µM. In certain other embodiments, inventive compounds exhibit Kd values $\leq 10$ µM. In certain other embodiments, inventive compounds exhibit Kd values $\leq 7.5$ µM. In certain embodiments, inventive compounds exhibit Kd values $\leq 5$ µM. In certain other embodiments, inventive compounds exhibit Kd values $\leq 2.5$ µM. In certain embodiments, inventive compounds exhibit Kd values $\leq 1$ µM. In certain other embodiments, inventive compounds exhibit Kd values $\leq 750$ nM. In certain other embodiments, inventive compounds exhibit Kd values $\leq 500$ nM. In certain other embodiments, inventive compounds exhibit Kd values $\leq 250$ nM. In certain other embodiments, inventive compounds exhibit Kd values $\leq 100$ nM. In other embodiments, exemplary compounds exhibited Kd values $\leq 75$ nM. In other embodiments, exemplary compounds exhibited Kd values $\leq 50$ nM. In other embodiments, exemplary compounds exhibited Kd values $\leq 40$ nM. In other embodiments, exemplary compounds exhibited Kd values $\leq 30$ nM. In other embodiments, exemplary compounds exhibited Kd values $\leq 20$ nM. In other embodiments, exemplary compounds exhibited Kd values $\leq 10$ nM. In other embodiments, exemplary compounds exhibited Kd values $\leq 5$ nM.

Pharmaceutical Uses and Methods of Treatment

As discussed above, certain of the compounds as described herein exhibit activity generally as modulators of ROCK1, ROCK2, or ROCK1/2 activities. More specifically, compounds of the invention demonstrate the ability to inhibit ROCK1, ROCK2, or ROCK1/2 activities. Thus, in certain embodiments, compounds of the invention are useful for the treatment of any of a number of conditions or diseases in which inhibiting ROCK1, ROCK2, or ROCK1/2 activities thereof have a therapeutically useful role, in particular antifibrotic. Thus, compounds of the invention are useful for the treatment of any condition, disease or disorder in which inhibiting ROCK1, ROCK2, or ROCK1/2 activities would have a beneficial role.

Accordingly, in another aspect of the invention, methods for the treatment of ROCK1, ROCK2, or ROCK1/2 related disorders are provided comprising administering a therapeutically effective amount of a compound of formula (I) as described herein, to a subject in need thereof. In certain embodiments, a method for the treatment of ROCK1, ROCK2, or ROCK1/2 activities related disorders is provided comprising administering a therapeutically effective amount of an inventive compound, or a pharmaceutical composition comprising an inventive compound to a subject in need thereof, in such amounts and for such time as is necessary to achieve the desired result.

In certain embodiments, the method involves the administration of a therapeutically effective amount of the compound or a pharmaceutically acceptable derivative(s) thereof to a subject (including, but not limited to a human or animal) in need of it. Subjects for which the benefits of the compounds of the invention are intended for administration include, in addition to humans, livestock, domesticated, zoo and companion animals.

Thus, as described above, in one aspect of the invention, a method for the treatment of disorders related to inhibiting ROCK1, ROCK2, or ROCK1/2 activities is provided comprising administering a therapeutically effective amount of a compound of formula (I) as described herein, to a subject in need thereof. In certain embodiments of special interest, the inventive method is used for the treatment of, in the case of ROCK1, ROCK2, or ROCK1/2 hyperactivities, hepatic disease, stroke, myocardial infarction and other ischemic or fibrotic diseases. It will be appreciated that the compounds and compositions, according to the method of the present invention, may be administered using any amount and any route of administration effective for the treatment of conditions or diseases in which inhibiting ROCK1, ROCK2, or ROCK1/2 activities thereof have a therapeutically useful role. Thus, the expression "effective amount" as used herein, refers to a sufficient amount of agent to inhibit ROCK1, ROCK2, or ROCK1/2 activities, and to exhibit a therapeutic effect. The exact amount required will vary from subject to subject, depending on the species, age, and general condition of the subject, the severity of the infection, the particular therapeutic agent, its mode and/or route of administration, and the like. The compounds of the invention are preferably formulated in dosage unit form for ease of administration and uniformity of dosage. The expression "dosage unit form" as used herein refers to a physically discrete unit of therapeutic agent appropriate for the patient to be treated. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

Furthermore, after formulation with an appropriate pharmaceutically acceptable carrier in a desired dosage, the pharmaceutical compositions of this invention can be administered to humans and other animals orally, rectally, parenterally, intracisternally, intravaginally, intraperitoneally, subcutaneously, intradermally, intra-ocularly, topically (as by powders, ointments, or drops), buccally, as an oral or nasal spray, or the like, depending on the severity of the disease or disorder being treated. In certain embodiments, the compounds of the invention may be administered at dosage levels of about 0.001 mg/kg to about 50 mg/kg, preferably from about 0.1 mg/kg to about 10 mg/kg for parenteral administration, or preferably from about 1 mg/kg to about 50 mg/kg, more preferably from about 10 mg/kg to about 50 mg/kg for oral administration, of subject body weight per day, one or more times a day, to obtain the desired therapeutic effect. It will also be appreciated that dosages smaller than 0.001 mg/kg or greater than 50 mg/kg (for example 50-100 mg/kg) can be administered to a subject. In certain embodiments, compounds are administered orally or parenterally.

Moreover, pharmaceutical compositions comprising one or more compounds of the invention may also contain other compounds or agents for which co-administration with the compound(s) of the invention is therapeutically advantageous. As many pharmaceutical agents are used in the treatment of the diseases and disorders for which the compounds of the invention are also beneficial, any may be formulated together for administration. Synergistic formulations are also embraced herein, where the combination of at least one compound of the invention and at least one other compounds act more beneficially than when each is given alone.

TREATMENT KIT

In other embodiments, the present invention relates to a kit for conveniently and effectively carrying out the methods in accordance with the present invention. In general, the pharmaceutical pack or kit comprises one or more containers filled with one or more of the ingredients of the pharmaceutical compositions of the invention. Such kits are especially suited for the delivery of solid oral forms such as tablets or capsules. Such a kit preferably includes a number of unit dosages, and may also include a card having the dosages oriented in the order of their intended use. If desired, a memory aid can be provided, for example in the form of numbers, letters, or other markings or with a calendar insert, designating the days in the treatment schedule in which the dosages can be administered. Alternatively, placebo dosages, or calcium dietary supplements, either in a form similar to or distinct from the dosages of the pharmaceutical compositions, can be included to provide a kit in which a dosage is taken every day. Optionally associated with such container(s) can be a notice in the form prescribed by a governmental agency regulating the manufacture, use or sale of pharmaceutical products, which notice reflects approval by the agency of manufacture, use or sale for human administration.

EQUIVALENTS

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

The following examples contain important additional information, exemplification and guidance that can be adapted to the practice of this invention in its various embodiments and the equivalents thereof.

EXEMPLIFICATION

The compounds of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

1) General Description of Synthetic Methods:

The practitioner has a well-established literature of small molecule chemistry to draw upon, in combination with the information contained herein, for guidance on synthetic strategies, protecting groups, and other materials and methods useful for the synthesis of the compounds of this invention.

The various references cited herein provide helpful background information on preparing compounds similar to the inventive compounds described herein or relevant intermediates, as well as information on formulation, uses, and administration of such compounds which may be of interest.

Moreover, the practitioner is directed to the specific guidance and examples provided in this document relating to various exemplary compounds and intermediates thereof.

The compounds of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

According to the present invention, any available techniques can be used to make or prepare the inventive compounds or compositions including them. For example, a variety of solution phase synthetic methods such as those discussed in detail below may be used. Alternatively or additionally, the inventive compounds may be prepared using any of a variety combinatorial techniques, parallel synthesis and/or solid phase synthetic methods known in the art.

It will be appreciated as described below, that a variety of inventive compounds can be synthesized according to the methods described herein. The starting materials and reagents used in preparing these compounds are either available from commercial suppliers such as Aldrich Chemical Company (Milwaukee, Wis.), Bachem (Torrance, Calif.), Sigma (St. Louis, Mo.), or are prepared by methods well known to a person of ordinary skill in the art following procedures described in such references as Fieser and Fieser 1991, "Reagents for Organic Synthesis", vols 1-17, John Wiley and Sons, New York, N.Y., 1991; Rodd 1989 "Chemistry of Carbon Compounds", vols. 1-5 and supps, Elsevier Science Publishers, 1989; "Organic Reactions", vols 1-40, John Wiley and Sons, New York, N.Y., 1991; March 2001, "Advanced Organic Chemistry", 5th ed. John Wiley and Sons, New York, N.Y.; and Larock 1990, "Comprehensive Organic Transformations: A Guide to Functional Group Preparations", $2^{nd}$ ed. VCH Publishers. These schemes are merely illustrative of some methods by which the compounds of this invention can be synthesized, and various modifications to these schemes can be made and will be suggested to a person of ordinary skill in the art having regard to this disclosure.

The starting materials, intermediates, and compounds of this invention may be isolated and purified using conventional techniques, including filtration, distillation, crystallization, chromatography, and the like. They may be characterized using conventional methods, including physical constants and spectral data.

General Reaction Procedures:

Unless mentioned specifically, reaction mixtures were stirred using a magnetically driven stirrer bar. An inert atmosphere refers to either dry argon or dry nitrogen. Reactions were monitored either by thin layer chromatography, by proton nuclear magnetic resonance (NMR) or by high-pressure liquid chromatography (HPLC), of a suitably worked up sample of the reaction mixture.

General Work Up Procedures:

Unless mentioned specifically, reaction mixtures were cooled to room temperature or below then quenched, when necessary, with either water or a saturated aqueous solution of ammonium chloride. Desired products were extracted by partitioning between water and a suitable water-immiscible solvent (e.g. ethyl acetate, dichloromethane, diethyl ether). The desired product containing extracts were washed appropriately with water followed by a saturated solution of brine. On occasions where the product containing extract was deemed to contain residual oxidants, the extract was washed with a 10% solution of sodium sulphite in saturated aqueous sodium bicarbonate solution, prior to the aforementioned washing procedure. On occasions where the product containing extract was deemed to contain residual acids, the extract was washed with saturated aqueous sodium bicarbonate solution, prior to the aforementioned washing procedure (except in those cases where the desired product itself had acidic character). On occasions where the product containing extract was deemed to contain residual bases, the extract was washed with 10% aqueous citric acid solution, prior to the aforementioned washing procedure (except in those cases where the desired product itself had basic character). Post washing, the desired product containing extracts were dried over anhydrous magnesium sulphate, and then filtered. The crude products were then isolated by removal of solvent(s) by rotary evaporation under reduced pressure, at an appropriate temperature (generally less than 45° C.).

General Purification Procedures:

Unless mentioned specifically, chromatographic purification refers to flash column chromatography on silica and/or preparative thin layer chromatography (TLC) plates, using a single solvent or mixed solvent as eluent. Suitably purified desired product containing elutes were combined and concentrated under reduced pressure at an appropriate temperature (generally less than 45° C.) to constant mass. Final compounds were dissolved in 50% aqueous acetonitrile, filtered and transferred to vials, then freeze-dried under high vacuum before submission for biological testing.

1) Synthesis of Exemplary Compounds:

Unless otherwise indicated, starting materials are either commercially available or readily accessibly through laboratory synthesis by anyone reasonably familiar with the art. Described generally below, are procedures and general guidance for the synthesis of compounds as described generally and in subclasses and species herein. In addition, synthetic guidance can be found in Kinoshita, M. et al. Bull. Chem. Soc. Jpn. 1987, 60, 2151-2162; Natchev, I. A. Tetrahedron 1988, 44, 1511-1522; Almirante, N. et al. Tetrahedron Lett. 1998, 39, 3287; and Bellassoued and Majidi, J. Org. Chem. 1993, 58, 2517-2522; the entire contents of which are hereby incorporated by reference.

The skilled practitioner will recognize that vinylpyrimidinyl C(3)- and C(5)-substituted 1H-pyrazole tautomers typically exist as mixtures which rapidly interconvert in solution. Because of this rapid proton transfer, 3- and 5-substituted pyrazole tautomers do not normally have separate existence. The tautomers may, however, exist in solution predominantly in one form. See, for example, T. L. Gilchrist, "Heterocyclic Chemistry" 2nd Edition, Longman Scientific and Technical, 1992; p 287; which is incorporated herein by reference.

In certain exemplary embodiments, compounds of formula I may be prepared as follows according to Scheme 1:

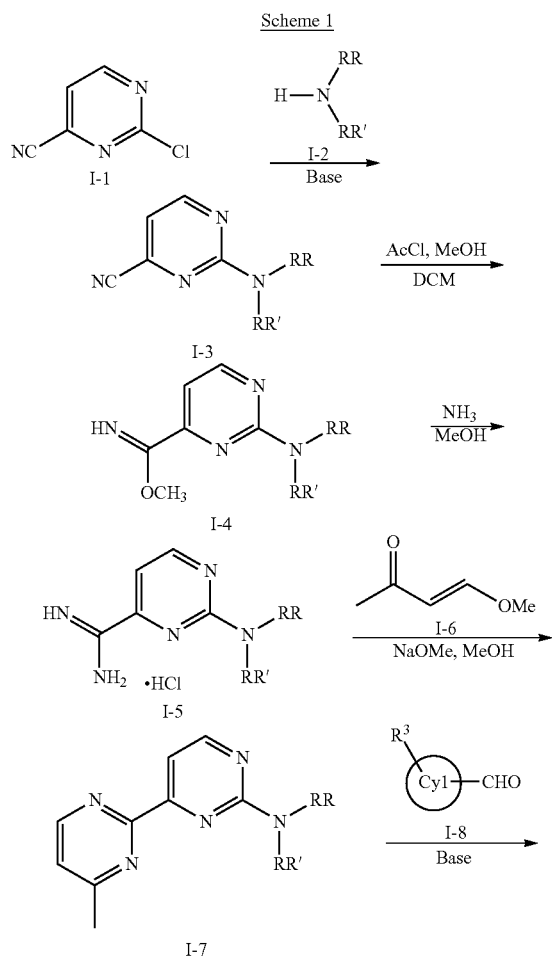

wherein

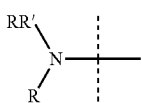

is R—, representing an optionally substituted heterocyclic, aromatic, or heteroaromatic; wherein, the optional substituents are selected from hydrogen, deuterium, halo, —CN, —NO$_2$, aliphatic, alicyclic, heteroaliphatic, heterocyclic, aromatic, heteroaromatic, —OR$^a$, —NR$^b$R$^c$, —S(=O)$_w$R$^d$, —S(=O)$_w$NR$^e$R$^f$, —C(=O)R$^g$, —CO$_2$R$^h$, —CONR$^i$R$^j$, —NR$^k$CONR$^l$R$^m$, —OCONR$^n$R$^o$, or —NR$^k$CO$_2$R$^p$; R$^3$ and Cy1 have the same meanings as those in the claims; "Base" refers to inorganic or organic bases. Some examples of organic bases include but are not limited to Me$_3$N, Et$_3$N, n-Pr$_3$N, i-Pr$_3$N, n-Bu$_3$N, s-Bu$_3$N, i-Bu$_3$N, t-Bu$_3$N, i-Pr$_2$NEt, pyridine, 1,8-diazabicyclo(5.4.0)undec-7-ene (DBU), 1,4-diazabicyclo[2.2.2]octane (DABCO), 1,1,2,3,3-pentamethylguanidine, 1,1,2,3,3-pentaethylguanidine, N-methylmorpholine, N-ethylmorpholine, N-isopropylmorpholine, N-methylpiperidine, N-ethylpiperidine, N-isopropylpiperidine, 1,4-dimethylpiperazine, 1,4-diethylpiperazine, 1,4-diisopropylpiperazine, N-methylpyrrolidine, N-ethylpyrrolidine, N-isopropylpyrrolidine, MeONa, MeOK, MeOLi, EtOLi, EtONa, EtOK, n-PrOLi, n-PrONa, n-PrOK, i-PrOLi, i-PrONa, i-PrOK, n-BuOLi, n-BuONa, n-BuOK, i-BuOLi, i-BuONa, i-BuOK, s-BuOLi, s-BuONa, s-BuOK, t-BuOLi, t-BuONa, t-BuOK, n-BuLi, s-BuLi, t-BuLi, NaN(SiMe$_3$)$_2$, LiN(SiMe$_3$)$_2$, and KN(SiMe$_3$)$_2$. Some examples of inorganic bases include but are not limited to LiOH, NaOH, KOH, RbOH, CsOH, Cs$_2$CO$_3$, Rb$_2$CO$_3$, Li$_2$CO$_3$, Na$_2$CO$_3$, K$_2$CO$_3$, NaHCO$_3$, LiF, NaF, KF, RbF, CsF, K$_3$PO$_4$, K$_2$HPO$_4$, KH$_2$PO$_4$, Na$_3$PO$_4$, Na$_2$HPO$_4$, NaH$_2$PO$_4$, Li$_3$PO$_4$, Li$_2$HPO$_4$, LiH$_2$PO$_4$, NaH, LiH, KH, RbH, CsH, CaO, Ca(OH)$_2$, Ca$_2$CO$_3$, MgO, Mg(OH)$_2$, or Mg$_2$CO$_3$.

Starting material I-1 is commercially available from multiple suppliers. The displacement reaction between I-1 and I-2 gave product I-3. Compound I-3 was converted into the amidine intermediate I-5 in two steps. Compound I-5 reacted with I-6 to give the methylpyrimidinyl compound 1-7. Condensation between I-7 and aldehyde I-8 in the presence of a base to afford the target compound I-A.

It will be appreciated that the reaction sequence illustrated in Scheme 1 is general in nature, and one skilled in the art will recognize that the method could be used to prepare analogues in which Cy1, R$^3$, RR, and RR' represent virtually any type of substituents.

In certain exemplary embodiments, compounds of formula I may be prepared as follows according to Scheme 2:

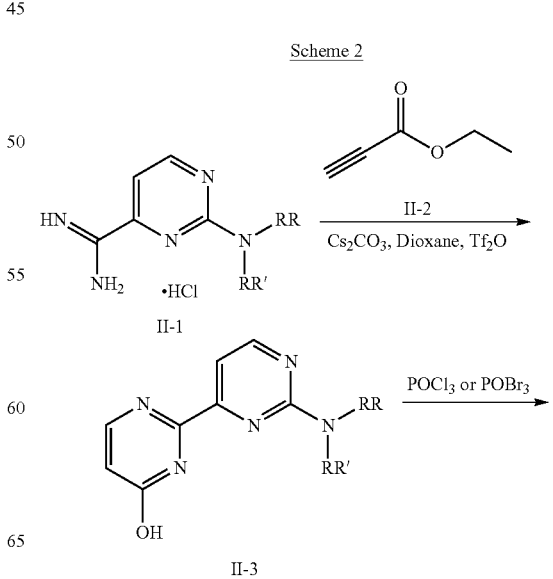

43

-continued

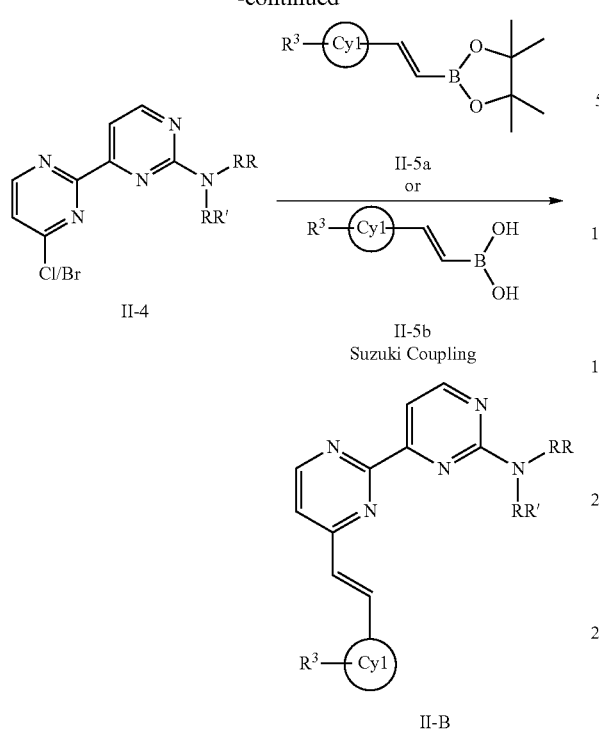

II-5a
or
II-5b
Suzuki Coupling

II-4

II-B

The definitions of

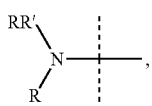

Cy1, and R3 are the same as those in Scheme 1. Tf₂O refers to triflic anhydride. Suzuki Coupling is a name reaction in organic chemistry. More detailed information about Suzuki Coupling reaction can be found at the following website: www.organic-chemistry.org/namedreactions/suzuki-coupling.shtm.

Starting material II-1 (=I-5) can be prepared according to the method described in Scheme 1. Condensation reaction between II-1 and commercially available methyl or ethyl propiolate (II-2) gives compound II-3. Compound II-3 reacts with phosphoryl chloride ($POCl_3$) or phosphoryl bromide ($POBr_3$) to generate corresponding chloride or bromide II-4. Compound II-4 reacts with boronic ester II-5a or boronic acid II-5b under Suzuki Coupling conditions to afford the target molecule II-B.

It will be appreciated that the reaction sequence illustrated in Scheme 2 is general in nature, and one skilled in the art will recognize that the method could be used to prepare analogues in which Cy1, $R^3$, RR, and RR' represent virtually any type of substituents.

The following represent non-limiting examples of the synthetic methods.

44

Example 1. (E)-5-Methoxy-2-(4-(2-(pyridine-4-yl)vinyl)-[2,4'-bipyrimidin]-2'-yl)isoindoline (Ex. 1)

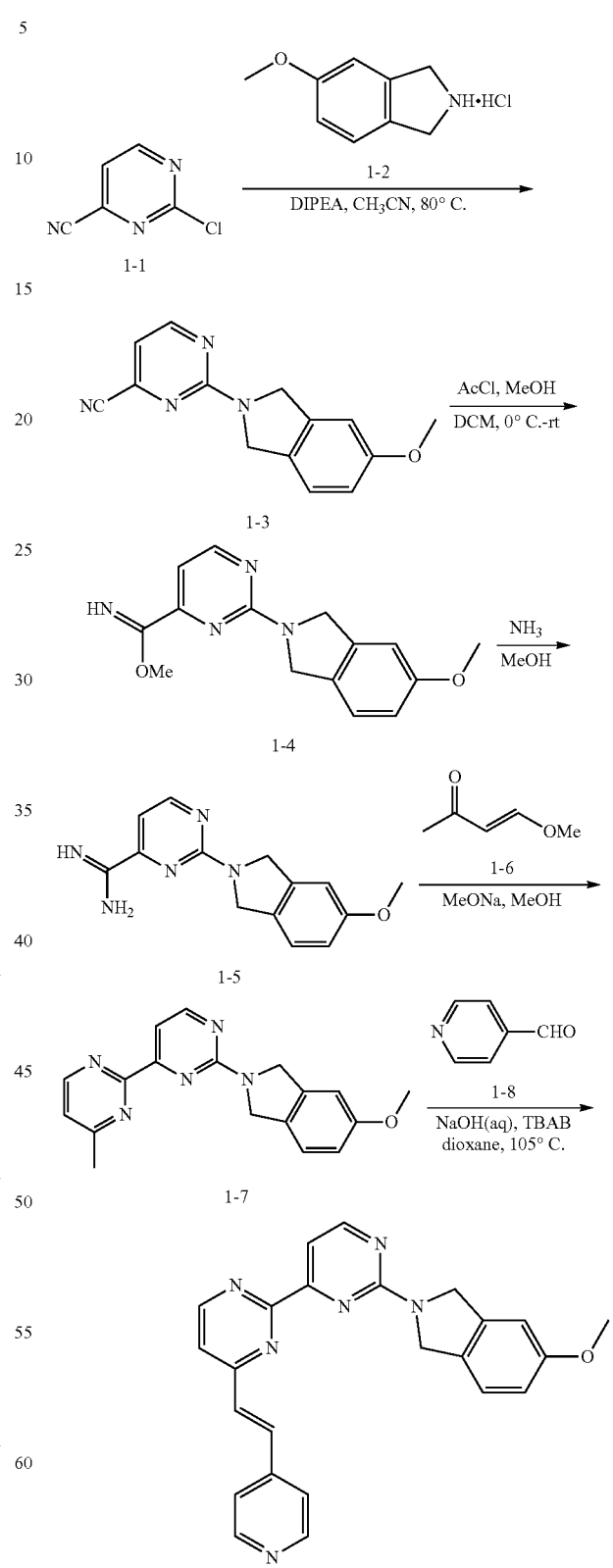

Step 1: 2-(5-Methoxyisoindolin-2-yl)pyrimidine-4-carbonitrile (1-3)

To a stirred mixture of 2-chloropyrimidine (1-1, 1.5 g, 10.8 mmol) and 5-methoxyisoindoline hydrochloride (1-2, 2.0 g, 10.8 mmol) in anhydrous acetonitrile (40 mL) was dropwise added N,N-diisopropylethylamine (4.14 mL, 23.76 mmol). The reaction mixture was stirred for 3 h at 80° C. The resulting solution was concentrated under vacuum and then triturated with water, and filtered. The filter cake was thoroughly washed with water and dried under vacuum to give brownish product 1-3 (2.45 g, yield: 90%). MS (ESI$^+$): m/z: 253.1 (M+H)$^+$.

Step 2: Methyl 2-(5-methoxyisoindolin-2-yl)pyrimidine-4-carbimidate (1-4)

To a stirred slurry of 1-3 (1.2 g, 4.8 mmol) in anhydrous methylene chloride (25 mL) was successively added acetyl chloride (3.4 mL, 47.6 mmol) and anhydrous methanol (2.9 mL, 71.4 mmol) at 0° C. The reaction mixture was slowly warmed up to rt and stirred for 12 h and then solvent was removed under vacuum to afford a yellowish solid (1-4). The solid was used for the next step without further purification.

Step 3: 2-(5-Methoxyisoindon-2-yl)pyrimidin-4-carboximidamide (1-5)

The yellowish solid 1-4 from the previous step was treated with 20 mL of 7 N ammonia in methanol. The reaction mixture was stirred for 12 h at rt and then concentrated under vacuum. The residue was triturated with ethyl acetate, and filtered. The filter cake was used for the next step without further purification. MS (ESI$^+$): m/z: 270.1 (M+H)$^+$.

Step 4: 5-Methoxy-2-(4-methyl-[2,4'-bipyrimidin]-2'-yl)isoindoline (1-7)

The crude compound 1-5 from the previous step was taken up in anhydrous methanol (25 mL). To this solution was successively added (E)-4-methoxybut-3-en-2-one (1-6, 0.573 mL, 5.7 mmol) and 0.5 N sodium methoxide (19.8 mL, 9.9 mmol). The reaction mixture was stirred for 12 h at 50° C. and then concentrated under vacuum. The residue was taken up in methylene chloride and washed with water and brine. Organic layer was dried over anhydrous sodium sulfate, evaporated under vacuum and the residue was purified by silica gel column to give 1-7 as a yellow powder (198 mg, 13% overall yield after 3 steps). MS (ESI$^+$): m/z: 320.2 (M+H)$^+$.

Step 5: (E)-5-Methoxy-2-(4-(2-(pyridine-4-yl)vinyl)-[2,4'-bipyrimidin]-2'-yl)isoindoline (Ex. 1)

To a stirred mixture of 1-7 (170 mg, 0.53 mmol) and tetrabutylammonium bromide (TBAB, 200 mg, 0.62 mmol) in 2 mL of dioxane was sequentially added 2 mL of 5 N NaOH(aq) and 4-pyridinecarboxaldehyde (1-8, 284 mg, 2.65 mmol). The reaction mixture was stirred at 105° C. overnight. After cooled to rt, the organic layer was separated and diluted with methylene chloride and washed with water and brine. The organic layer was dried over sodium sulfate, evaporated under vacuum and the residue was purified by preparative TLC to afford compound Ex. 1 as a pale white solid (55.4 mg, yield: 26%). $^1$H-NMR (300 MHz, CDCl$_3$): δ (ppm): 9.0 (d, J=4.8 Hz, 1H), 8.69 (m, 2H), 8.63 (d, J=5.1 Hz, 1H), 7.95 (d, J=15.9 Hz, 1H), 7.74 (d, J=15.9 Hz, 1H), 7.53 (m, 2H), 7.43 (d, J=5.1 Hz, 1H), 7.37 (d, J=15.9 Hz, 1H), 7.27 (m, 2H), 6.87 (m, 2H), 5.04 (br, 4H), 3.84 (s, 3H). MS (ESI$^+$): m/z: 409.2 (M+H)$^+$.

Example 2. (E)-2-(4-(2-(1H-Pyrazol-3-yl)vinyl)-[2,4'-bipyrimidin]-2'-yl)-5-methoxyisoindoline (Ex. 2)

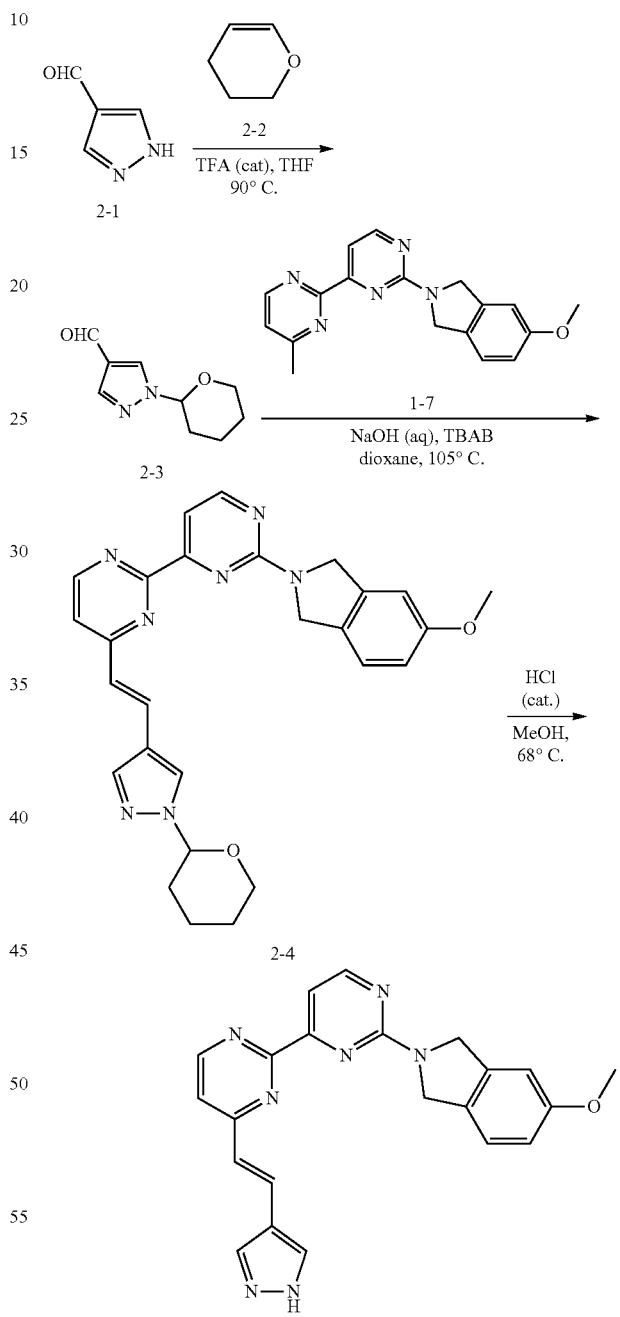

Step 1: 1-(Tetrahydro-2H-pyran-2-yl)-1H-pyrazole-4-carbaldehyde (2-3)

To a stirred solution of pyrazole carboxaldehyde (2-1, 300 mg, 3.1 mmol) in tetrahydrofuran was sequentially added 3,4-dihydro-2H-pyran (2-2, 867 mg, 10.3 mmol) and catalytic amount of trifluoroacetic acid. The resulting solution was refluxed for 4 h and then cooled to rt. The reaction was quenched by addition of trace amount of sodium hydride. Solvent was removed under vacuum and the residue was purified by silica gel chromatography to give 2-3 (520 mg, 92%). MS (ESI$^+$): m/z: 181.1 (M+H)$^+$.

Step 2: (E)-5-Methoxy-2-(4-(2-(1-(tetrahydro-2H-pyran-2-yl)-1H-pyrazol-3-yl)vinyl)-[2,4'-bipyrimidin]-2'-yl)isoindoline (2-4)

To a stirred solution of 1-7 (50 mg, 0.15 mmol) and tetrabutylammonium bromide (TBAB, 40 mg, 0.12 mmol) in 3 mL of dioxane was sequentially added 3 mL of 5 N NaOH(aq) and 2-3 (112 mg, 0.62 mmol). The reaction was stirred at 105° C. overnight. After cooled to rt, the organic layer was separated and diluted with methylene chloride and washed with water and brine. The organic layer was dried over sodium sulfate, evaporated under vacuum, and the residue was purified by preparative TLC to afford compound 2-4 as a yellow powder (60 mg, yield: 80%). MS (ESI$^+$): m/z: 482.3 (M+H)$^+$.

Step 3: (E)-2-(4-(2-(1H-Pyrazol-3-yl)vinyl)-[2,4'-bipyrimidin]-2'-yl)-5-methoxyisoindoline (Ex. 2)

To a stirred mixture of compound 2-4 (60 mg, 0.12 mmol) in 5 mL of methanol was added 50 μL of conc. HCl. The resulting mixture was refluxed for 3 h and then evaporated under vacuum. The solid residue was triturated with sodium bicarbonate solution and filtered. The filter cake was thoroughly washed with water and dried under vacuum to give Ex. 2 as a yellowish powder (18.9 mg, yield: 34%). $^1$H-NMR (300 MHz, CDCl$_3$): δ (ppm): 13.06 (br, 1H), 8.87 (m, 1H), 8.62 (m, 1H), 8.03 (m, 3H), 7.57 (m, 2H), 7.32 (br, 1H), 7.05 (m, 2H), 6.88 (m, 1H), 4.85 (br, 4H), 3.76 (s, 3H). MS (ESI$^+$): m/z: 398.2 (M+H)$^+$.

Example 3. (E)-4-(2-(2'-(5-Methoxyisoindolin-2-yl)-[2,4'-bipyrimidin]-4-yl)vinyl)quinoline (Ex. 3)

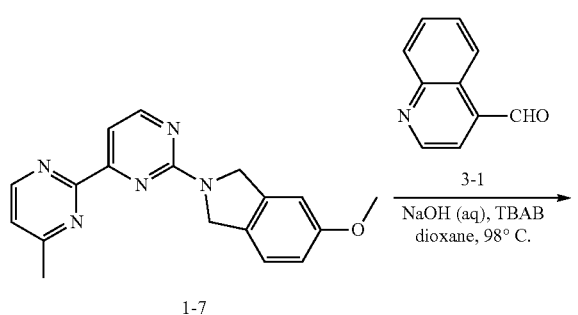

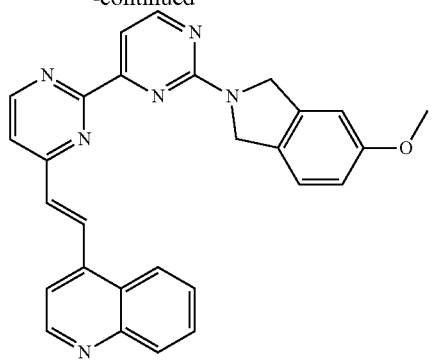

Ex. 3

Prepared by following the same procedure described in Step 5 in Example 1. A yellow solid was obtained in 56% yield. $^1$H-NMR (300 MHz, CDCl$_3$): δ (ppm): 9.03 (d, J=5.1 Hz, 1H), 8.99 (d, J=4.3 Hz, 1H), 8.84 (d, J=15.9 Hz, 1H), 8.67 (d, J=4.8 Hz, 1H), 8.32 (d, J=8.1 Hz, 1H), 8.22 (d, J=8.1 Hz, 1H), 7.75 (m, 4H), 7.48 (d, J=5.1 Hz, 1H), 7.41 (d, J=15.6 Hz, 1H), 7.26 (s, 1H), 6.90 (s, 1H), 6.87 (d, J=2.4 Hz, 1H), 5.06 (br, 4H), 3.85 (s, 3H). MS (ESI$^+$): m/z: 459.3 (M+H)$^+$.

Example 4. (E)-4-(2-(2'-(5-Methoxyisoindolin-2-yl)-[2,4'-bipyrimidin]-4-yl)vinyl)-1H-pyrrolo[2,3-b]pyridine (Ex. 4)

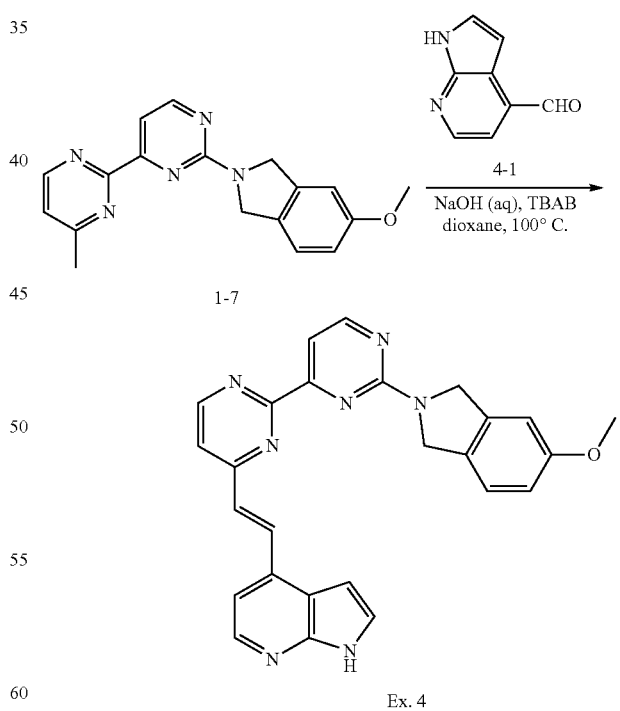

Prepared by following the same procedure described in Step 5 in Example 1. A yellow solid was obtained in 10% yield. $^1$H-NMR (300 MHz, CD$_3$OD): δ (ppm): 8.93 (d, J=5.4 Hz, 1H), 8.58 (d, J=5.1 Hz, 1H), 8.35 (d, J=15.6 Hz, 1H), 8.24 (s, 1H), 7.58 (d, J=4.8 Hz, 1H), 7.55 (d, J=15.9 Hz, 1H), 7.52 (s, 1H), 7.37 (d, J=5.1 Hz, 1H), 7.25 (d, J=5.1 Hz, 1H), 7.25 (d, J=8.1 Hz, 1H), 6.86 (m, 3H), 5.00 (br, 4H), 3.81 (s, 3H). MS (ESI⁺): m/z: 448.2 (M+H)⁺.

Example 5. (E)-4-(2-(2'-(5-Methoxyisoindolin-2-yl)-[2,4'-bipyrimidin]-4-yl)vinyl)pyrimidin-2-amine (Ex. 5)

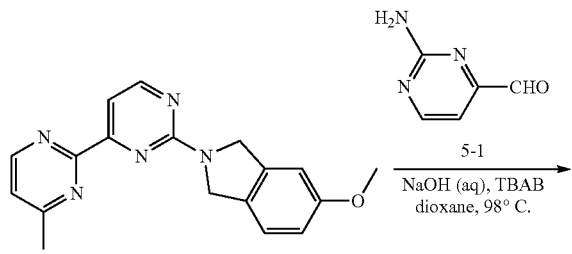

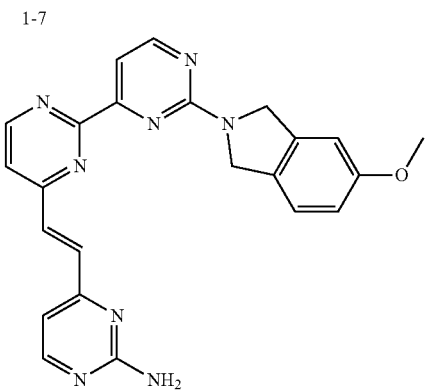

Prepared by following the same procedure described in Step 5 in Example 1. A yellow solid was obtained in 7% yield. ¹H-NMR (300 MHz, DMSO-d₆): δ (ppm): 9.06 (d, J=5.1 Hz, 1H), 8.66 (d, J=5.1 Hz, 1H), 8.36 (d, J=4.8 Hz, 1H), 7.85 (d, J=5.1 Hz, 1H), 7.80 (s, 2H), 7.64 (d, J=5.1 Hz, 1H), 7.35 (br, 1H), 7.05 (br, 1H), 6.92 (m, 1H), 6.90 (m, 1H), 6.72 (br, 2H), 4.88 (br, 4H), 3.78 (s, 3H). MS (ESI⁺): m/z: 425.2 (M+H)⁺.

Example 6. (E)-2-(4-(2-(Pyridin-4-yl)vinyl)-[2,4'-bipyrimidin]-2'-yl)isoindolin-5-ol (Ex. 6)

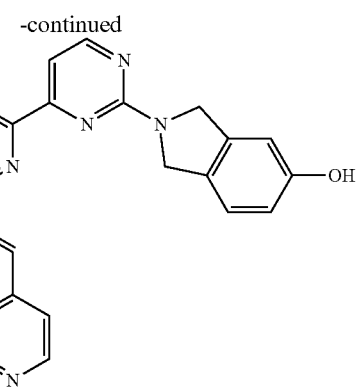

At 0° C. and under nitrogen, to a solution of (E)-5-methoxy-2-(4-(2-(pyridin-4-yl)vinyl)-[2,4'-bipyrimidin]-2'-yl)isoindoline (Ex. 1, 100 mg, 0.245 mmol) in dry DCM (2 mL) was added BBr₃ (1 M in DCM, 0.73 mL, 0.73 mmol) dropwise. The resulting mixture was stirred at 0° C. for 1 h, then quenched with water (2 mL). The precipitates were collected by filtration, washed with water (1 mL), and dried in vacuo to give (E)-2-(4-(2-(pyridin-4-yl)vinyl)-[2,4'-bipyrimidin]-2'-yl)isoindolin-5-ol as a yellowish white solid (Ex. 6, 69 mg, yield: 72%). ¹H-NMR (300 MHz, CD₃OD): δ (ppm): 9.06 (d, J=5.1 Hz, 1H), 8.82 (d, J=6.3 Hz, 2H), 8.58 (d, J=5.1 Hz, 1H), 8.35-8.24 (m, 3H), 7.97-7.78 (m, 3H), 7.17 (d, J=5.1 Hz, 1H), 6.79-6.73 (m, 2H), 5.06-4.96 (m, 4H). MS (ESI⁺): m/z: 395.2 (M+H)⁺.

Example 7. (E)-2-(4-(2-(Pyridin-4-yl)vinyl)-[2,4'-bipyrimidin]-2'-yl)isoindolin-5-yl Trifluoromethanesulfonate (Ex. 7)

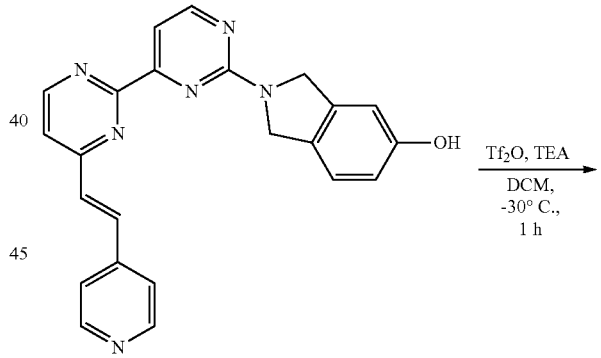

At −30° and under nitrogen, to a suspension of (E)-2-(4-(2-(pyridin-4-yl)vinyl)-[2,4'-bipyrimidin]-2'-yl)isoindolin-5-ol (Ex. 6, 87 mg, 0.220 mmol) in dry DCM (2 mL) was added triflic anhydride (0.04 mL, 0.264 mmol) dropwise. The resulting mixture was stirred at the same temperature for 1 h, then quenched was ice-water (1 mL). The mixture was extracted with DCM (3×3 mL). The organic layers were combined, dried over Na$_2$SO$_4$, filtered, and concentrated to dryness. The residue was purified by silica gel column chromatography (eluted with 3% 7 M NH$_3$ in MeOH in DCM) to give (E)-2-(4-(2-(pyridin-4-yl)vinyl)-[2,4'-bipyrimidin]-2'-yl)isoindolin-5-yl trifluoromethanesulfonate as a pale yellow solid (Ex. 7, 53 mg, yield: 46%). $^1$H-NMR (300 MHz, CDCl$_3$): δ (ppm): 8.99 (d, J=5.1 Hz, 1H), 8.71-8.64 (m, 3H), 7.94 (d, J=15.9 Hz, 1H), 7.75 (d, J=4.8 Hz, 1H), 7.50 (d, J=6.3 Hz, 2H), 7.45-7.42 (m, 2H), 7.39 (s, 1H), 7.28 (s, 1H), 7.22-7.20 (m, 1H), 5.20-5.04 (m, 4H). MS (ESI$^+$): m/z: 527.3 (M+H)$^+$.

Example 8. (E)-2-(4-(2-(Pyridin-4-yl)vinyl)-[2,4'-bipyrimidin]-2'-yl)isoindoline-5-carbonitrile (Ex. 8)

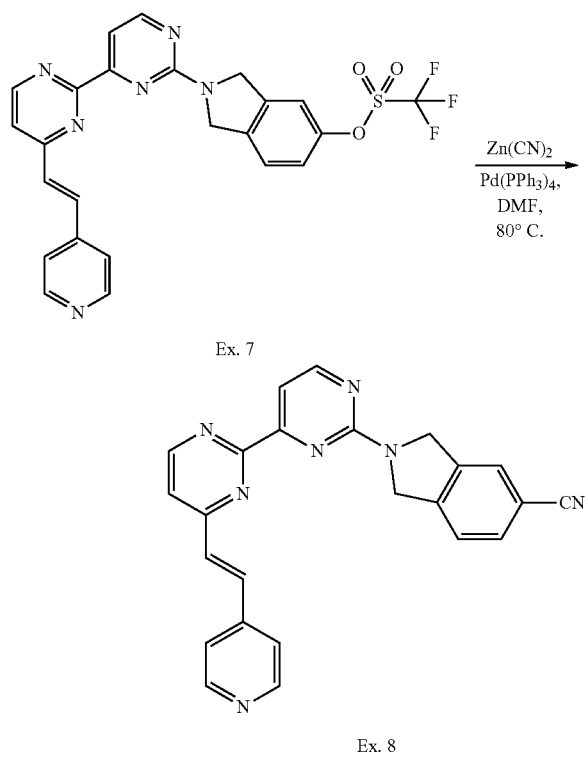

A mixture of (E)-2-(4-(2-(pyridin-4-yl)vinyl)-[2,4'-bipyrimidin]-2'-yl)isoindolin-5-yl trifluoromethanesulfonate (Ex. 7, 100 mg, 0.19 mmol), Pd(PPh$_3$)$_4$ (22 mg, 0.019 mmol) and zinc cyanide (18 mg, 0.38 mmol) in DMF (1 mL) was degassed and back filled with nitrogen three times. The reaction mixture was stirred at 80° C. for 12 h. The solvent was evaporated and the residue was diluted with water (2 mL) and extracted with DCM (3×2 mL). The organic layers were combined, dried over Na$_2$SO$_4$, filtered, and concentrated to dryness. The residue was purified by silica gel column chromatography (eluted with 3% 7 M NH$_3$ in MeOH in DCM) to afford (E)-2-(4-(2-(pyridin-4-yl)vinyl)-[2,4'-bipyrimidin]-2'-yl)isoindoline-5-carbonitrile as a yellow solid (Ex. 8, 38 mg, yield: 52%). $^1$H-NMR (300 MHz, CDCl$_3$): δ (ppm): 8.99 (d, J=5.1 Hz, 1H), 8.70-8.65 (m, 3H), 7.94 (d, J=15.9 Hz, 1H), 7.75 (d, J=5.1 Hz, 1H), 7.67-7.62 (m, 2H), 7.50-7.48 (m, 2H), 7.44 (d, J=5.1 Hz, 1H), 7.39 (s, 1H), 7.33 (d, J=2.4 Hz, 1H), 5.10 (br, 4H). MS (ESI$^+$): m/z: 404.2 (M+H)$^+$.

Example 9. (E)-N,N-Dimethyl-2-((2-(4-(2-(pyridin-4-yl)vinyl)-[2,4'-bipyrimidin]-2'-yl)isoindolin-5-yl)oxy)ethanamine (Ex. 9)

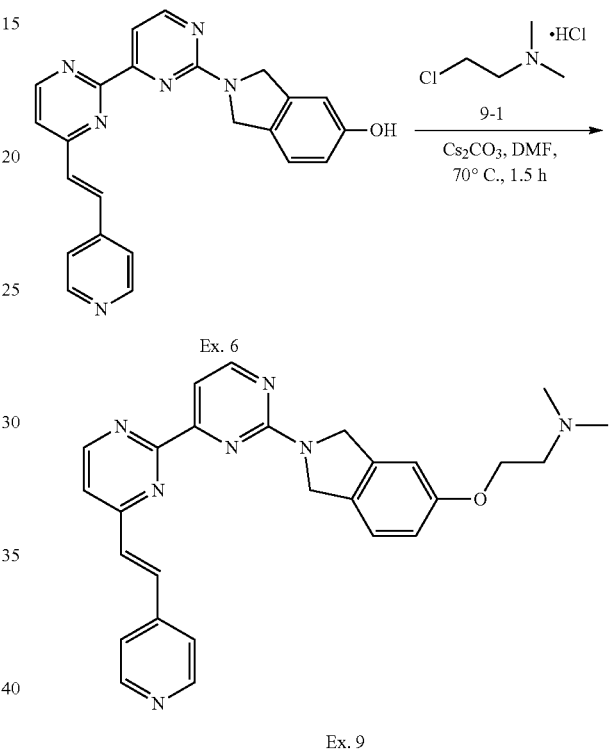

(E)-2-(4-(2-(pyridin-4-yl)vinyl)-[2,4'-bipyrimidin]-2'-yl)isoindolin-5-ol (Ex. 6, 100 mg, 0.254 mmol) and 2-chloro-N,N-dimethylethylamine hydrochloride (9-1, 73 mg, 0.507 mmol) were dissolved in DMF (6 mL). The mixture was stirred at room temperature for 10 min, then Cs$_2$CO$_3$ (330 mg, 1.01 mmol) was added. The resulting mixture was stirred at 70° for 1.5 h. After cooled to room temperature, the reaction was diluted with water (5 mL) and extracted with ethyl acetate (3×5 mL). The organic layers were combined, washed with water (3×3 mL), dried over MgSO$_4$, filtered and concentrated. The residue was purified by silica gel chromatography on ISCO (eluted with DCM:MeOH=4:1) to afford (E)-N,N-dimethyl-2-((2-(4-(2-(pyridin-4-yl)vinyl)-[2,4'-bipyrimidin]-2'-yl)isoindolin-5-yl)oxy)ethanamine as a yellow solid (Ex. 9, 7 mg, yield: 6%). $^1$H-NMR (300 MHz, CDCl$_3$): δ (ppm): 8.98 (d, J=5.1 Hz, 1H), 8.68 (d, J=5.9 Hz, 2H), 8.63 (d, J=5.6 Hz, 1H), 7.94 (d, J=15.9 Hz, 1H), 7.69 (d, J=5.01 Hz, 1H), 7.49 (d, J=6.01 Hz, 2H), 7.42 (d, J=5.0 Hz, 1H), 7.35 (d, J=16.0 Hz, 1H), 7.25 (d, J=8.09 Hz, 1H), 6.90 (d, J=11.4 Hz, 1H), 6.89 (d, J=10.5 Hz, 1H), 5.03 (br, 4H), 4.10 (t, J=5.7 Hz, 2H), 2.76 (t, J=5.7 Hz, 2H), 2.36 (s, 6H). MS (ESI$^+$): m/z: 466.3 (M+H)$^+$.

Example 10. (E)-Methyl 2-((2-(4-(2-(pyridin-4-yl)vinyl)-[2,4'-bipyrimidin]-2'-yl)isoindolin-5-yl)oxy)acetate (Ex. 10)

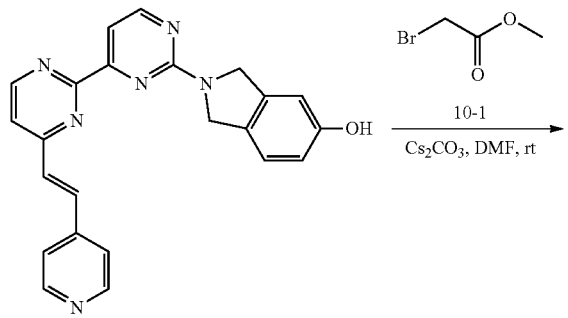

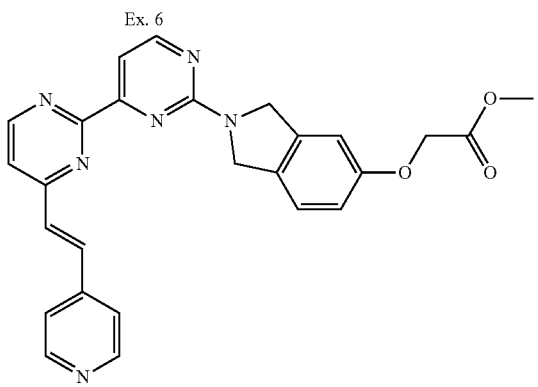

A mixture of (E)-2-(4-(2-(pyridin-4-yl)vinyl)-[2,4'-bipyrimidin]-2'-yl)isoindolin-5-ol (Ex. 6, 2.0 g, 5.07 mmol) and Cs₂CO₃ (4.9 g, 15.2 mmol) in DMF (10 mL) was stirred at room temperature for 10 min. Methyl 2-bromoacetate (10-1, 0.53 mL, 5.57 mmol) was added in. The resulting mixture was stirred at room temperature for 2 h, filtered, and the solvent was removed under reduced pressure. The residue was purified by silica gel column chromatography to give (E)-methyl 2-((2-(4-(2-(pyridin-4-yl)vinyl)-[2,4'-bipyrimidin]-2'-yl)isoindolin-5-yl)oxy)acetate as a brown solid (Ex. 10, 1.5 g, yield: 62%). MS (ESI⁺): m/z: 467.3 (M+H)⁺.

Example 11. (E)-N-Methyl-2-((2-(4-(2-(pyridin-4-yl)vinyl)-[2,4'-bipyrimidin]-2'-yl)isoindolin-5-yl)oxy)acetamide (Ex. 11)

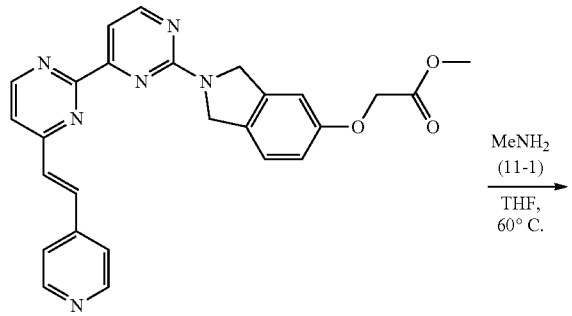

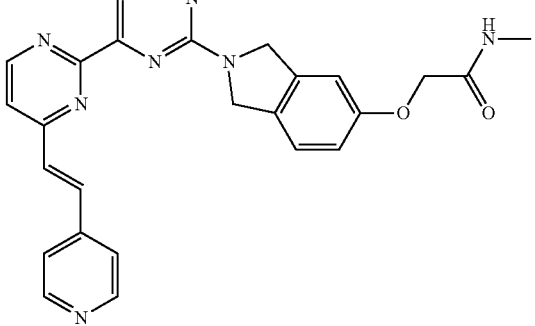

A mixture of (E)-methyl 2-((2-(4-(2-(pyridin-4-yl)vinyl)-[2,4'-bipyrimidin]-2'-yl)isoindolin-5-yl)oxy)acetate (Ex. 10, 20 mg, 0.043 mmol) and methylamine in THF (2 M, 0.5 mL, 1.0 mmol) was stirred in a sealed tube at 60° C. for 8 h. The solvent was removed and the residue was purified by silica gel column chromatography (eluted with 3% 7 M NH₃ in MeOH in DCM) to give (E)-N-methyl-2-((2-(4-(2-(pyridin-4-yl)vinyl)-[2,4'-bipyrimidin]-2'-yl)isoindolin-5-yl)oxy)acetamide as a pale yellow solid (Ex. 11, 6 mg, yield: 30%). ¹H-NMR (300 MHz, CD₃OD): δ (ppm): 8.99 (d, J=4.5 Hz, 1H), 8.69-8.63 (m, 3H), 7.94 (d, J=15.9 Hz, 1H), 7.71 (d, J=4.8 Hz, 1H), 7.49 (d, J=6.0 Hz, 2H), 7.42 9d, J=5.1 Hz, 1H), 7.38-7.28 (m, 2H), 6.92-6.86 (m, 2H), 5.10 (s, 2H), 4.97 (s, 2H), 4.52 (s, 2H), 2.93 (d, J=4.8 Hz, 3H). MS (ESI⁺): m/z: 466.3 (M+H)⁺.

Example 12. (E)-N-Ethyl-2-((2-(4-(2-(pyridin-4-yl)vinyl)-[2,4'-bipyrimidin]-2'-yl)isoindolin-5-yl)oxy)acetamide (Ex. 12)

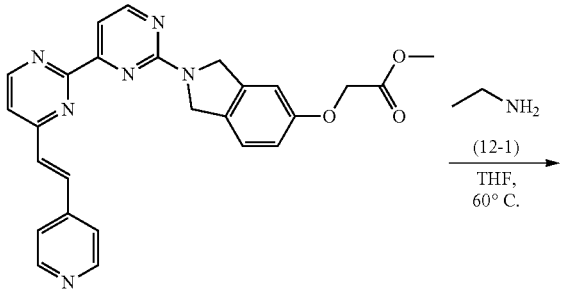

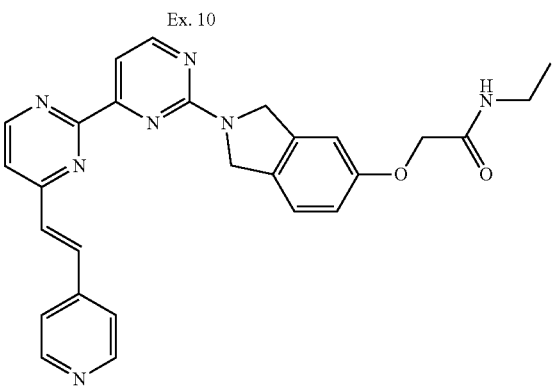

Prepared by following the same procedure described for Example 11. Yield: 37%. 1H-NMR (300 MHz, CDCl$_3$): δ (ppm): 8.98 (d, J=5.1 Hz, 1H), 8.69-8.62 (m, 3H), 7.93 (d, J=15.9 Hz, 1H), 7.70 (d, J=5.1 Hz, 1H), 7.49 (d, J=5.7 Hz, 2H), 7.42 (d, J=5.1 Hz, 1H), 7.35 (d, J=15.9 Hz, 1H), 7.28 (d, J=8.4 Hz, 1H), 6.91-6.86 (m, 2H), 6.61-6.59 (m, 1H), 5.10 (s, 2H), 4.97 (s, 2H), 4.50 (s, 2H), 3.40 (pent, J=7.2 Hz, 2H), 1.20 (t, J=7.5 Hz, 3H). MS (ESI$^+$): m/z: 480.3 (M+H)$^+$.

Example 13. (E)-N-Isopropyl-2-((2-(4-(2-(pyridin-4-yl)vinyl)-[2,4'-bipyrimidin]-2'-yl)isoindolin-5-yl)oxy)acetamide (Ex. 13)

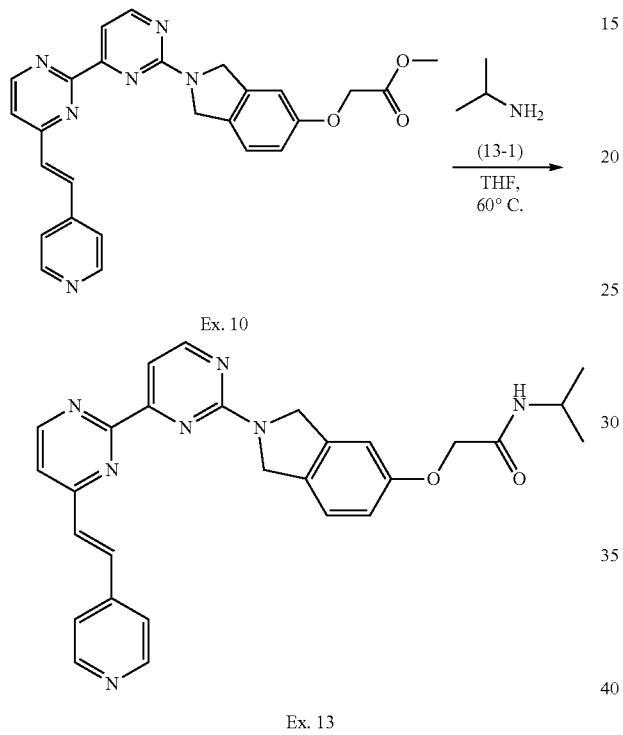

Prepared by following the same procedure described for Example 11. Yield: 53%. $^1$H-NMR (300 MHz, CDCl$_3$): δ (ppm): 8.98 (d, J=5.1 Hz, 1H), 8.69-8.62 (m, 3H), 7.93 (d, J=15.9 Hz, 1H), 7.70 (d, J=5.1 Hz, 1H), 7.49 (d, J=5.9 Hz, 2H), 7.42 (d, J=5.1 Hz, 1H), 7.35 (d, J=15.9 Hz, 1H), 7.28 (d, J=8.4 Hz, 1H), 6.92-6.87 (m, 1H), 6.40-6.38 (m, 1H), 5.10 (s, 2H), 4.97 (s, 2H), 4.48 (s, 2H), 4.20 (sext, J=6.6 Hz, 2H), 1.21 (d, J=6.6 Hz, 6H). MS (ESI$^+$): m/z: 494.3 (M+H)$^+$.

Example 14. (E)-5-Fluoro-2-(4-(2-(pyridine-4-yl)vinyl)-[2,4'-bipyrimidin]-2'-yl)isoindoline (Ex. 14)

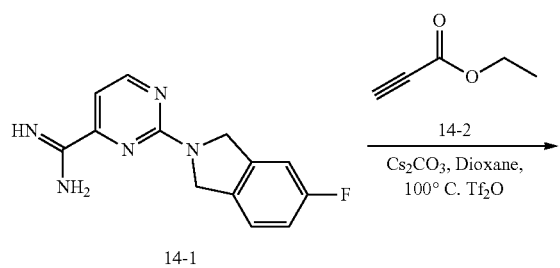

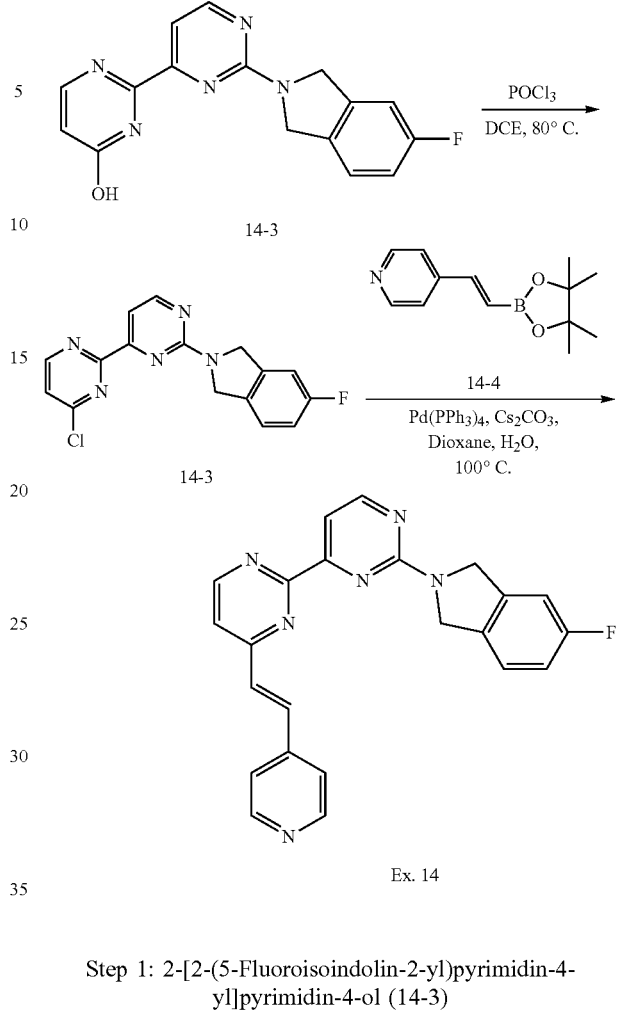

Step 1: 2-[2-(5-Fluoroisoindolin-2-yl)pyrimidin-4-yl]pyrimidin-4-ol (14-3)

A mixture of 2-(5-fluoroisoindolin-2-yl)pyrimidine-4-carboxamidine hydrochloride (14-1, prepared according to Steps 1-3 in Example 1, 100 mg, 0.34 mmol) and ethyl propiolate (14-2, 0.34 μL, 0.34 mmol), and cesium carbonate (222 mg, 0.68 mmol) was stirred in dioxane (14 mL) at 100° C. for 12 h. The reaction mixture was cooled down to room temperature and trifle anhydride (Tf$_2$O, 0.226 μL, 1.36 mmol) was added dropwise. After stirring for 12 h, the solvent was removed and the residue was taken up with DCM (10 mL) and washed with water (2×5 mL). The organic layers were combined, driver over MgSO$_4$, filtered, and concentrated to dryness. The residue was suspended in MeOH (0.3 mL) and the solids were collected by filtration to afford 28 mg of the desired product 2-[2-(5-fluoroisoindolin-2-yl)pyrimidin-4-yl]pyrimidin-4-ol (14-3, yield: 27%). MS (ESI$^+$): m/z: 310.2 (M+H)$^+$.

Step 2: 2-[4-(4-Chloropyrimidin-2-yl)pyrimidin-2-yl]-5-fluoro-isoindoline (14-3)

POCl$_3$ (149 μL, 1.6 mmol) was dropwise added to a mixture of 2-[2-(5-fluoroisoindolin-2-yl)pyrimidin-4-yl]pyrimidin-4-ol (14-3, 25 mg, 0.08 mmol) in 1,2-dichloroethane (DCE, 1 mL). The resulting mixture was stirred at 80° C. for 1 h. After cooled down to room temperature, the solvent was removed under reduced pressure and the residue was taken up with ethyl acetate (5 mL), washed with saturated sodium bicarbonate (3 mL). The organic layer was dried over MgSO$_4$, filtered, and concentrated. The residue was purified by silica gel chromatography (eluted with 5% MeOH in DCM) to give 2-[4-(4-chloropyrimidin-2-yl)pyrimidin-2-yl]-5-fluoro-isoindoline (14-3, 14 mg, yield: 53%). $^1$H-NMR (300 MHz, CDCl$_3$): δ (ppm): 8.85 (m, 1H), 8.6 (m, 1H), 7.62 (m, 1H), 7.43 (m, 1H), 7.28 (m, 1H), 7.03 (m, 2H), 5.02 (br, 4H). MS (ESI$^+$): m/z: 328.2 (M+H, $^{35}$Cl)$^+$, 330.2 (M+H, $^{37}$Cl)$^+$.

Step 3: (E)-5-Fluoro-2-(4-(2-(pyridine-4-yl)vinyl)-[2,4'-bipyrimidin]-2'-yl)isoindoline (Ex. 14)

A mixture of 2-[4-(4-chloropyrimidin-2-yl)pyrimidin-2-yl]-5-fluoro-isoindoline (14-3, 14 mg, 0.04 mmol), 4-[(E)-2-(tetramethyl-1,3,2-dioxaborolan-2-yl)ethenyl]pyridine (14-4, prepared according to WO2010/115279, 30 mg, 0.13 mmol), Pd(PPh$_3$)$_4$ (9.2 mg, 0.008 mmol), and cesium carbonate (78.2 mg, 0.24 mmol) in a mixture dioxane and water (5:1, 1 mL) was degassed and backfilled with nitrogen three times. The resulting mixture was stirred at 100° C. for 12 h under nitrogen. After cooled down to room temperature, the reaction mixture was extracted with ethyl acetate (2×5 mL). The organic layers were combined, dried over MgSO$_4$, filtered, and concentrated. The residue was purified by silica gel chromatography (eluted with 3% MeOH in DCM) to give (E)-5-fluoro-2-(4-(2-(pyridine-4-yl)vinyl)-[2,4'-bipyrimidin]-2'-yl)isoindoline (Ex. 14). $^1$H-NMR (300 MHz, DMSO-d$_6$): δ (ppm): 9.03 (m, 1H), 8.64 (m, 3H), 8.01 (m, 1H), 7.72 (m, 5H), 7.46 (m, 1H), 7.29 (m, 1H), 7.17 (m, 1H), 4.91 (br, 4H). MS (ESI$^+$): m/z: 397.2 (M+H)$^+$.

The foregoing are merely exemplary of synthetic routes to the compound of the invention. The foregoing compounds, compositions and methods of the invention are illustrated by the following examples, which are merely exemplary of aspects of the invention and are not limiting.

2) Biological Activity:

1. ROCK1 and ROCK2 Kinase Assays:

The ROCK1 and ROCK2 kinase binding affinities of compounds in this invention were determined by DiscoverX's KINOMEscan™ KdELECT technology (https://www.discoverx.com/kinomescan-elect-kinase-screening-and-profiling-services): Kinase-tagged T7 phage strains were prepared in an E. coli host derived from the BL21 strain. E. coli were grown to log-phase and infected with T7 phage and incubated with shaking at 32° C. until lysis. The lysates were centrifuged and filtered to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce nonspecific binding. Binding reactions were assembled by combining kinases, liganded affinity beads, and test compounds in 1× binding buffer (20% SeaBlock, 0.17×PBS, 0.05% Tween 20, 6 mM DTT). Test compounds were prepared as 11 IX stocks in 100% DMSO. Kds were determined using an I 1-point 3-fold compound dilution series with three DMSO control points. All compounds for Kd measurements are distributed by acoustic transfer (non-contact dispensing) in 100% DMSO. The compounds were then diluted directly into the assays such that the final concentration of DMSO was 0.9%. All reactions performed in polypropylene 384-well plate. Each was a final volume of 0.02 ml. The assay plates were incubated at room temperature with shaking for 1 hour and the affinity beads were washed with wash buffer (lx PBS, 0.05% Tween 20). The beads were then re-suspended in elution buffer (lx PBS, 0.05% Tween 20, 0.5 μM non-biotinylated affinity ligand) and incubated at room temperature with shaking for 30 minutes. The kinase concentration in the eluates was measured by qPCR.

The testing results of the equilibrium dissociation constant (Kd) of selected compounds of this invention are shown in the following table. The data for the reference compound KD025 were generated in the same assays for comparison.

| | Kd (μM) | |
|---|---|---|
| Compound | ROCK1 | ROCK2 |
| KD025 | 13.0 | 0.12 |
| Ex. 1 | >30 | 0.14 |
| Ex. 2 | >30 | 17.0 |
| Ex. 3 | >30 | >30 |
| Ex. 4 | 8.0 | 1.8 |
| Ex. 5 | >30 | 2.0 |
| Ex. 6 | >30 | 0.12 |
| Ex. 7 | >30 | 0.91 |
| Ex. 8 | 0.68 | 0.11 |
| Ex. 9 | 2.40 | 0.085 |
| Ex. 11 | 1.10 | 0.11 |
| Ex. 12 | 15.0 | 0.18 |
| Ex. 13 | 13.0 | 0.13 |
| Ex. 14 | 26.0 | 1.20 |

The data show compounds of this invention bind to both ROCK1 and ROCK2, especially the latter.

2. Arterial Pressure:

The procedure was below:

Animal Study:

The experiments were performed on male CD-1 mice (10-11 week-old), purchased from Charles River Laboratories, MA. After arrival, the animals were housed in the Angion Biomedica animal care facility and allowed 5 days for acclimatization in room having an ambient temperature of 23±2° C. and 12 hr dark/light cycle. The animals were fed normal rodent chow and tap water was provided ad libitum. All the animal experimental protocols were approved by the Institutional Animal Care and Use Committee at the Angion Biomedica.

Bile Duct Ligation:

For bile duct ligation (BDL), we performed midline laparotomy of a length of approximately 1.5-2 cm by cutting the cutis plus fascia with a blunt end surgical scissor. The bile duct was then exposed by caudal movement of the gut. The bile duct was carefully separated from the flanking portal vein and hepatic artery using a fine spring scissor. A 4-0 suture was placed around the bile duct and tied it with two surgical knots. After the surgery, the end of sutures was cut and sternum was lowered. We applied 0.9% saline solution to rinse the peritoneal cavity. Finally, the abdominal layers were closed with 5-0 silk sutures and buprenorphine (1.2 mg/kg body weight) was administered subcutaneously. Animals were allowed to recover under heating pads and were monitored closely for signs of discomfort or pain.

After 24 hrs of bile duct ligation, the CD-1 mice (N=8-10 per group,) were treated with normal saline as vehicle and the Fasudil (10 mg/kg/body weight) and Compound of Ex. 1 (10 mg/kg body weight) groups were treated orally (BID) for 10 days. The control mice underwent sham surgery and were administered saline. After 10 days of treatment, animals were anesthetized and mean arterial pressure was measured.

Mean Arterial Pressure:

Mice were anaesthetized using isoflurane. The carotid artery was cannulated using fluid filled pressure catheter for blood pressure measurement and connected to an ADI data-acquisition system (ADI instruments, CO). Prior to surgery, all the instruments were sterilized using dry beads and soaked in 70% ethanol overnight. On the day of blood pressure measurement, the animals were anesthetized using isoflurane (3% induction and 1% maintenance). Betadine and alcohol swabs were used to disinfect the surgical area. The animals were maintained on heating pads throughout the surgery and temperature was recorded by inserting a temperature probe in the rectum. For blood pressure measurement, a 2 cm incision was made from pelvis to xiphoid process and underlying tissues was dissected carefully. The right carotid artery was exposed using fine forceps. A small incision was made using 26 gauge needle and a fluid filled pressure catheter (ADI instruments, CO) was guided through the carotid artery into the aortic arch. After 15 min of stabilization, the blood pressure was recorded, and the data was analyzed using Lab Chart v7 software (ADI instruments, CO).

Result:

Compared to control, no change in blood pressure was observed in the BDL-vehicle groups. Treatment with fasudil significantly decreased the blood pressure (~26 mm Hg) in the BDL-group while Ex. 1 did not cause any change in mean arterial blood pressure.

3. Biliary Obstruction Model.

Figure 1:
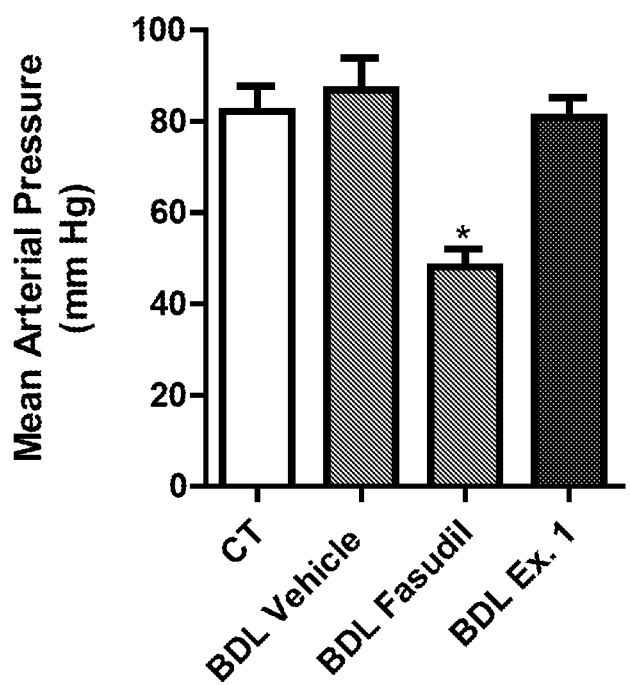
FIG. 1 shows the effect of a compound of the invention on mean arterial pressure in a biliary obstruction model.

Adult male C57BLU6 mice were submitted to standard bile duct ligation (BDL model: Luo, W., Meng, Y., Ji, H. L., Pan, C. Q., Huang, S., Yu, C. H., Xiao, L. M., Cui, K., Ni, S. Y., Zhang, Z. S., Li, X. Spironolactone lowers portal hypertension by inhibiting liver fibrosis, ROCK-2 activity and activating NO/PKG pathway in the bile-duct-ligated rat. *PLoS One* 2012, 7(3), e34230) and treated with vehicle (n=7; 50% PEG300+10% tween 80+40% saline, the formulation for Ex. 1) or Ex. 1 (n=3; 10 mg/kg, PO, BID), starting a day after BDL surgery. In this study, animals were sacrificed 9 days after BDL. A subset of BDL animals was treated with fasudil (n=2; 10 mg/kg, PO, BID) to compare hemodynamic effects (on day 9) of a ROCK2-selective inhibitor vs. a dual ROCK1/2 inhibitor in this model of liver injury/disease. A sham group served as control. As seen in FIG. 1, MAP in sham, BDL+vehicle and BDL+Ex. 1 cohorts was not different. By contrast, the fasudil cohort exhibited decreased MAP.

Figure 2:
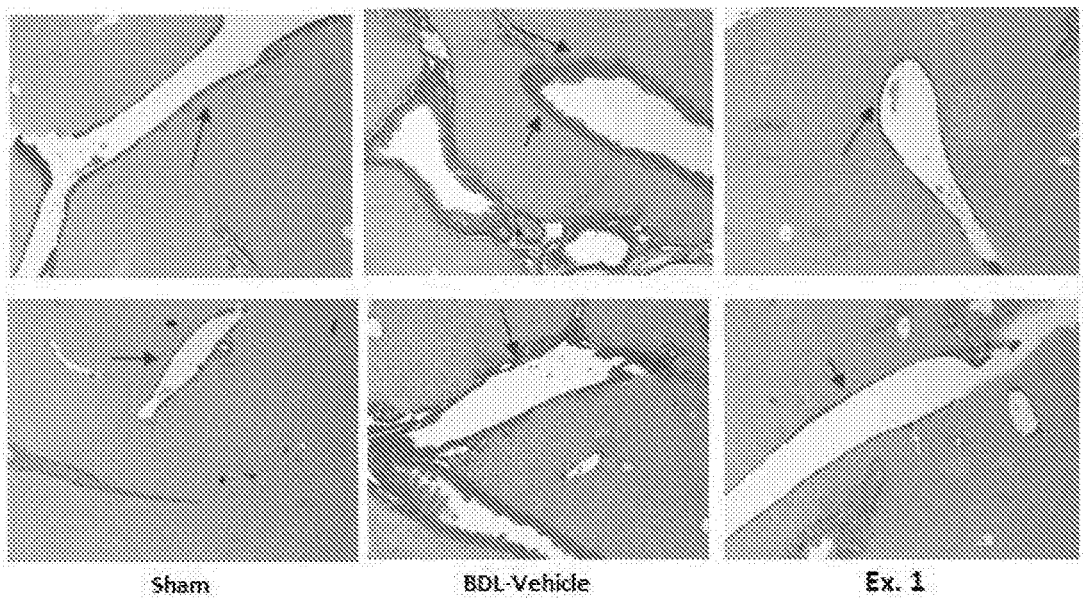
FIG. 2 shows the effect of a compound of the invention on bile duct media wall thickness in histological sections from the same model.
Figure 3:
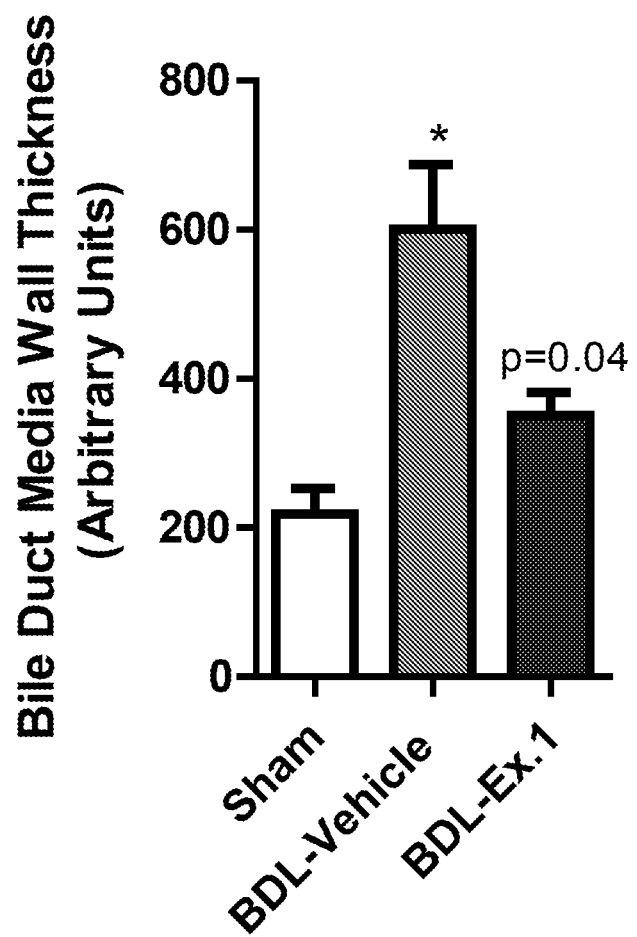
FIG. 3 shows a comparison of wall thickness values in the same model.

The BDL model is a model of cholestatic injury and is associated with both inflammation and biliary sclerosis. This was evident even by day 9 in the BDL+vehicle-treated cohort (p<0.01 vs. sham). Treatment with a representative compound of this invention Ex. 1 was associated with a reduction in biliary thickening (H&E histological sections, FIG. 2; quantitative analysis, FIG. 3). Treatment with a compound of the invention was also associated with a reduction in biliary inflammation (H&E sections, FIG. 4A) and the necro-inflammatory score (FIG. 4B).

What is claimed is:
1. A compound of formula Ic:

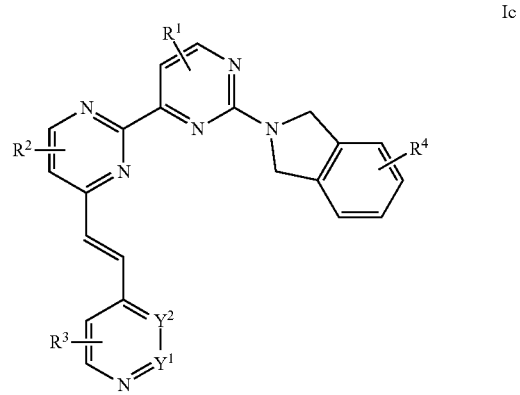

or a pharmaceutically acceptable salt thereof, wherein
$Y^1$ and $Y^2$ are each independently N or C-$R^3$, wherein two $R^3$ groups together with the carbons they are attached to may optionally form a 3-7 membered aromatic, heteroaromatic, or heterocyclic ring, optionally contain 1-5 additional heteroatoms selected from O, S(O)$_w$, or N as the ring atoms, and may be optionally substituted with one or more hydrogen, deuterium, halo, —CN, —NO$_2$, —OH, —CH$_2$F, —CHF$_2$, —OCH$_3$, —OCH$_2$F, —OCHF$_2$, —NHCH$_3$, —N(CH$_3$)$_2$, —CO$_2$H, —SH, —S(O)$_w$CH$_3$, or an aliphatic, alicyclic, heteroaliphatic, heterocyclic ring, aromatic ring, or heteroaromatic ring;

$R^1$, $R^2$, and $R^3$ each independently represents one, two, three, or four same or different substituents selected from hydrogen, deuterium, halo, —CN, —NO$_2$, aliphatic, alicyclic, heteroaliphatic, heterocyclic ring, aromatic ring, heteroaromatic ring, —OR$^a$, —NR$^b$R$^c$, —S(=O)$_w$R$^d$, —O—S(=O)$_w$R$^d$, —S(=O)$_w$NR$^e$R$^f$, —C(=O)R$^g$, —CO$_2$R$^h$, —CONR$^i$R$^j$, —NR$^k$CONR$^l$R$^m$, —)CONR$^n$R$^o$, or —NR$^p$CO$_2$R$^q$;

$R^4$ represents one, two, three, or four substituents independently selected from hydrogen, deuterium, halo, —CN, —NO$_2$, aliphatic, alicyclic, heteroaliphatic, heterocyclic ring, aromatic ring, heteroaromatic ring, —OR$^a$, —NR$^b$R$^c$, —S(=O)$_w$R$^d$, —O—S(↑O)$_w$R$^d$, —S(=O)$_w$NR$^e$R$^f$, —C(=O)R$^g$, —CO$_2$R$^h$, —CONR$^i$R$^j$, —NR$^k$CONR$^l$R$^m$, —OCONR$^n$R$^o$, or —NR$^k$CO$_2$R$^p$;

$R^a$, $R^b$, $R^c$, $R^d$, $R^e$, $R^f$, $R^g$, $R^h$, $R^i$, $R^j$, $R^k$, $R^l$, $R^m$, $R^n$, $R^o$, $R^p$, and $R^q$, for each occurrence, is independently selected from hydrogen, deuterium, halo, —CN, —NO$_2$, or an optionally substituted aliphatic, alicyclic, heteroaliphatic, heterocyclic ring, aromatic ring, or heteroaromatic ring, wherein the optional substituents are selected from hydrogen, deuterium, halo, —CN, —NO$_2$, aliphatic, alicyclic, heteroaliphatic, heterocyclic ring, aromatic ring, heteroaromatic ring, —OR$^{aa}$, —NR$^{bb}$R$^{cc}$, —S(=O)$_w$R$^{dd}$, —S(=O)$_w$NR$^{ee}$R$^{ff}$, —C(=O)R$^{gg}$, —CO$_2$R$^{hh}$, —CONR$^{ii}$R$^{jj}$, —NR$^{kk}$CONR$^{ll}$R$^{mm}$, —OCONR$^{mm}$R$^{oo}$, or —NR$^{kk}$CO$_2$R$^{pp}$; or R$^b$ and R$^c$, R$^e$ and R$^f$, R$^i$ and R$^j$, R$^l$ and R$^m$, or R$^n$ and R$^o$, when attached to the same nitrogen, may optionally form a heterocyclic ring, optionally containing 1-5 additional heteroatoms selected from O, S(O)$_w$, or N as the ring atoms, and may be optionally substituted with one or more hydrogen, deuterium, halo, —CN, —NO$_2$, aliphatic, alicyclic, heteroaliphatic, heterocyclic ring, aromatic ring, or heteroaromatic ring;

$R^{aa}$, $R^{bb}$, $R^{cc}$, $R^{dd}$, $R^{ee}$, $R^{ff}$, $R^{gg}$, $R^{hh}$, $R^{ii}$, $R^{jj}$, $R^{kk}$, $R^{ll}$, $R^{mm}$, $R^{nn}$, $R^{oo}$, and $R^{pp}$, for each occurrence, is independently selected from hydrogen, deuterium, halo, —CN, —NO$_2$, —OH, —CH$_2$F, —CHF$_2$, —CF$_3$, —OCH$_3$, —OCH$_2$F, —OCHF$_2$, —OCF$_3$, —NH$_2$, —NHCH$_3$, —N(CH$_3$)$_2$, —CO$_2$H, —SH, —S(O)$_w$CH$_3$, aliphatic, alicyclic, heteroaliphatic, heterocyclic ring, aromatic ring, or heteroaromatic ring; and each w is independently 0, 1, or 2.

2. The compound of claim 1 or a pharmaceutically acceptable salt thereof, wherein the compound is selected from the following:

(E)-5-Methoxy-2-(4-(2-(pyridin-4-yl)vinyl)-[2,4'-bipyrimidin]-2'-yl)isoindoline

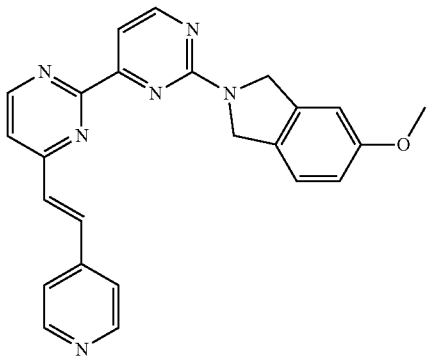 [SMILES: COc1ccc2c(c1)CN(c1nccc(-c3nccc(/C=C/c4ccncc4)n3)n1)C2]

(E)-4-(2-(2'-(5-Methoxyisoindolin-2-yl)-[2,4'-bipyrimidin]-4-yl)vinyl)quinoline

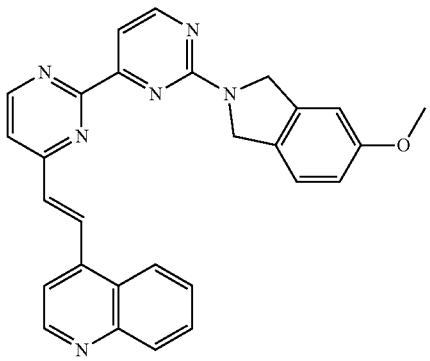 [SMILES: COc1ccc2c(c1)CN(c1nccc(-c3nccc(/C=C/c4ccnc5ccccc45)n3)n1)C2]

(E)-4-(2-(2'-(5-Methoxyisoindolin-2-yl)-[2,4'-bipyrimidin]-4-yl)vinyl)-1H-pyrrolo[2,3-b]pyridine

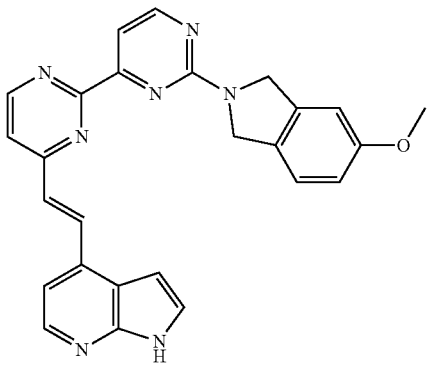 [SMILES: COc1ccc2c(c1)CN(c1nccc(-c3nccc(/C=C/c4ccnc5[nH]ccc45)n3)n1)C2]

(E)-4-(2-(2'-(5-Methoxyisoindolin-2-yl)-[2,4'-bipyrimidin]-4-yl)vinyl)pyrimidin-2-amine

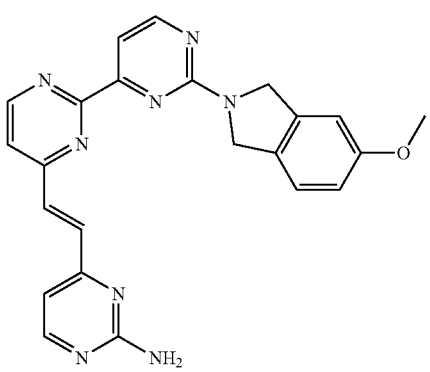

(E)-2-(4-(2-(Pyridin-4-yl)vinyl)-[2,4'-bipyrimidin]-2'-yl)isoindolin-5-ol
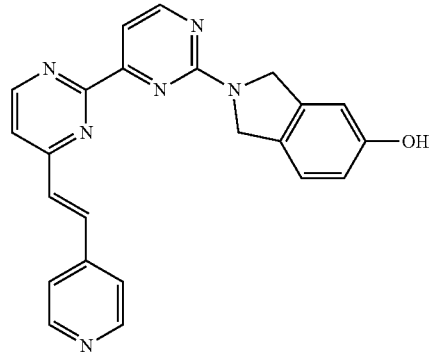 [SMILES: Oc1ccc2c(c1)CN(c1nccc(-c3nccc(/C=C/c4ccncc4)n3)n1)C2]
(E)-2-(4-(2-(Pyridin-4-yl)vinyl)-[2,4'-bipyrimidin]-2'-yl)isoindolin-5-yl trifluoromethanesulfonate
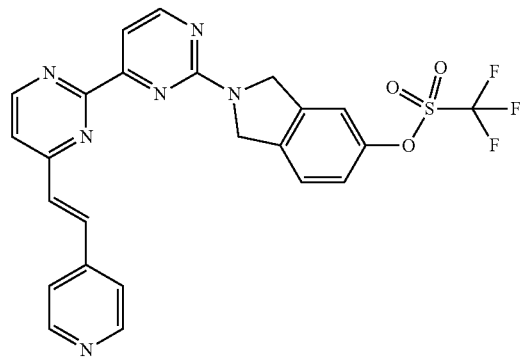 [SMILES: O=S(=O)(Oc1ccc2c(c1)CN(c1nccc(-c3nccc(/C=C/c4ccncc4)n3)n1)C2)C(F)(F)F]
(E)-2-(4-(2-(Pyridin-4-yl)vinyl)-[2,4'-bipyrimidin]-2'-yl)isoindoline-5-carbonitrile
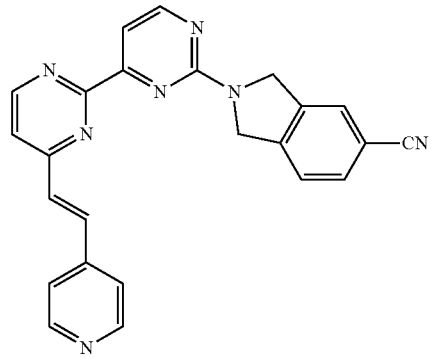
(E)-N,N-Dimethyl-2-((2-(4-(2-(pyridin-4-yl)vinyl)-[2,4'-bipyrimidin]-2'-yl)isoindolin-5-yl)oxy)ethanamine
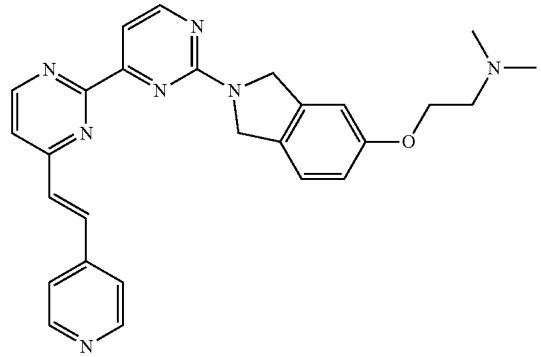 [SMILES: CN(C)CCOc1ccc2c(c1)CN(c1nccc(-c3nccc(/C=C/c4ccncc4)n3)n1)C2]

(E)-Methyl-2-((2-(4-(2-(pyridin-4-yl)vinyl)-[2,4'-bipyrimidin]-2'-yl)isoindolin-5-yl)oxy)acetate
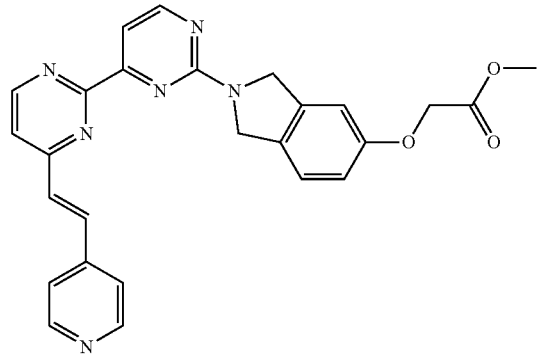 [SMILES: COC(=O)COc1ccc2c(c1)CN(c1nccc(-c3nccc(/C=C/c4ccncc4)n3)n1)C2]
(E)-N-Methyl-2-((2-(4-(2-(pyridin-4-yl)vinyl)-[2,4'-bipyrimidin]-2'-yl)isoindolin-5-yl)oxy)acetamide
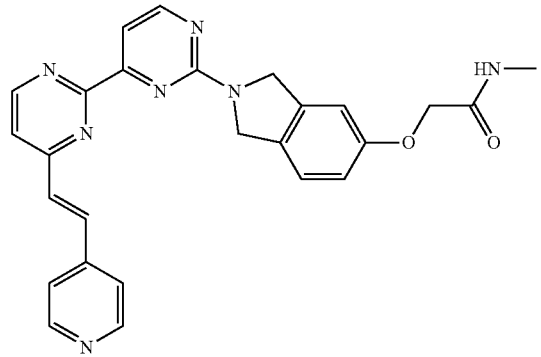 [SMILES: CNC(=O)COc1ccc2c(c1)CN(c1nccc(-c3nccc(/C=C/c4ccncc4)n3)n1)C2]
(E)-N-Ethyl-2-((2-(4-(2-(pyridin-4-yl)vinyl)-[2,4'-bipyrimidin]-2'-yl)isoindolin-5-yl)oxy)acetamide
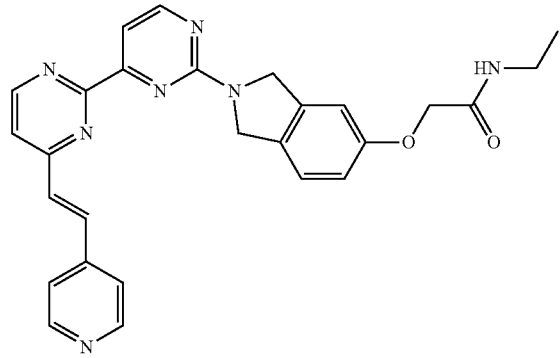
(E)-N-Isopropyl-2-((2-(4-(2-(pyridin-4-yl)vinyl)-[2,4'-bipyrimidin]-2'-yl)isoindolin-5-yl)oxy)acetamide
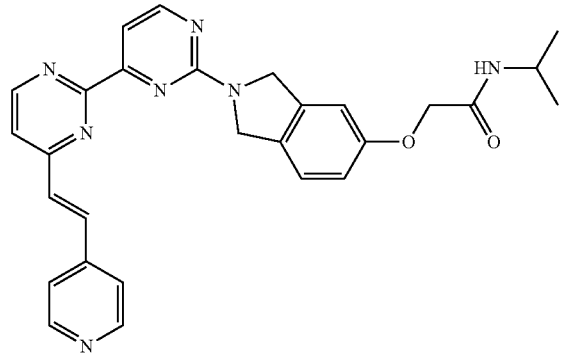 [SMILES: CC(C)NC(=O)COc1ccc2c(c1)CN(c1nccc(-c3nccc(/C=C/c4ccncc4)n3)n1)C2]

(E)-5-Fluoro-2-(4-(2-(pyridin-4-yl)vinyl)-[2,4'-bipyrimidin]-2'-yl)isoindoline
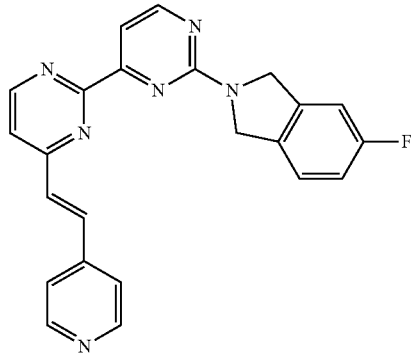 [SMILES: Fc1ccc2c(c1)CN(c1nccc(-c3nccc(/C=C/c4ccncc4)n3)n1)C2]
(E)-5-Chloro-2-(4-(2-(pyridin-4-yl)vinyl)-[2,4'-bipyrimidin]-2'-yl)isoindoline
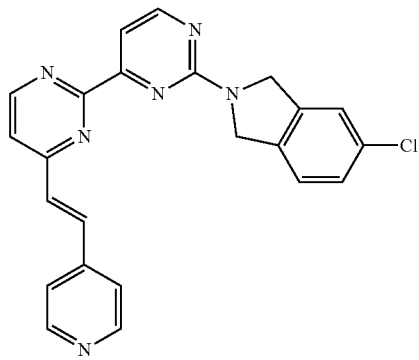 [SMILES: Clc1ccc2c(c1)CN(c1nccc(-c3nccc(/C=C/c4ccncc4)n3)n1)C2]
(E)-5-Bromo-2-(4-(2-(pyridin-4-yl)vinyl)-[2,4'-bipyrimidin]-2'-yl)isoindoline
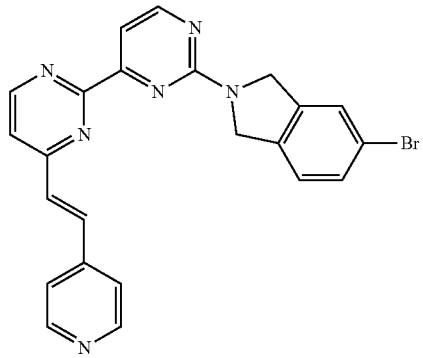 [SMILES: Brc1ccc2c(c1)CN(c1nccc(-c3nccc(/C=C/c4ccncc4)n3)n1)C2]
(E)-5-Iodo-2-(4-(2-(pyridin-4-yl)vinyl)-[2,4'-bipyrimidin]-2'-yl)isoindoline
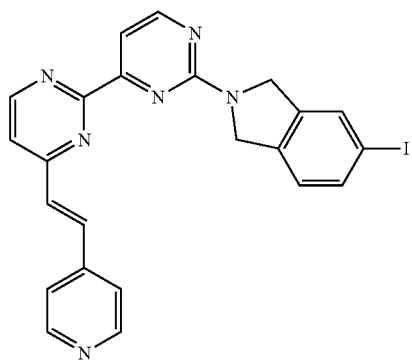 [SMILES: Ic1ccc2c(c1)CN(c1nccc(-c3nccc(/C=C/c4ccncc4)n3)n1)C2]

(E)-5-Ethoxy-2-(4-(2-(pyridin-4-yl)vinyl)-[2,4'-bipyrimidin]-2'-yl)isoindoline
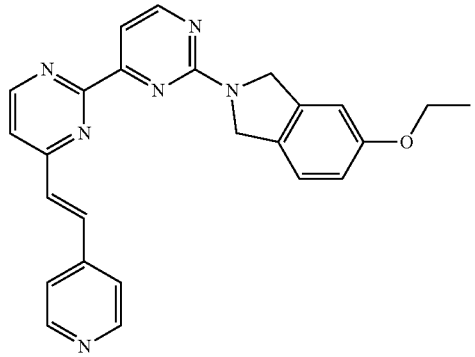
(E)-5-Isopropoxy-2-(4-(2-(pyridin-4-yl)vinyl)-[2,4'-bipyrimidin]-2'-yl)isoindoline
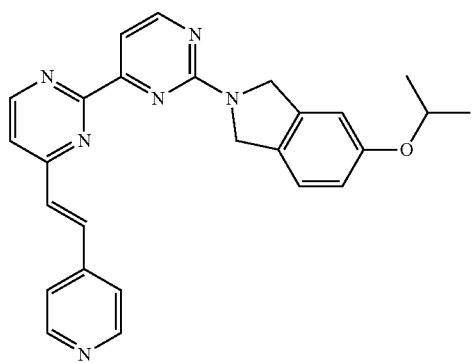 [SMILES: CC(C)Oc1ccc2c(c1)CN(c1nccc(-c3nccc(/C=C/c4ccncc4)n3)n1)C2]
(E)-5-Cyclopropoxy-2-(4-(2-(pyridin-4-yl)vinyl)-[2,4'-bipyrimidin]-2'-yl)isoindoline
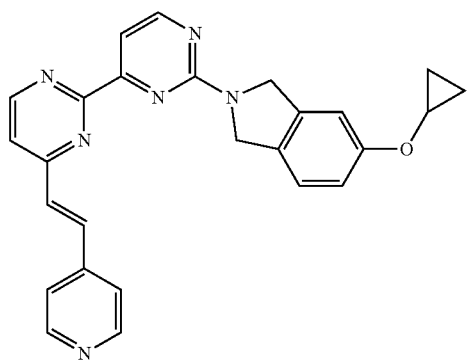 [SMILES: C(=C\c1ccnc(-c2ccnc(N3Cc4ccc(OC5CC5)cc4C3)n2)n1)/c1ccncc1]
(E)-5-Methyl-2-(4-(2-(pyridin-4-yl)vinyl)-[2,4'-bipyrimidin]-2'-yl)isoindoline
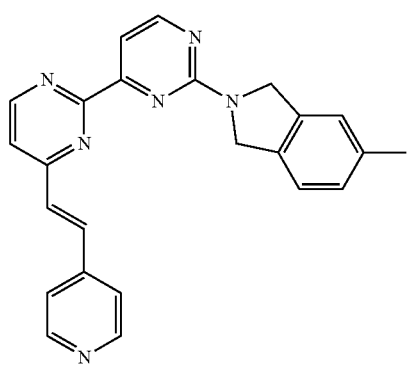 [SMILES: Cc1ccc2c(c1)CN(c1nccc(-c3nccc(/C=C/c4ccncc4)n3)n1)C2]

(E)-5-Ethyl-2-(4-(2-(pyridin-4-yl)vinyl)-[2,4'-bipyrimidin]-2'-yl)isoindoline
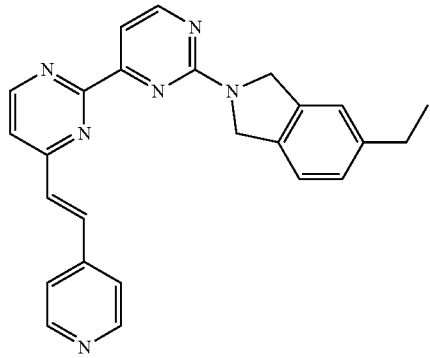 [SMILES: CCc1ccc2c(c1)CN(c1nccc(-c3nccc(/C=C/c4ccncc4)n3)n1)C2]
(E)-5-Cyclopropyl-2-(4-(2-(pyridin-4-yl)vinyl)-[2,4'-bipyrimidin]-2'-yl)isoindoline
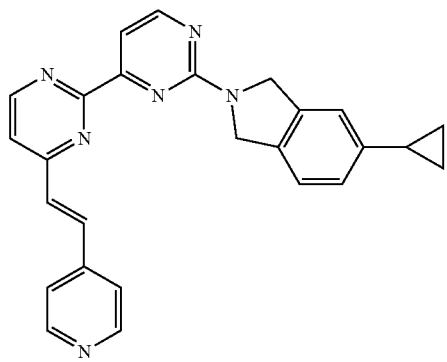 [SMILES: C(=C\c1ccnc(-c2ccnc(N3Cc4ccc(C5CC5)cc4C3)n2)n1)/c1ccncc1]
(E)-5-Amino-2-(4-(2-(pyridin-4-yl)vinyl)-[2,4'-bipyrimidin]-2'-yl)isoindoline
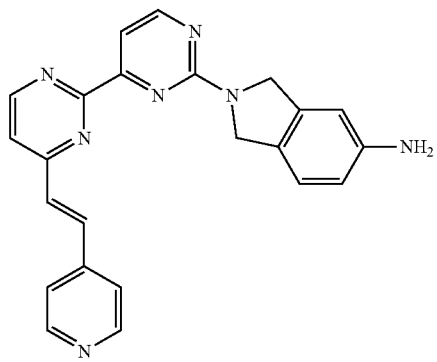 [SMILES: Nc1ccc2c(c1)CN(c1nccc(-c3nccc(/C=C/c4ccncc4)n3)n1)C2]
(E)-5-Methylamino-2-(4-(2-(pyridin-4-yl)vinyl)-[2,4'-bipyrimidin]-2'-yl)isoindoline
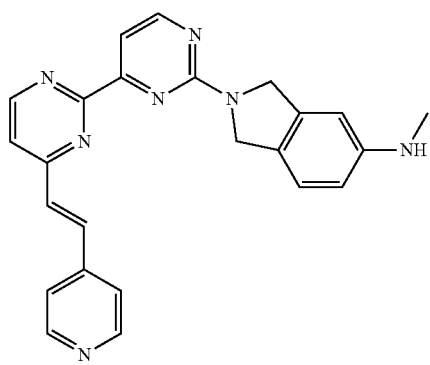 [SMILES: CNc1ccc2c(c1)CN(c1nccc(-c3nccc(/C=C/c4ccncc4)n3)n1)C2]

(E)-5-Dimethylamino-2-(4-(2-(pyridin-4-yl)vinyl)-[2,4'-bipyrimidin]-2'-yl)isoindoline
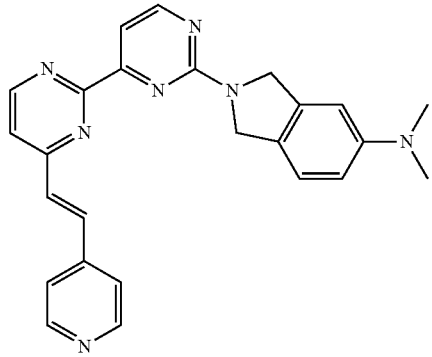 [SMILES: CN(C)c1ccc2c(c1)CN(c1nccc(-c3nccc(/C=C/c4ccncc4)n3)n1)C2]
(E)-5-Vinyl-2-(4-(2-(pyridin-4-yl)vinyl)-[2,4'-bipyrimidin]-2'-yl)isoindoline
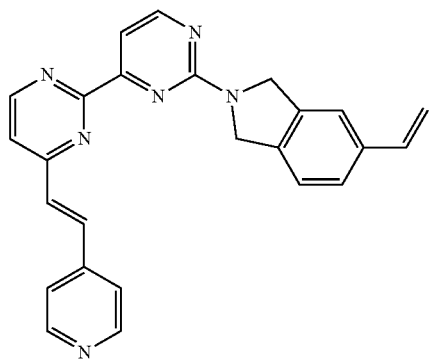 [SMILES: C=Cc1ccc2c(c1)CN(c1nccc(-c3nccc(/C=C/c4ccncc4)n3)n1)C2]
(E)-5-Propargyl-2-(4-(2-(pyridin-4-yl)-vinyl)-[2,4'-bipyrimidin]-2'-yl)isoindoline
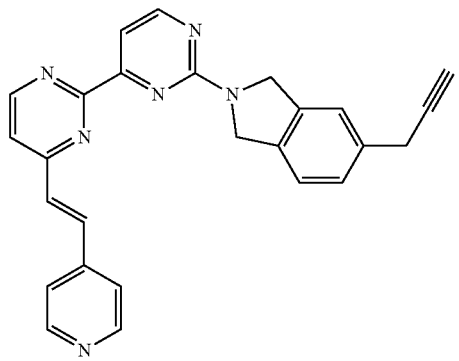 [SMILES: C#CCc1ccc2c(c1)CN(c1nccc(-c3nccc(/C=C/c4ccncc4)n3)n1)C2]
N-Methyl-2-[4-[4-[(E)-2-(4-pyridyl)vinyl]pyrimidin-2-yl]pyrimidin-2-yl]isoindoline-5-carboxamide
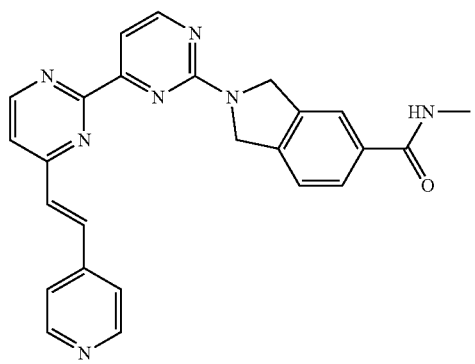 [SMILES: CNC(=O)c1ccc2c(c1)CN(c1nccc(-c3nccc(/C=C/c4ccncc4)n3)n1)C2]

| | |
|---|---|
| N-Ethyl-2-[4-[4-[(E)-2-(4-pyridyl)vinyl]pyrimidin-2-yl]pyrimidin-2-yl]isoindoline-5-carboxamide | 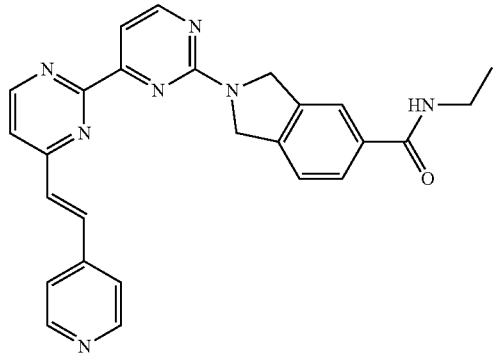 [SMILES: CCNC(=O)c1ccc2c(c1)CN(c1nccc(-c3nccc(/C=C/c4ccncc4)n3)n1)C2] |
| N-Isopropyl-2-[4-[4-[(E)-2-(4-pyridyl)vinyl]pyrimidin-2-yl]pyrimidin-2-yl]isoindoline-5-carboxamide | 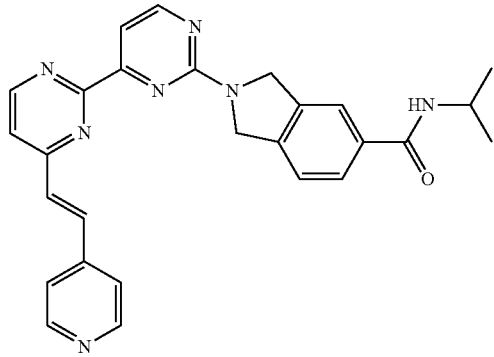 [SMILES: CC(C)NC(=O)c1ccc2c(c1)CN(c1nccc(-c3nccc(/C=C/c4ccncc4)n3)n1)C2] |
| N-Cyclopropyl-2-[4-[4-[(E)-2-(4-pyridyl)vinyl]pyrimidin-2-yl]pyrimidin-2-yl]isoindoline-5-carboxamide | 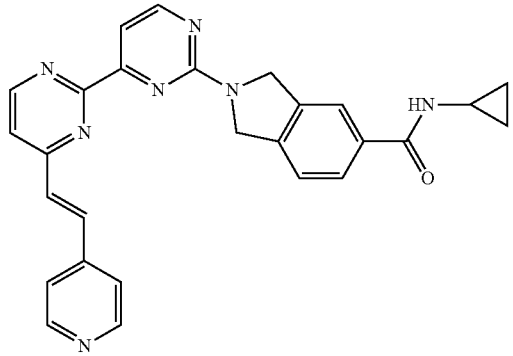 [SMILES: O=C(NC1CC1)c1ccc2c(c1)CN(c1nccc(-c3nccc(/C=C/c4ccncc4)n3)n1)C2] |
| N-(tert-Butyl)-2-[4-[4-[(E)-2-(4-pyridyl)vinyl]pyrimidin-2-yl]pyrimidin-2-yl]isoindoline-5-carboxamide | 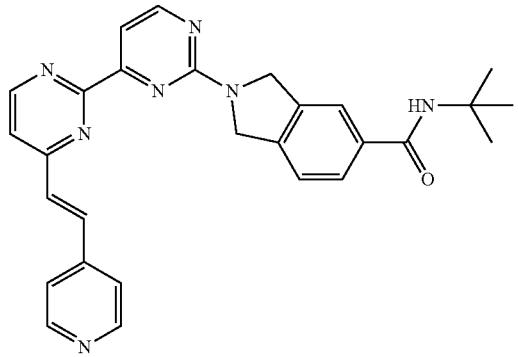 [SMILES: CC(C)(C)NC(=O)c1ccc2c(c1)CN(c1nccc(-c3nccc(/C=C/c4ccncc4)n3)n1)C2] |

N',N'-Dimethyl-N-[2-[4-[4-[(E)-2-(4-pyridyl)vinyl]pyrimidin-2-yl]pyrimidin-2-yl]isoindolin-5-yl]ethane-1,2-diamine
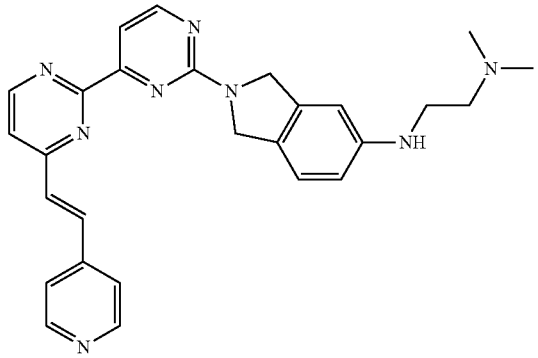 [SMILES: CN(C)CCNc1ccc2c(c1)CN(c1nccc(-c3nccc(/C=C/c4ccncc4)n3)n1)C2]
N',N',N'-Trimethyl-N'-[2-[4-[4-[(E)-2-(4-pyridyl)vinyl]pyrimidin-2-yl]pyrimidin-2-yl]isoindolin-5-yl]ethane-1,2-diamine
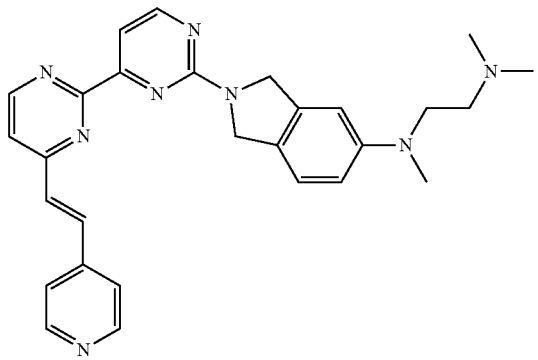 [SMILES: CN(C)CCN(C)c1ccc2c(c1)CN(c1nccc(-c3nccc(/C=C/c4ccncc4)n3)n1)C2]
4-[2-[2-[4-[4-[(E)-2-(4-Pyridyl)vinyl]pyrimidin-2-yl]pyrimidin-2-yl]isoindolin-5-yl]oxyethyl]morpholine
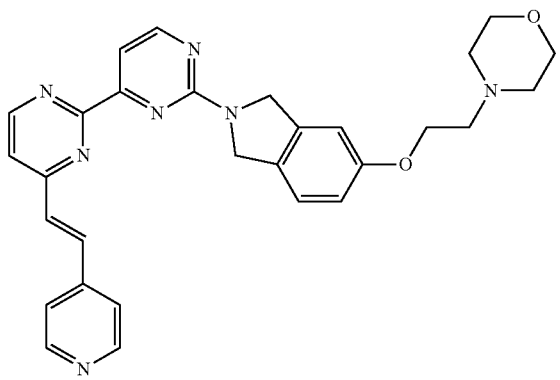 [SMILES: C(=C\c1ccnc(-c2ccnc(N3Cc4ccc(OCCN5CCOCC5)cc4C3)n2)n1)/c1ccncc1]
5-[2-(4-Methylpiperazin-1-yl)ethoxy]-2-[4-[4-[(E)-2-(4-pyridyl)vinyl]pyrimidin-2-yl]pyrimidin-2-yl]isoindoline
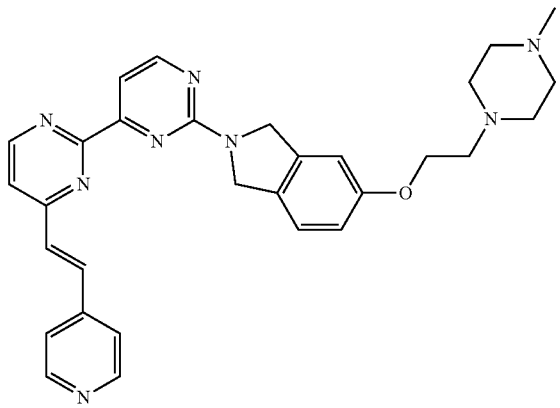 [SMILES: CN1CCN(CCOc2ccc3c(c2)CN(c2nccc(-c4nccc(/C=C/c5ccncc5)n4)n2)C3)CC1]

| | |
|---|---|
| 4-[2-[4-[4-[(E)-2-(4-Pyridyl)vinyl]pyrimidin-2-yl]pyrimidin-2-yl]isoindolin-5-yl]morpholine | 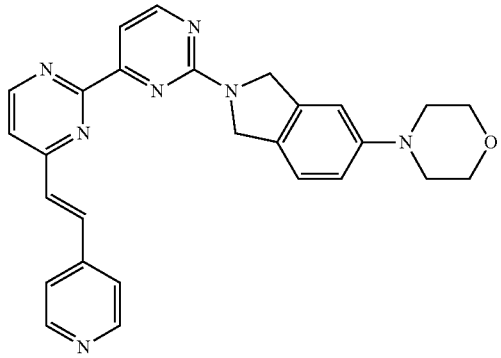 [SMILES: C(=C\c1ccnc(-c2ccnc(N3Cc4ccc(N5CCOCC5)cc4C3)n2)n1)/c1ccncc1] |
| 5-(4-Methylpiperazin-1-yl)-2-[4-[4-[(E)-2-(4-pyridyl)vinyl]pyrimidin-2-yl]pyrimidin-2-yl]isoindoline | 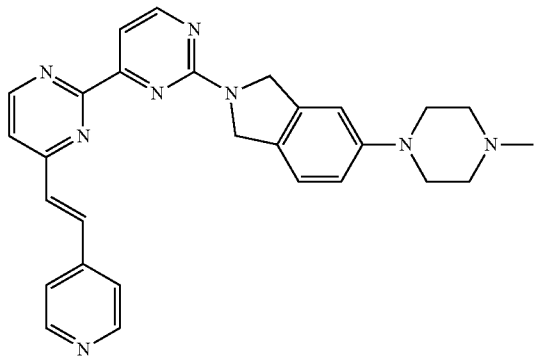 [SMILES: CN1CCN(c2ccc3c(c2)CN(c2nccc(-c4nccc(/C=C/c5ccncc5)n4)n2)C3)CC1] |
| 5-(1-Methylpyrazol-4-yl)-2-[4-[4-[(E)-2-(4-pyridyl)vinyl]pyrimidin-2-yl]pyrimidin-2-yl]isoindoline | 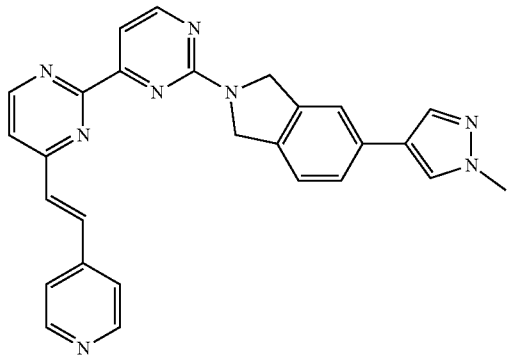 [SMILES: Cn1cc(-c2ccc3c(c2)CN(c2nccc(-c4nccc(/C=C/c5ccncc5)n4)n2)C3)cn1] |
| 5-Phenyl-2-[4-[4-[(E)-2-(4-pyridyl)vinyl]pyrimidin-2-yl]pyrimidin-2-yl]isoindoline | 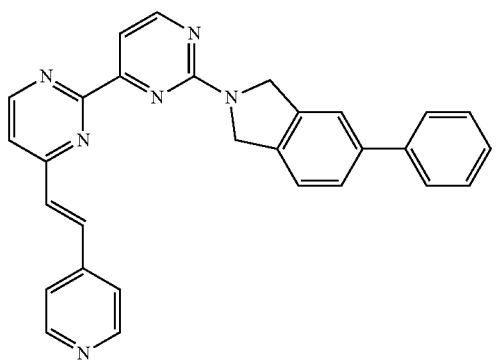 [SMILES: C(=C\c1ccnc(-c2ccnc(N3Cc4ccc(-c5ccccc5)cc4C3)n2)n1)/c1ccncc1] |

| | |
|---|---|
| 4-[(E)-2-[2-[2-(5-Methoxyisoindolin-2-yl)pyrimidin-4-yl]pyrimidin-4-yl]vinyl]pyridin-2-amine | 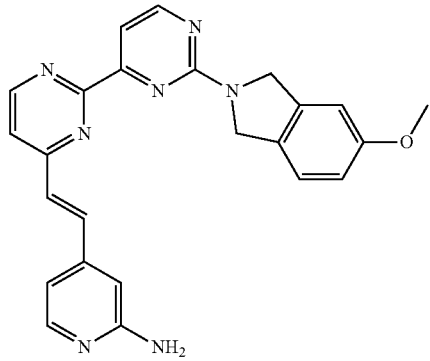 |
| 4-[(E)-2-[2-[2-(5-Fluoroisoindolin-2-yl)pyrimidin-4-yl]pyrimidin-4-yl]vinyl]pyridin-2-amine | 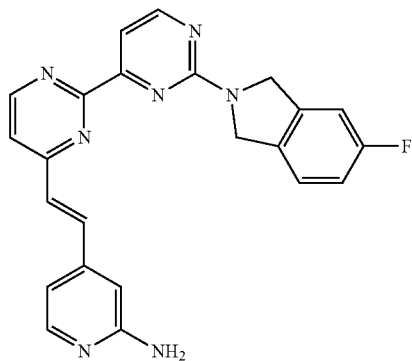 [SMILES: Nc1cc(/C=C/c2ccnc(-c3ccnc(N4Cc5ccc(F)cc5C4)n3)n2)ccn1] |
| 4-[(E)-2-[2-[2-(5-Chloroisoindolin-2-yl)pyrimidin-4-yl]pyrimidin-4-yl]vinyl]pyridin-2-amine | 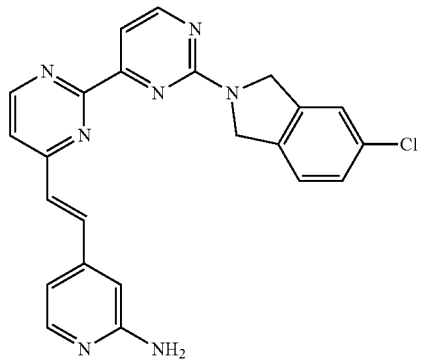 |
| 4-[(E)-2-[2-[2-(5-Bromoisoindolin-2-yl)pyrimidin-4-yl]pyrimidin-4-yl]vinyl]pyridin-2-amine | 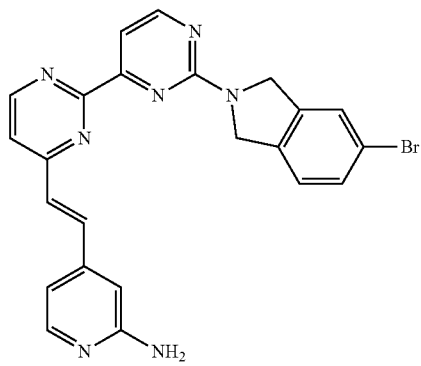 [SMILES: Nc1cc(/C=C/c2ccnc(-c3ccnc(N4Cc5ccc(Br)cc5C4)n3)n2)ccn1] |

-continued
2-[4-[4-[(E)-2-(2-Amino-4-pyridyl)vinyl]pyrimidin-2-yl]pyrimidin-2-yl]isoindoline-5-carbonitrile
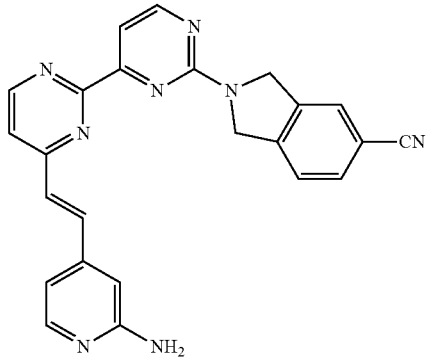 [SMILES: N#Cc1ccc2c(c1)CN(c1nccc(-c3nccc(/C=C/c4ccnc(N)c4)n3)n1)C2]
4-[(E)-2-[2-[2-[5-(4-Methylpiperazin-1-yl)isoindolin-2-yl]pyrimidin-4-yl]pyrimidin-4-yl]vinyl]pyridin-2-amine
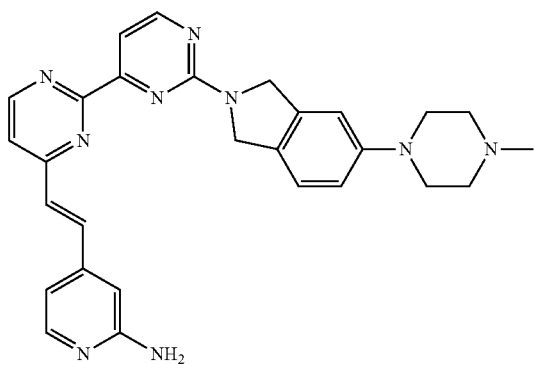 [SMILES: CN1CCN(c2ccc3c(c2)CN(c2nccc(-c4nccc(/C=C/c5ccnc(N)c5)n4)n2)C3)CC1]
4-[(E)-2-[2-[2-(5-Morpholinoisoindolin-2-yl)pyrimidin-4-yl]yrimidin-4-yl]yinyl]pyridin-2-amine
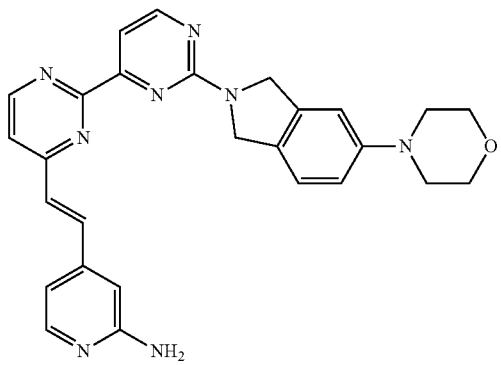 [SMILES: Nc1cc(/C=C/c2ccnc(-c3ccnc(N4Cc5ccc(N6CCOCC6)cc5C4)n3)n2)ccn1]
2-[4-[4-[(E)-2-(2-Amino-4-pyridyl)vinyl]pyrimidin-2-yl]pyrimidin-2-yl]-N-methyl-isoindoline-5-carboxamide
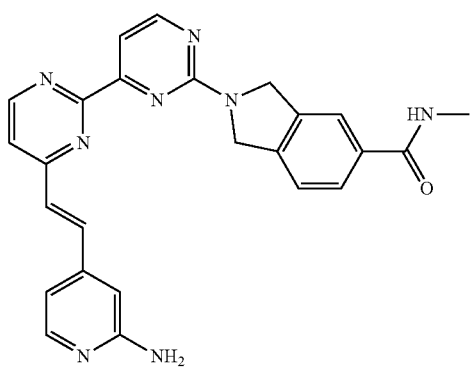 [SMILES: CNC(=O)c1ccc2c(c1)CN(c1nccc(-c3nccc(/C=C/c4ccnc(N)c4)n3)n1)C2]

| | |
|---|---|
| 2-[4-[4-[(E)-2-(2-Amino-4-pyridyl)vinyl]pyrimidin-2-yl]pyrimidin-2-yl]-N-ethyl-isoindoline-5-carboxamide | 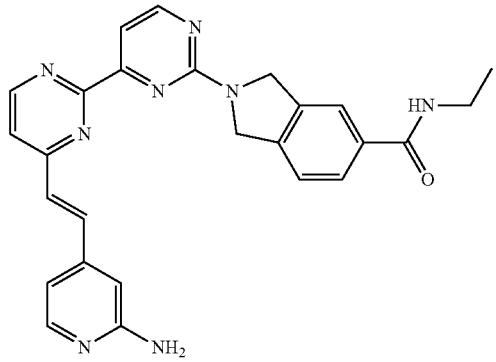 [SMILES: CCNC(=O)c1ccc2c(c1)CN(c1nccc(-c3nccc(/C=C/c4ccnc(N)c4)n3)n1)C2] |
| 2-[4-[4-[(E)-2-(2-Amino-4-pyridyl)vinyl]pyrimidin-2-yl]pyrimidin-2-yl]-N-isopropyl-isoindoline-5-carboxamide | 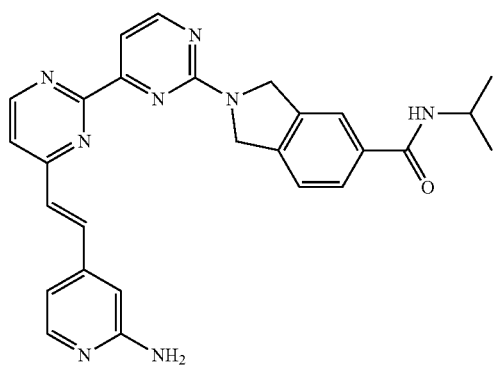 [SMILES: CC(C)NC(=O)c1ccc2c(c1)CN(c1nccc(-c3nccc(/C=C/c4ccnc(N)c4)n3)n1)C2] |
| 4-[(E)-2-[2-[2-[5-[2-(Dimethylamino)ethoxy]isoindolin-2-yl]pyrimidin-4-yl]pyrimidin-4-yl]vinyl]pyridin-2-amine | 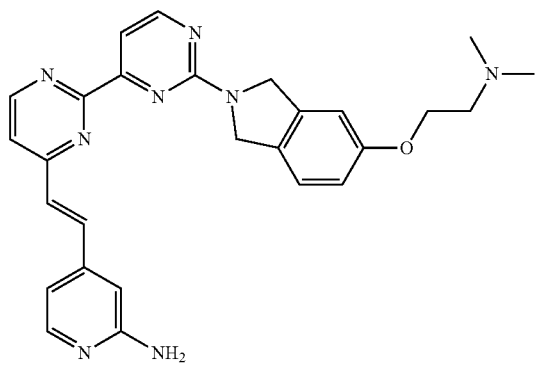 [SMILES: CN(C)CCOc1ccc2c(c1)CN(c1nccc(-c3nccc(/C=C/c4ccnc(N)c4)n3)n1)C2] |
| 4-[(E)-2-[2-[2-[5-(1-Methylpyrazol-4-yl)isoindolin-2-yl]pyrimidin-4-yl]pyrimidin-4-yl]vinyl]pyridin-2-amine | 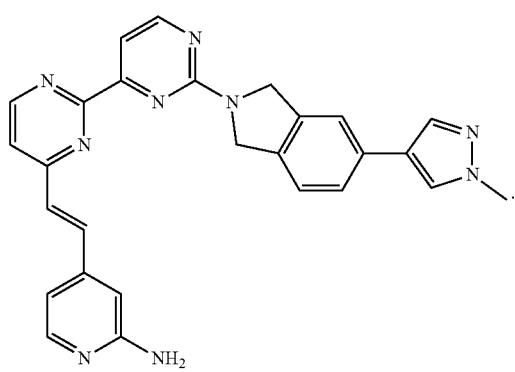 [SMILES: Cn1cc(-c2ccc3c(c2)CN(c2nccc(-c4nccc(/C=C/c5ccnc(N)c5)n4)n2)C3)cn1] |

3. The compound of claim 1 or a pharmaceutically acceptable salt thereof, wherein the compound is selected from the following:

(E)-5-Methoxy-2-(4-(2-(pyridin-4-yl)vinyl)[2,4'-bipyrimidin]-2'-yl)isoindoline

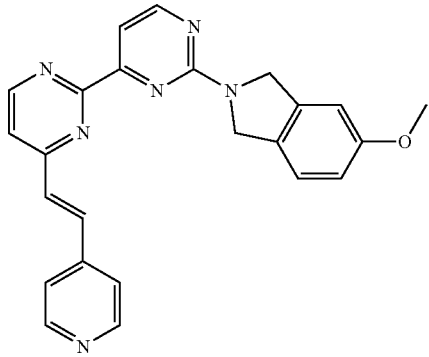 [SMILES: COc1ccc2c(c1)CN(c1nccc(-c3nccc(/C=C/c4ccncc4)n3)n1)C2]

(E)-4-(2-(2'-(5-Methoxyisoindolin-2-yl)-[2,4'-bipyrimidin]-4-yl)vinyl)quinoline

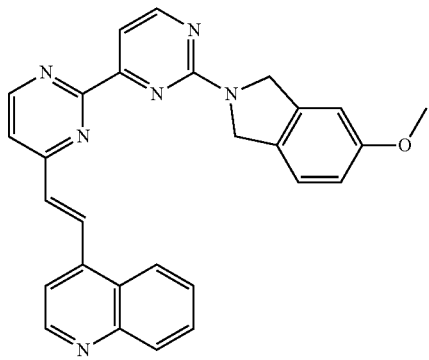 [SMILES: COc1ccc2c(c1)CN(c1nccc(-c3nccc(/C=C/c4ccnc5ccccc45)n3)n1)C2]

(E)-4-(2-(2'-(5-Methoxyisoindolin-2-yl)-[2,4'-bipyrimidin]-4-yl)vinyl)-1H-pyrrolo[2,3-b]pyridine

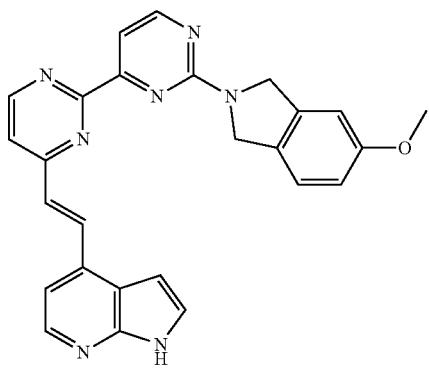 [SMILES: COc1ccc2c(c1)CN(c1nccc(-c3nccc(/C=C/c4ccnc5[nH]ccc45)n3)n1)C2]

(E)-4-(2-(2'-(5-Methoxyisoindolin-2-yl)-[2,4'-bipyrimidin]-4-yl)vinyl)pyrimidin-2-amine

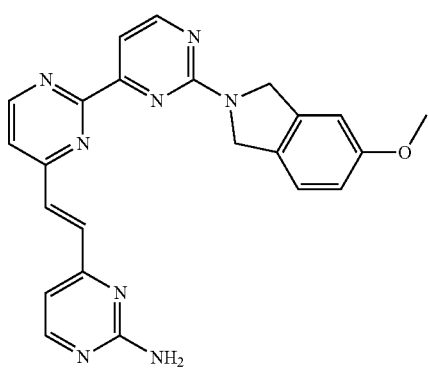

(E)-2-(4-(2-(Pyridin-4-yl)vinyl)-[2,4'-bipyrimidin]-2'-yl)isoindolin-5-ol
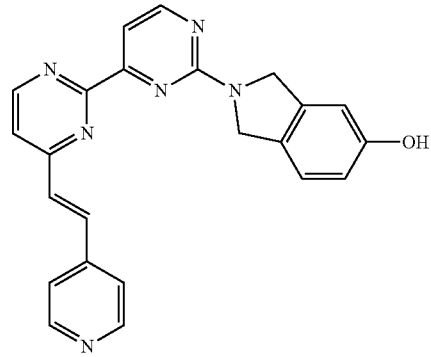
(E)-2-(4-(2-(Pyridin-4-yl)vinyl)-[2,4'-bipyrimidin]-2'-yl)isoindolin-5-yl trifluoromethanesulfonate
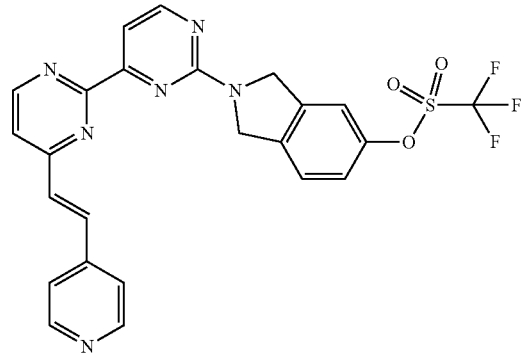 [SMILES: O=S(=O)(Oc1ccc2c(c1)CN(c1nccc(-c3nccc(/C=C/c4ccncc4)n3)n1)C2)C(F)(F)F]
(E)-2-(4-(2-(Pyridin-4-yl)vinyl)-[2,4'-bipyrimidin]-2'-yl)isoindoline-5-carbonitrile
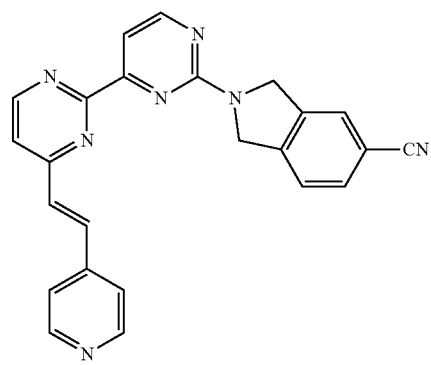 [SMILES: N#Cc1ccc2c(c1)CN(c1nccc(-c3nccc(/C=C/c4ccncc4)n3)n1)C2]
(E)-N,N-Dimethyl-2-((2-(4-(2-(pyridin-4-yl)vinyl)-[2,4'-bipyrimidin]-2'-yl)isoindolin-5-yl)oxy)ethanamine
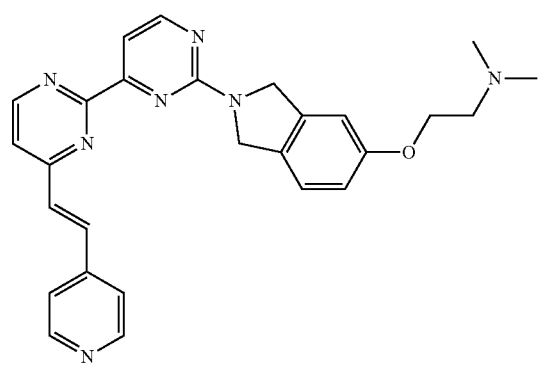 [SMILES: CN(C)CCOc1ccc2c(c1)CN(c1nccc(-c3nccc(/C=C/c4ccncc4)n3)n1)C2]

(E)-Methyl-2-((2-(4-(2-(pyridin-4-yl)vinyl)-[2,4'-bipyrimidin]-2'-yl)isoindolin-5-yl)oxy)acetate
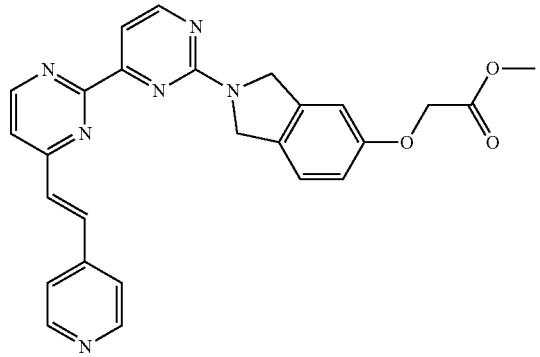
(E)-N-Methyl-2-((2-(4-(2-(pyridin-4-yl)vinyl)[2,4'-bipyrimidin]-2'-yl)isoindolin-5-yl)oxy)acetamide
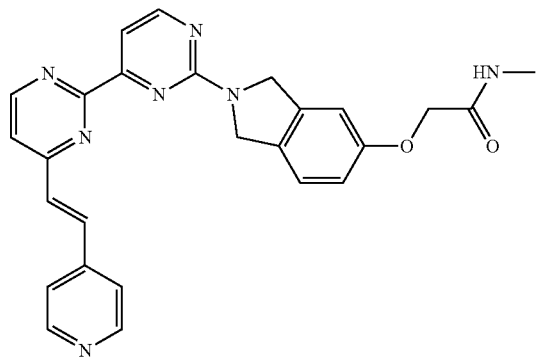
(E)-N-Ethyl-2-((2-(4-(2-(pyridin-4-yl)vinyl)-[2,4'-bipyrimidin]-2'-yl)isoindolin-5-yl)oxy)acetamide
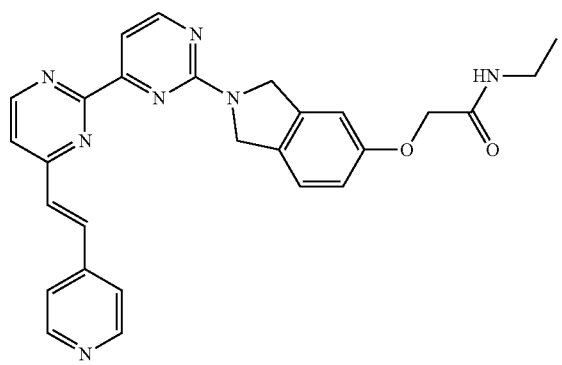 [SMILES: CCNC(=O)COc1ccc2c(c1)CN(c1nccc(-c3nccc(/C=C/c4ccncc4)n3)n1)C2]
(E)-N-Isopropyl-2-((2-(4-(2-(pyridin-4-yl)vinyl)-[2,4'-bipyrimidin]-2'-yl)isoindolin-5-yl)oxy)acetamide
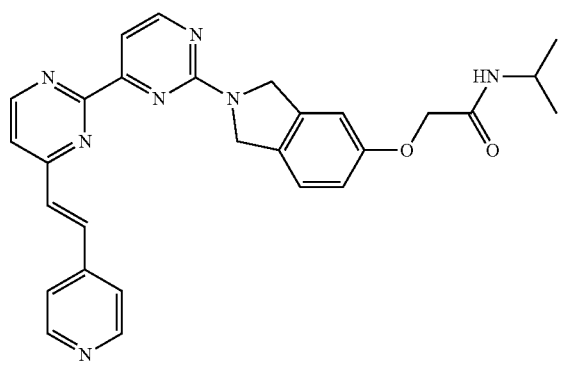 [SMILES: CC(C)NC(=O)COc1ccc2c(c1)CN(c1nccc(-c3nccc(/C=C/c4ccncc4)n3)n1)C2]

(E)-5-Fluoro-2-(4-(2-(pyridin-4-yl)vinyl)-[2,4'-bipyrimidin]-2'-yl)isoindoline

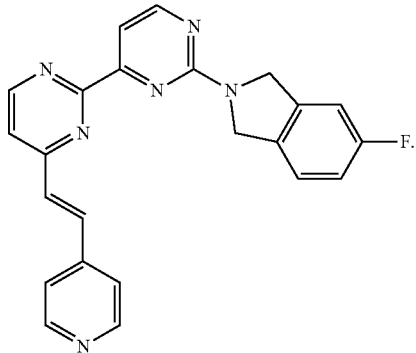

4. The compound of claim 1, wherein the compound has ROCK1, ROCK2, or ROCK1/2 inhibitory activities.

5. The compound of claim 1, wherein the compound has ROCK2 or ROCK1/2 inhibitory activities.

6. A pharmaceutical composition comprising one or more compounds of claim 1 and a pharmaceutically acceptable carrier, excipient, or diluent.

7. The composition of claim 6, wherein the compound has ROCK1, ROCK2, or ROCK1/2 inhibitory activities.

8. The composition of claim 7, wherein the compound has antifibrotic activity.

9. The compound of claim 1 or a pharmaceutically acceptable salt thereof, wherein the compound is selected from the following:

(E)-5-Methoxy-2-(4-(2-(pyridin-4-yl)vinyl)-[2,4'-bipyrimidin]-2'-yl)isoindoline

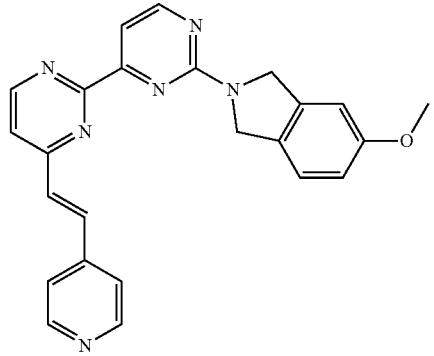

(E)-2-(4-(2-(Pyridin-4-yl)vinyl)-[2,4'-bipyrimidin]-2'-yl)isoindolin-5-ol

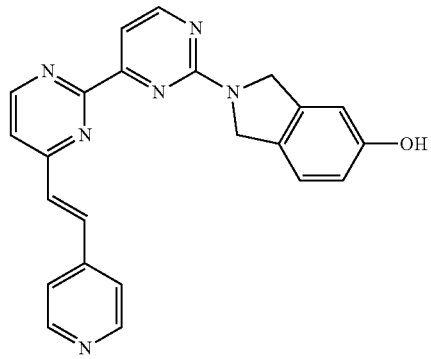

(E)-2-(4-(2-(Pyridin-4-yl)vinyl)-[2,4'-bipyrimidin]-2'-yl)isoindolin-5-yl trifluoromethanesulfonate
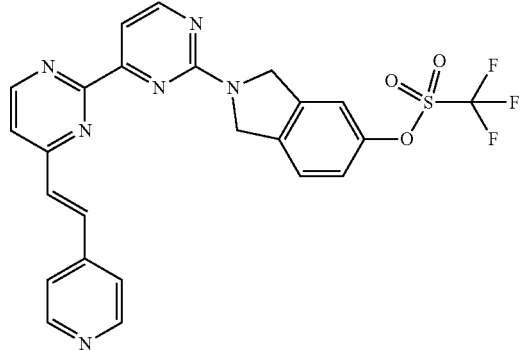 [SMILES: O=S(=O)(Oc1ccc2c(c1)CN(c1nccc(-c3nccc(/C=C/c4ccncc4)n3)n1)C2)C(F)(F)F]
(E)-2-(4-(2-(Pyridin-4-yl)vinyl)-[2,4'-bipyrimidin]-2'-yl)isoindoline-5-carbonitrile
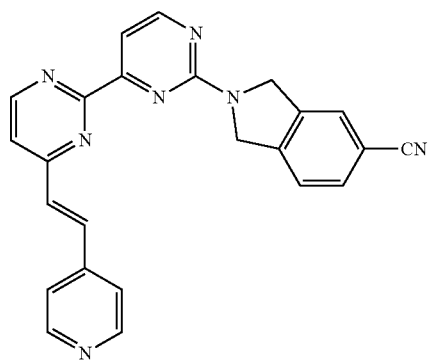
(E)-N,N-Dimethyl-2-((2-(4-(2-(pyridin-4-yl)vinyl)-[2,4'-bipyrimidin]-2'-yl)isoindolin-5-yl)oxy)ethanamine
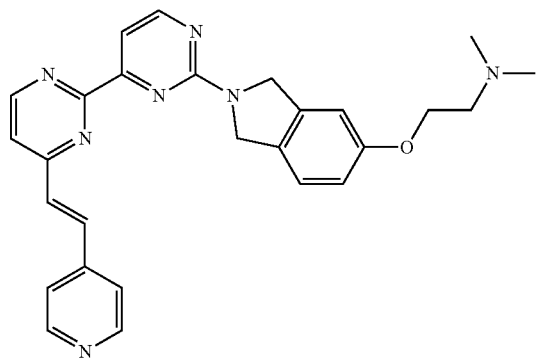
(E)-Methyl-2-((2-(4-(2-(pyridin-4-yl)yinyl)-[2,4'-bipyrimidin]-2'-yl)isoindolin-5-yl)oxy)acetate
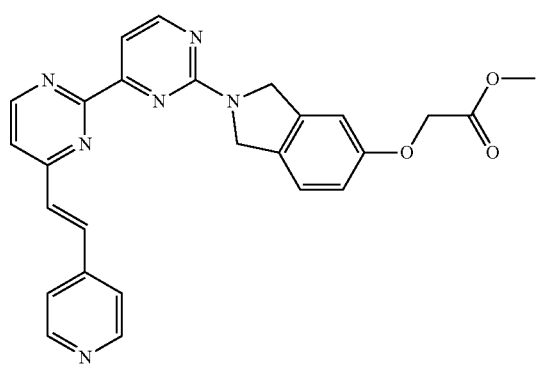 [SMILES: COC(=O)COc1ccc2c(c1)CN(c1nccc(-c3nccc(/C=C/c4ccncc4)n3)n1)C2]

(E)-N-Methyl-2-((2-(4-(2-(pyridin-4-yl)vinyl)-[2,4'-bipyrimidin]-2'-yl)isoindolin-5-yl)oxy)acetamide
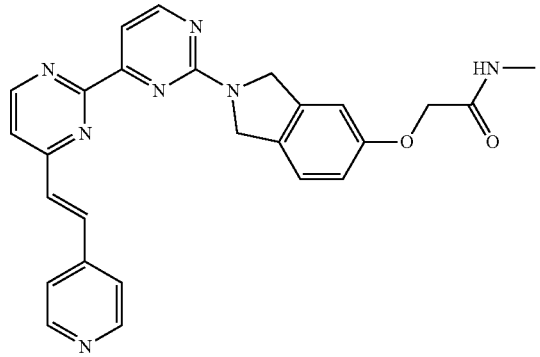
(E)-N-Ethyl-2-((2-(4-(2-(pyridin-4-yl)vinyl)-[2,4'-bipyrimidin]-2'-yl)isoindolin-5-yl)oxy)acetamide
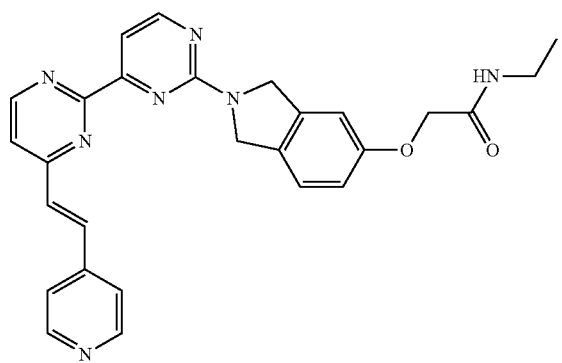
(E)-N-Isopropyl-2-((2-(4-(2-(pyridin-4-yl)vinyl)-[2,4'-bipyrimidin]-2'-yl)isoindolin-5-yl)oxy)acetamide
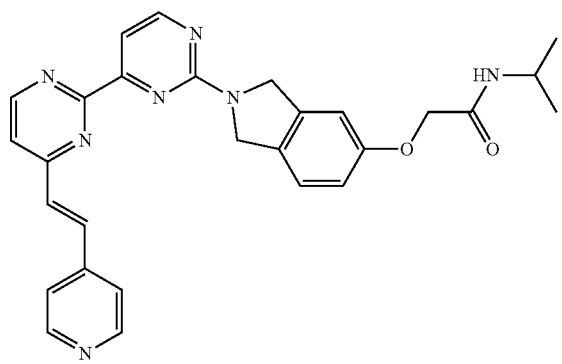 [SMILES: CC(C)NC(=O)COc1ccc2c(c1)CN(c1nccc(-c3nccc(/C=C/c4ccncc4)n3)n1)C2]
(E)-5-Fluoro-2-(4-(2-(pyridin-4-yl)vinyl)-[2,4'-bipyrimidin]-2'-yl)isoindoline
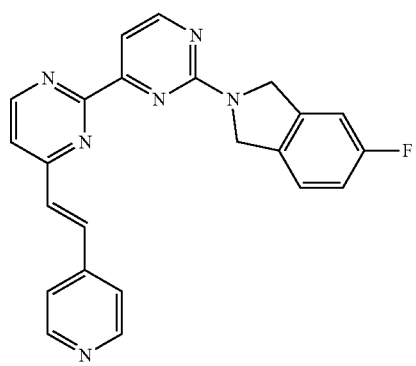 [SMILES: Fc1ccc2c(c1)CN(c1nccc(-c3nccc(/C=C/c4ccncc4)n3)n1)C2]

| | |
|---|---|
| (E)-5-Chloro-2-(4-(2-(pyridin-4-yl)vinyl)[2,4'-bipyrimidin]-2'-yl)isoindoline | 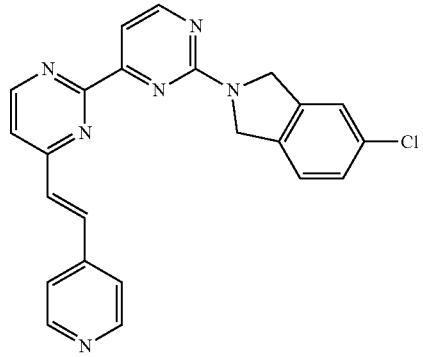 |
| (E)-5-Bromo-2-(4-(2-(pyridin-4-yl)vinyl)[2,4'-bipyrimidin]-2'-yl)isoindoline | 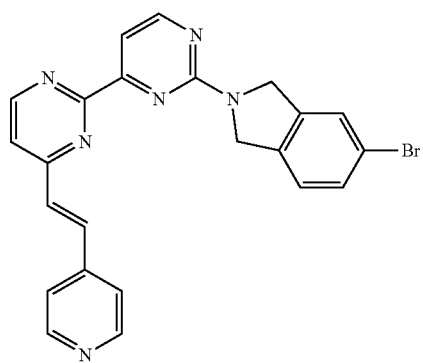 [SMILES: Brc1ccc2c(c1)CN(c1nccc(-c3nccc(/C=C/c4ccncc4)n3)n1)C2] |
| (E)-5-Iodo-2-(4-(2-(pyridin-4-yl)vinyl)[2,4'-bipyrimidin]-2'-yl)isoindoline | 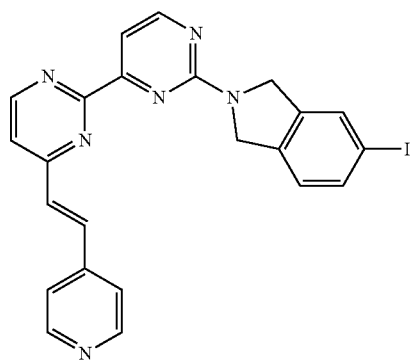 |
| (E)-5-Ethoxy-2-(4-(2-(pyridin-4-yl)vinyl)-[2,4'-bipyrimidin]-2'-yl)isoindoline | 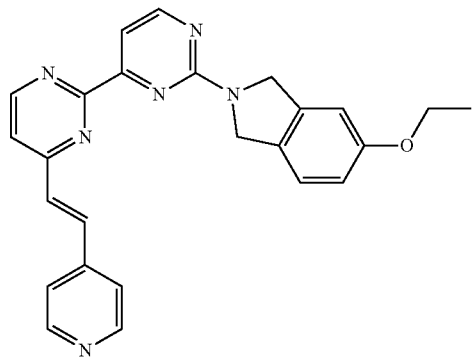 |

-continued
(E)-5-Isopropoxy-2-(4-(2-(pyridin-4-yl)vinyl)-[2,4'-bipyrimidin]-2'-yl)isoindoline
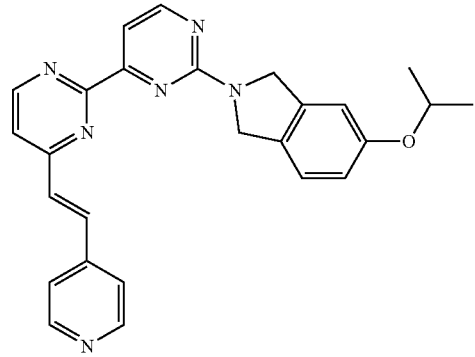 [SMILES: CC(C)Oc1ccc2c(c1)CN(c1nccc(-c3nccc(/C=C/c4ccncc4)n3)n1)C2]
(E)-5-Cyclopropoxy-2-(4-(2-(pyridin-4-yl)vinyl)-[2,4'-bipyrimidin]-2'-yl)isoindoline
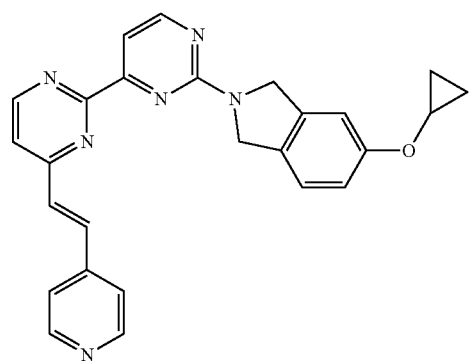 [SMILES: C(=C\c1ccnc(-c2ccnc(N3Cc4ccc(OC5CC5)cc4C3)n2)n1)/c1ccncc1]
(E)-5-Methyl-2-(4-(2-(pyridin-4-yl)vinyl)-[2,4'-bipyrimidin]-2'-yl)isoindoline
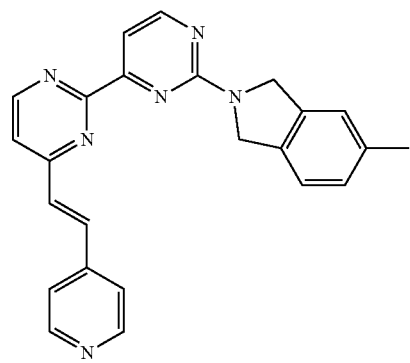 [SMILES: Cc1ccc2c(c1)CN(c1nccc(-c3nccc(/C=C/c4ccncc4)n3)n1)C2]
(E)-5-Ethyl-2-(4-(2-(pyridin-4-yl)vinyl)[2,4'-bipyrimidin]-2'-yl)isoindoline
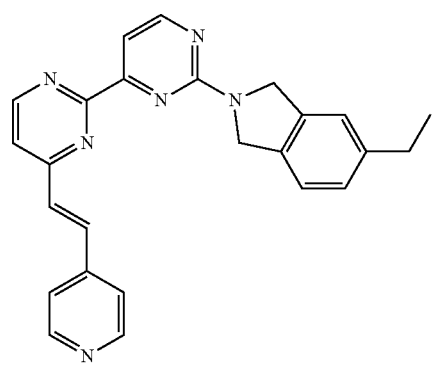

(E)-5-Cyclopropyl-2-(4-(2-(pyridin-4-yl)vinyl)-[2,4'-bipyrimidin]-2'-yl)isoindoline
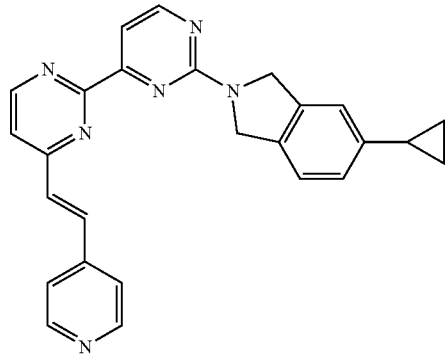 [SMILES: C(=C\c1ccnc(-c2ccnc(N3Cc4ccc(C5CC5)cc4C3)n2)n1)/c1ccncc1]
(E)-5-Amino-2-(4-(2-(pyridin-4-yl)vinyl)[2,4'-bipyrimidin]-2'-yl)isoindoline
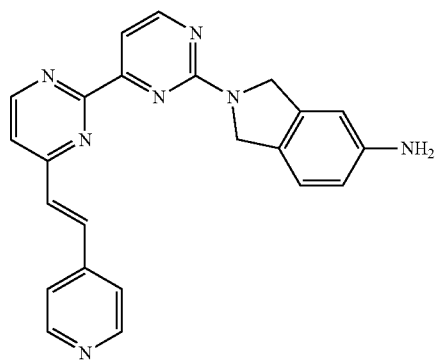 [SMILES: Nc1ccc2c(c1)CN(c1nccc(-c3nccc(/C=C/c4ccncc4)n3)n1)C2]
(E)-5-Methylamino-2-(4-(2-(pyridin-4-yl)vinyl)-[2,4'-bipyrimidin]-2'-yl)isoindoline
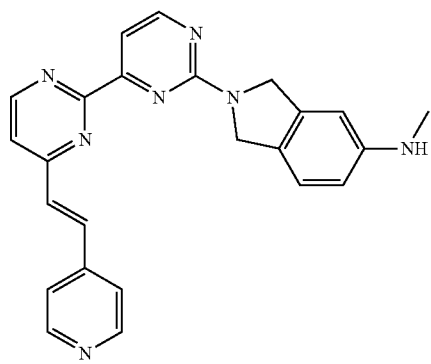
(E)-5-Dimethylamino-2-(4-(2-(pyridin-4-yl)vinyl)-[2,4'-bipyrimidin]-2'-yl)isoindoline
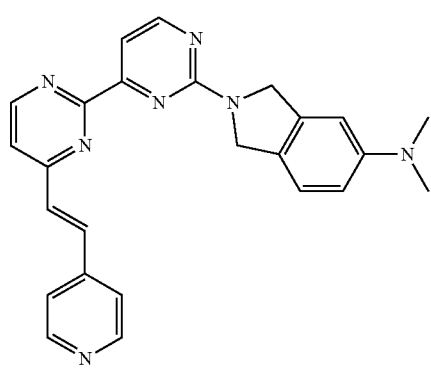 [SMILES: CN(C)c1ccc2c(c1)CN(c1nccc(-c3nccc(/C=C/c4ccncc4)n3)n1)C2]

(E)-5-Vinyl-2-(4-(2-(pyridin-4-yl)vinyl)-[2,4'-bipyrimidin]-2'-yl)isoindoline
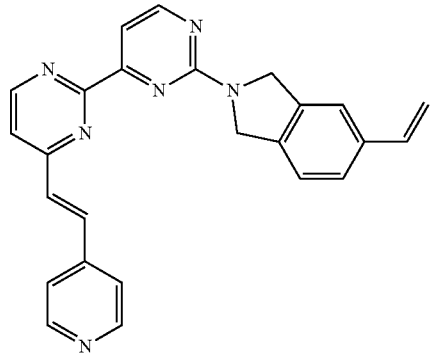 [SMILES: C=Cc1ccc2c(c1)CN(c1nccc(-c3nccc(/C=C/c4ccncc4)n3)n1)C2]
(E)-5-Propargyl-2-(4-(2-(pyridin-4-yl)vinyl)-[2,4'-bipyrimidin]-2'-yl)isoindoline
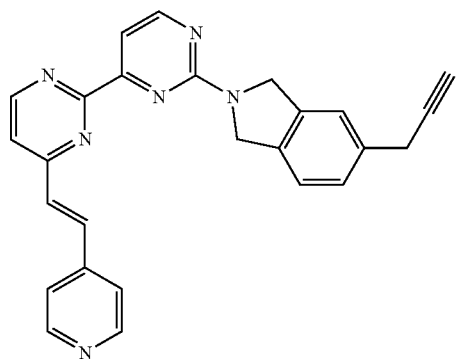 [SMILES: C#CCc1ccc2c(c1)CN(c1nccc(-c3nccc(/C=C/c4ccncc4)n3)n1)C2]
N-Methyl-2-[4-[4-[(E)-2-(4-pyridyl)vinyl]pyrimidin-2-yl]pyrimidin-2-yl]isoindoline-5-carboxamide
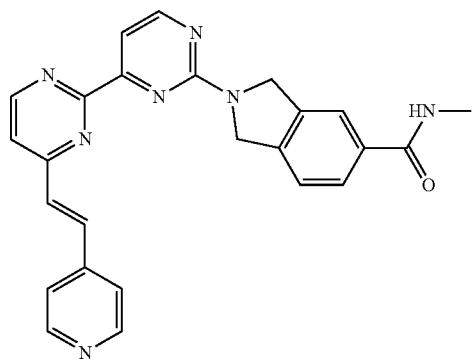 [SMILES: CNC(=O)c1ccc2c(c1)CN(c1nccc(-c3nccc(/C=C/c4ccncc4)n3)n1)C2]
N-Ethyl-2-[4-[4-[(E)-2-(4-pyridyl)vinyl]pyrimidin-2-yl]pyrimidin-2-yl]isoindoline-5-carboxamide
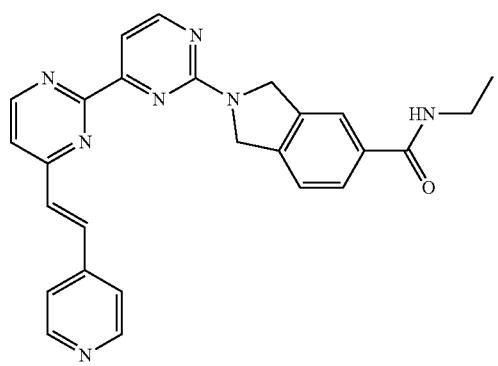 [SMILES: CCNC(=O)c1ccc2c(c1)CN(c1nccc(-c3nccc(/C=C/c4ccncc4)n3)n1)C2]

| | |
|---|---|
| N-Isopropyl-2-[4-[4-[(E)-2-(4-pyridyl)vinyl]pyrimidin-2-yl]pyrimidin-2-yl]isoindoline-5-carboxamide | 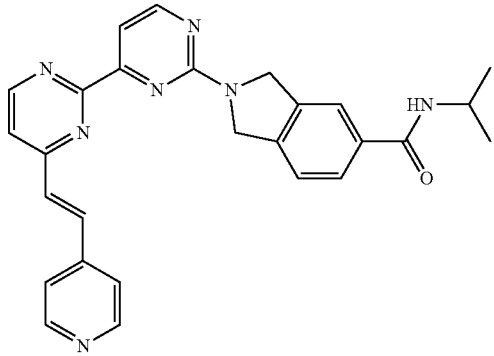 [SMILES: CC(C)NC(=O)c1ccc2c(c1)CN(c1nccc(-c3nccc(/C=C/c4ccncc4)n3)n1)C2] |
| N-Cyclopropyl-2-[4-[4-[(E)-2-(4-pyridyl)vinyl]pyrimidin-2-yl]pyrimidin-2-yl]isoindoline-5-carboxamide | 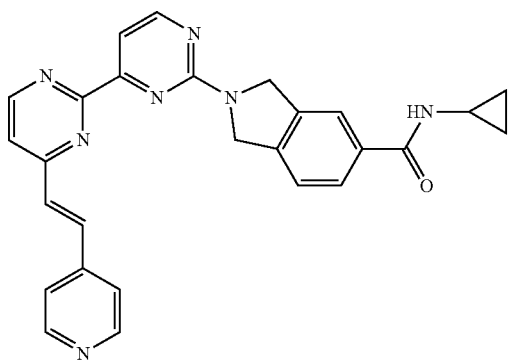 [SMILES: O=C(NC1CC1)c1ccc2c(c1)CN(c1nccc(-c3nccc(/C=C/c4ccncc4)n3)n1)C2] |
| N-(tert-Butyl)-2-[4-[4-[(E)-2-(4-pyridyl)vinyl]pyrimidin-2-yl]pyrimidin-2-yl]isoindoline-5-carboxamide | 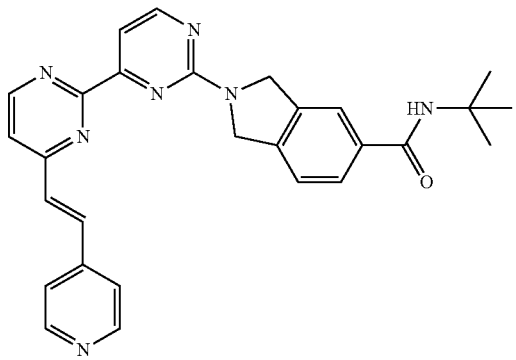 [SMILES: CC(C)(C)NC(=O)c1ccc2c(c1)CN(c1nccc(-c3nccc(/C=C/c4ccncc4)n3)n1)C2] |
| N',N'-Dimethyl-N-[2-[4-[4-[(E)-2-(4-pyridyl)vinyl]pyrimidin-2-yl]pyrimidin-2-yl]isoindolin-5-yl]ethane-1,2-diamine | 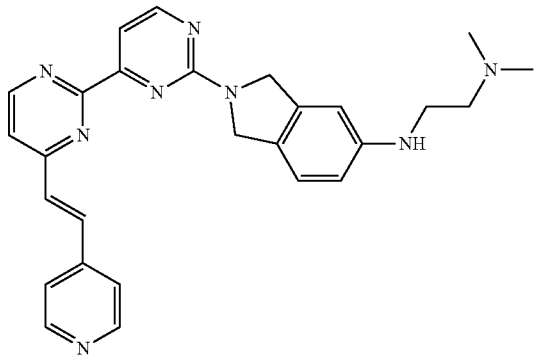 |

-continued
N,N,N'-Trimethyl-N'-[2-[4-[4-[(E)-2-(4-pyridyl)vinyl]pyrimidin-2-yl]pyrimidin-2-yl]isoindolin-5-yl]ethane-1,2-diamine
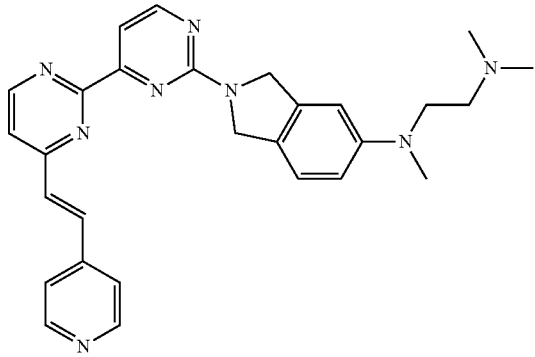 [SMILES: CN(C)CCN(C)c1ccc2c(c1)CN(c1nccc(-c3nccc(/C=C/c4ccncc4)n3)n1)C2]
4-[2-[2-[4-[4-[(E)-2-(4-Pyridyl)vinyl]pyrimidin-2-yl]pyrimidin-2-yl]isoindolin-5-yl]oxyethyl]morpholine
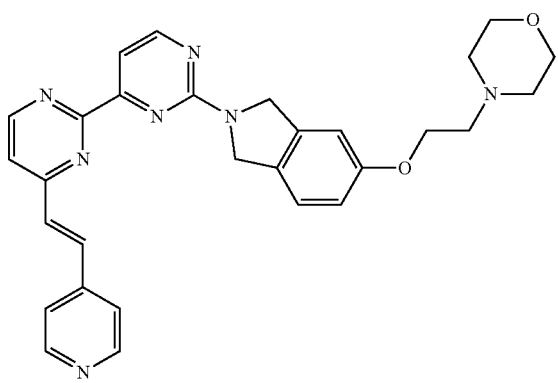 [SMILES: C(=C\c1ccnc(-c2ccnc(N3Cc4ccc(OCCN5CCOCC5)cc4C3)n2)n1)/c1ccncc1]
5-[2-(4-Methylpiperazin-1-yl)ethoxyl-2-[4-[4-[(E)-2-(4-pyridyl)vinyl]pyrimidin-2-yl]pyrimidin-2-yl]isoindoline
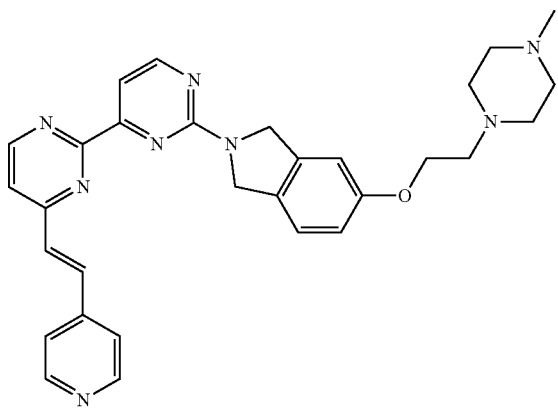 [SMILES: CN1CCN(CCOc2ccc3c(c2)CN(c2nccc(-c4nccc(/C=C/c5ccncc5)n4)n2)C3)CC1]
4-[2-[4-[4-[(E)-2-(4-Pyridyl)vinyl]pyrimidin-2-yl]pyrimidin-2-yl]isoindolin-5-yl]morpholine
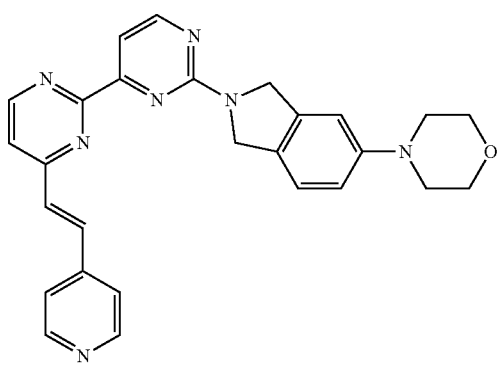 [SMILES: C(=C\c1ccnc(-c2ccnc(N3Cc4ccc(N5CCOCC5)cc4C3)n2)n1)/c1ccncc1]

-continued

| | |
|---|---|
| 5-(4-Methylpiperazin-1-yl)-2-[4-[4-[(E)-2-(4-pyridyl)vinyl]pyrimidin-2-yl]pyrimidin-2-yl]isoindoline | 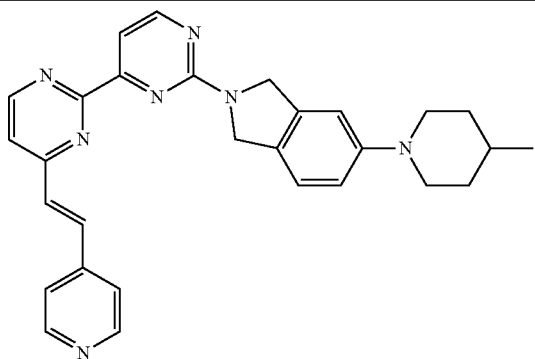 |
| 5-(1-Methylpyrazol-4-yl)-2-[4-[4-[(E)-2-(4-pyridyl)vinyl]pyrimidin-2-yl]pyrimidin-2-yl]isoindoline | 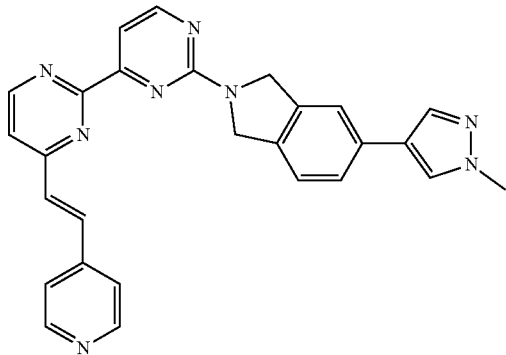 [SMILES: Cn1cc(-c2ccc3c(c2)CN(c2nccc(-c4nccc(/C=C/c5ccncc5)n4)n2)C3)cn1] |
| 5-Phenyl-2-[4-[4-[(E)-2-(4-pyridyl)vinyl]pyrimidin-2-yl]pyrimidin-2-yl]isoindoline | 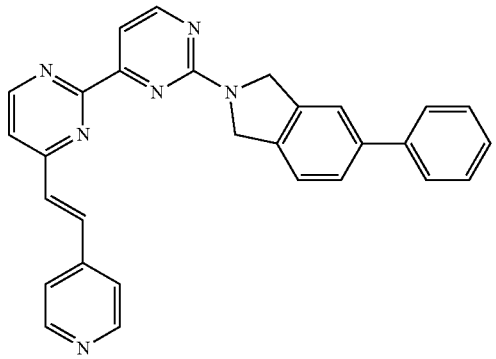 |

10. The compound of claim 1 or a pharmaceutically acceptable salt thereof, wherein the compound is selected from the following:

| | |
|---|---|
| 4-[(E)-2-[2-[2-(5-Methoxyisoindolin-2-yl)pyrimidin-4-yl]pyrimidin-4-yl]vinyl]pyridin-2-amine | 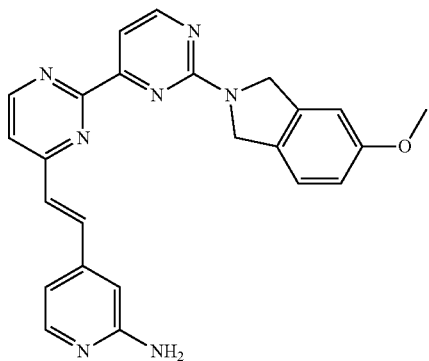 [SMILES: COc1ccc2c(c1)CN(c1nccc(-c3nccc(/C=C/c4ccnc(N)c4)n3)n1)C2] |

4-[(E)-2-[2-[2-(5-Fluoroisoindolin-2-yl)pyrimidin-4-yl]pyrimidin-4-yl]vinyl]pyridin-2-amine
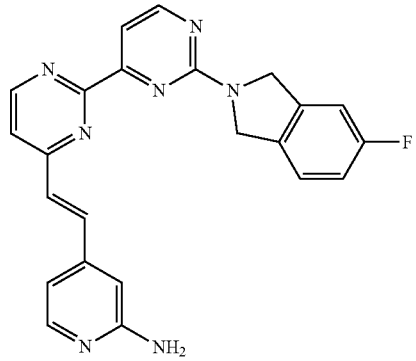 [SMILES: Nc1cc(/C=C/c2ccnc(-c3ccnc(N4Cc5ccc(F)cc5C4)n3)n2)ccn1]
4-[(E)-2-[2-[2-(5-Chloroisoindolin-2-yl)pyrimidin-4-yl]pyrimidin-4-yl]vinyl]pyridin-2-amine
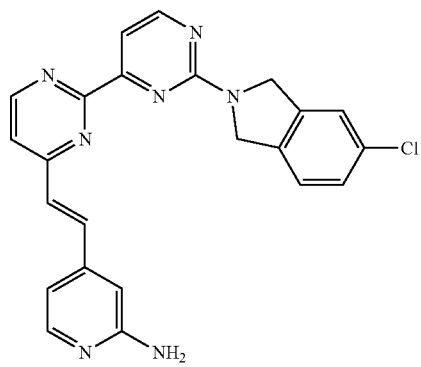 [SMILES: Nc1cc(/C=C/c2ccnc(-c3ccnc(N4Cc5ccc(Br)cc5C4)n3)n2)ccn1]
4-[(E)-2-[2-[2-(5-Bromoisoindolin-2-yl)pyrimidin-4-yl]pyrimidin-4-yl]vinyl]pyridin-2-amine
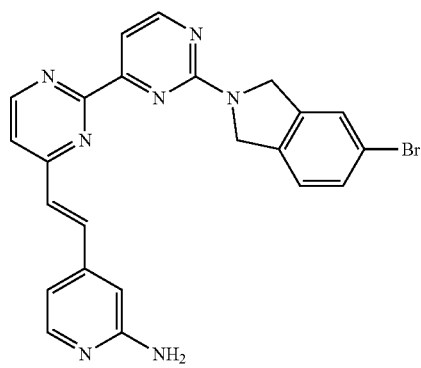
2-[4-[4-[(E)-2-(2-Amino-4-pyridyl)vinyl]pyrimidin-2-yl]pyrimidin-2-yl]isoindoline-5-carbonitrile
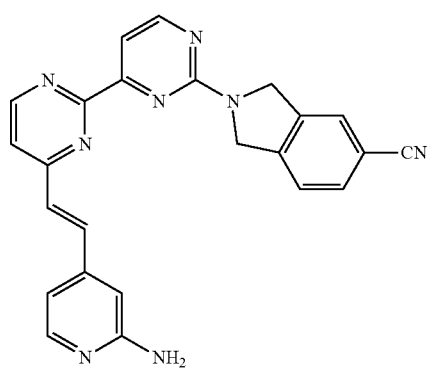 [SMILES: N#Cc1ccc2c(c1)CN(c1nccc(-c3nccc(/C=C/c4ccnc(N)c4)n3)n1)C2]

| | |
|---|---|
| 4-[(E)-2-[2-[2-[5-(4-Methylpiperazin-1-yl)isoindolin-2-yl]pyrimidin-4-yl]pyrimidin-4-yl]vinyl]pyridin-2-amine | 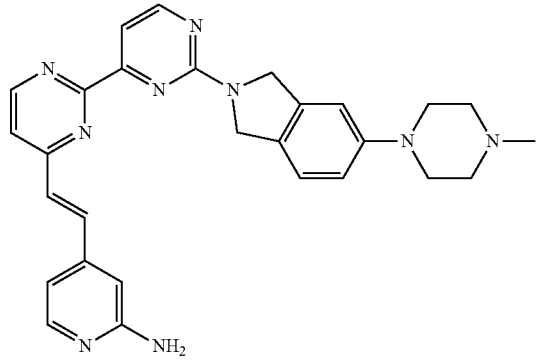 [SMILES: CN1CCN(c2ccc3c(c2)CN(c2nccc(-c4nccc(/C=C/c5ccnc(N)c5)n4)n2)C3)CC1] |
| 4-[(E)-2-[2-[2-(5-Morpholinoisoindolin-2-yl)pyrimidin-4-yl]pyrimidin-4-yl]vinyl]pyridin-2-amine | 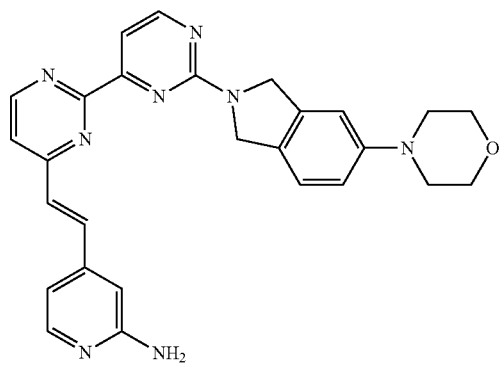 [SMILES: Nc1cc(/C=C/c2ccnc(-c3ccnc(N4Cc5ccc(N6CCOCC6)cc5C4)n3)n2)ccn1] |
| 2-[4-[4-[(E)-2-(2-Amino-4-pyridyl)vinyl]pyrimidin-2-yl]pyrimidin-2-yl]-N-methyl-isoindoline-5-carboxamide | 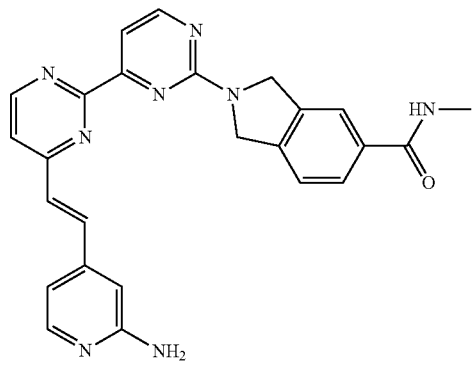 [SMILES: CNC(=O)c1ccc2c(c1)CN(c1nccc(-c3nccc(/C=C/c4ccnc(N)c4)n3)n1)C2] |
| 2-[4-[4-[(E)-2-(2-Amino-4-pyridyl)vinyl]pyrimidin-2-yl]pyrimidin-2-yl]-N-ethyl-isoindoline-5-carboxamide | 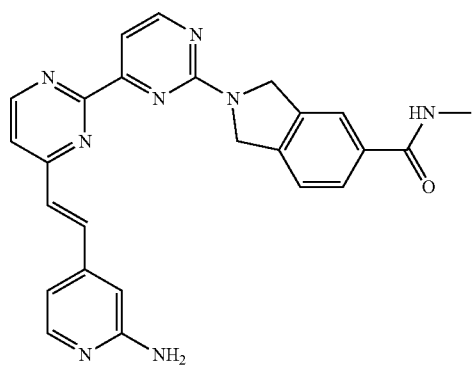 [SMILES: CNC(=O)c1ccc2c(c1)CN(c1nccc(-c3nccc(/C=C/c4ccnc(N)c4)n3)n1)C2] |

| | |
|---|---|
| 2-[4-[4-[(E)-2-(2-Amino-4-pyridyl)vinyl]pyrimidin-2-yl]pyrimidin-2-yl]-N-isopropyl-isoindoline-5-carboxamide | 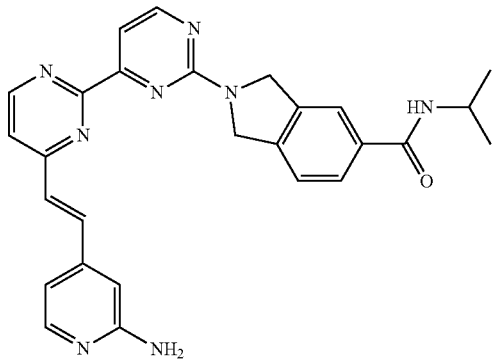 [SMILES: CC(C)NC(=O)c1ccc2c(c1)CN(c1nccc(-c3nccc(/C=C/c4ccnc(N)c4)n3)n1)C2] |
| 4-[(E)-2-[2-[2-[5-[2-(Dimethylamino)ethoxy]isoindolin-2-yl]pyrimidin-4-yl]pyrimidin-4-yl]vinyl]pyridin-2-amine | 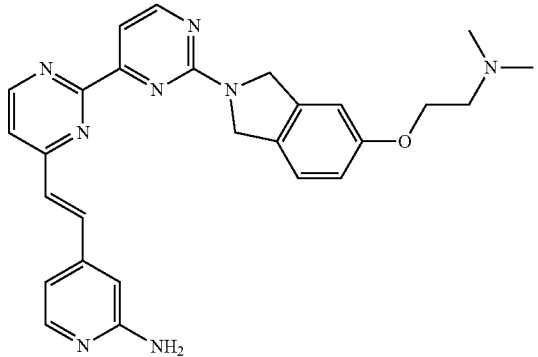 [SMILES: CN(C)CCOc1ccc2c(c1)CN(c1nccc(-c3nccc(/C=C/c4ccnc(N)c4)n3)n1)C2] |
| 4-[(E)-2-[2-[2-[5-(1-Methylpyrazol-4-yl)isoindolin-2-yl]pyrimidin-4-yl]pyrimidin-4-yl]vinyl]pyridin-2-amine | 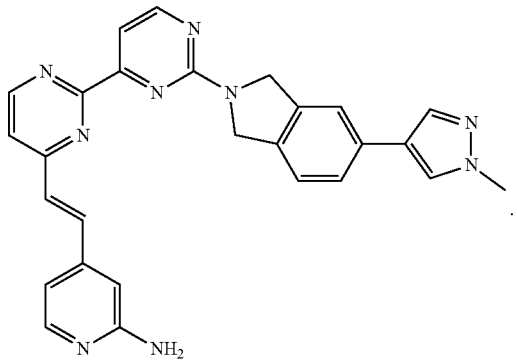 [SMILES: Cn1cc(-c2ccc3c(c2)CN(c2nccc(-c4nccc(/C=C/c5ccnc(N)c5)n4)n2)C3)cn1] |

11. The compound of claim 2, wherein the compound has ROCK1, ROCK2, or ROCK1/2 inhibitory activities.

12. The compound of claim 2, wherein the compound has ROCK2 or ROCK1/2 inhibitory activities.

13. A pharmaceutical composition comprising one or more compounds of claim 2 and a pharmaceutically acceptable carrier, excipient, or diluent.

14. The compound of claim 3, wherein the compound has ROCK1, ROCK2, or ROCK1/2 inhibitory activities.

15. The compound of claim 3, wherein the compound has ROCK2 or ROCK1/2 inhibitory activities.

16. A pharmaceutical composition comprising one or more compounds of claim 3 and a pharmaceutically acceptable carrier, excipient, or diluent.

17. The compound of claim 9, wherein the compound has ROCK1, ROCK2, or ROCK1/2 inhibitory activities.

18. The compound of claim 9, wherein the compound has ROCK2 or ROCK1/2 inhibitory activities.

19. A pharmaceutical composition comprising one or more compounds of claim 9 and a pharmaceutically acceptable carrier, excipient, or diluent.

20. The compound of claim 10, wherein the compound has ROCK1, ROCK2, or ROCK1/2 inhibitory activities.

21. The compound of claim 10, wherein the compound has ROCK2 or ROCK1/2 inhibitory activities.

22. A pharmaceutical composition comprising one or more compounds of claim 10 and a pharmaceutically acceptable carrier, excipient, or diluent.

* * * * *